United States Patent
Zhu et al.

(10) Patent No.: US 10,188,724 B2
(45) Date of Patent: Jan. 29, 2019

(54) EFFICIENT MUCOSAL VACCINATION MEDIATED BY THE NEONATAL FC RECEPTOR

(71) Applicant: University of Maryland, College Park, College Park, MD (US)

(72) Inventors: Xiaoping Zhu, Clarksville, MD (US); Lilin Ye, Hyattsville, MD (US); Li Lu, Beltsville, MD (US)

(73) Assignee: University of Maryland, College Park, College Park, MD (US)

( * ) Notice: Subject to any disclaimer, the term of this patent is extended or adjusted under 35 U.S.C. 154(b) by 0 days.

(21) Appl. No.: 14/961,938

(22) Filed: Dec. 8, 2015

(65) Prior Publication Data

US 2016/0184425 A1    Jun. 30, 2016

Related U.S. Application Data

(62) Division of application No. 12/932,310, filed on Feb. 23, 2011, now Pat. No. 9,238,683.

(51) Int. Cl.

| | |
|---|---|
| *A61K 39/245* | (2006.01) |
| *C07K 14/005* | (2006.01) |
| *C07K 14/315* | (2006.01) |
| *C07K 14/35* | (2006.01) |
| *C07K 14/47* | (2006.01) |
| *A61K 39/21* | (2006.01) |
| *A61K 39/12* | (2006.01) |
| *C12N 7/00* | (2006.01) |
| *A61K 39/00* | (2006.01) |

(52) U.S. Cl.
CPC ........... *A61K 39/245* (2013.01); *A61K 39/12* (2013.01); *A61K 39/21* (2013.01); *C07K 14/005* (2013.01); *C07K 14/3156* (2013.01); *C07K 14/35* (2013.01); *C07K 14/4713* (2013.01); *C07K 14/4748* (2013.01); *C12N 7/00* (2013.01); *A61K 2039/54* (2013.01); *A61K 2039/541* (2013.01); *A61K 2039/542* (2013.01); *A61K 2039/543* (2013.01); *A61K 2039/544* (2013.01); *A61K 2039/545* (2013.01); *A61K 2039/552* (2013.01); *A61K 2039/55561* (2013.01); *A61K 2039/57* (2013.01); *A61K 2039/6056* (2013.01); *C07K 2319/30* (2013.01); *C12N 2710/16634* (2013.01); *C12N 2740/16234* (2013.01)

(58) Field of Classification Search
CPC .. A61K 2039/505; A61K 38/00; A61K 48/00; A61K 38/177; A61K 39/145; A61K 47/6843; A61K 47/6901; C07K 2317/52; C07K 14/70503; C07K 16/1018
See application file for complete search history.

(56) References Cited

U.S. PATENT DOCUMENTS

| | | | |
|---|---|---|---|
| 7,067,129 B2 | 6/2006 | Blumberg | |
| 8,025,873 B2 | 9/2011 | George et al. | |
| 8,097,805 B2 | 1/2012 | Drane et al. | |
| 2005/0013828 A1 | 1/2005 | George et al. | |
| 2005/0031628 A1 | 2/2005 | George et al. | |

OTHER PUBLICATIONS

Spitsin et al. Vaccine, 2009, vol. 27, Issue 9, pp. 1289-1292.*
Loureiro et al. Journal of Virology, Dec. 29, 2010. vol. 85, No. 6, pp. 3010-3014.*
Ye et al. Nat Biotechnology, published online on Jan. 16, 2011, Vo. 29, pp. 158-163.
Geraghty et al., Virology 2001, vol. 285, pp. 366-375.
Yang et al., Bioconjugate Chem. 2010, vol. 21, pp. 875-883.
Geraghty et al. Virology 2000, vol. 268, pp. 147-158.
Drupolic and Cohenm 2012. Expert Rev Vaccines 11:1429-1440.
Gosselin et al., Arch. Immunol Ther. Exp. 2009, vol. 57, pp. 311-323.
Gallican et al., J. Immunol. 2001, vol. 166, pp. 3451-3457.
Cheong et al., Blood, published online before Jul. 28, 201, vol. 116, pp. 3828-3838.

* cited by examiner

*Primary Examiner* — Bao Q Li
(74) *Attorney, Agent, or Firm* — Hodgson Russ LLP

(57) ABSTRACT

The present invention relates to methods and compositions for enhancing delivery of vaccine antigens to the mucosal epithelium, the composition comprising an antigen from an infectious agent fused with an Fc fragment of an immunoglobulin recognized by the neonatal receptors (FcRn). The composition is effective in eliciting a protective long-term memory T cell immune response against infection at a distant mucosal site.

16 Claims, 16 Drawing Sheets

Figure 1:
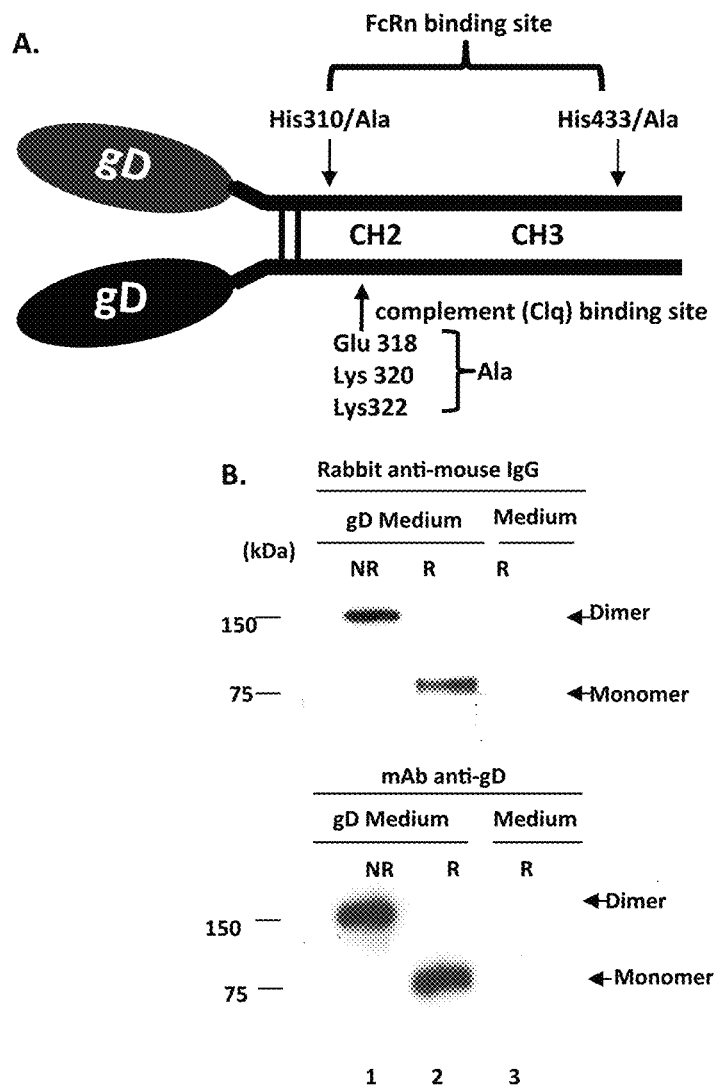
Figure 2:
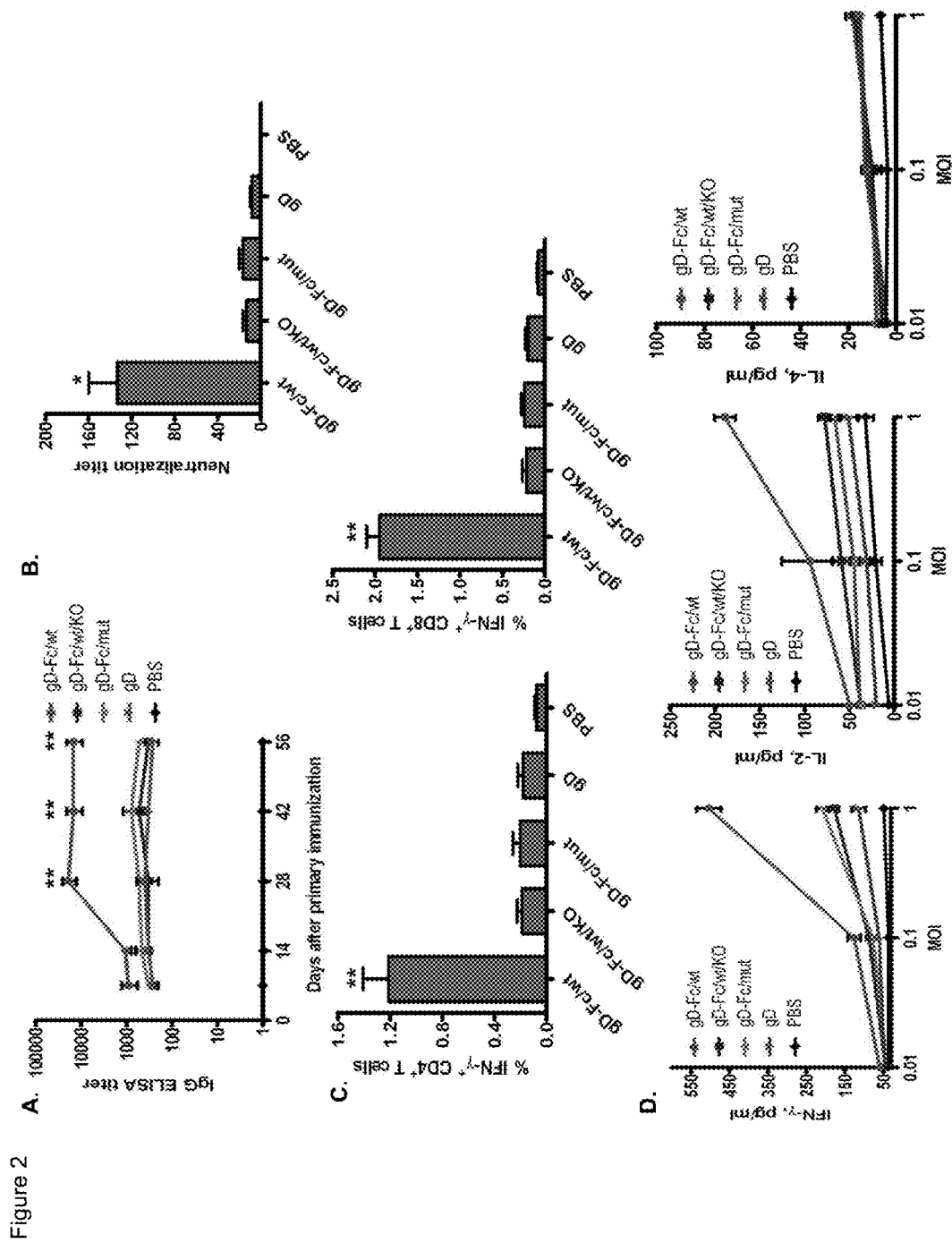

Specification includes a Sequence Listing.

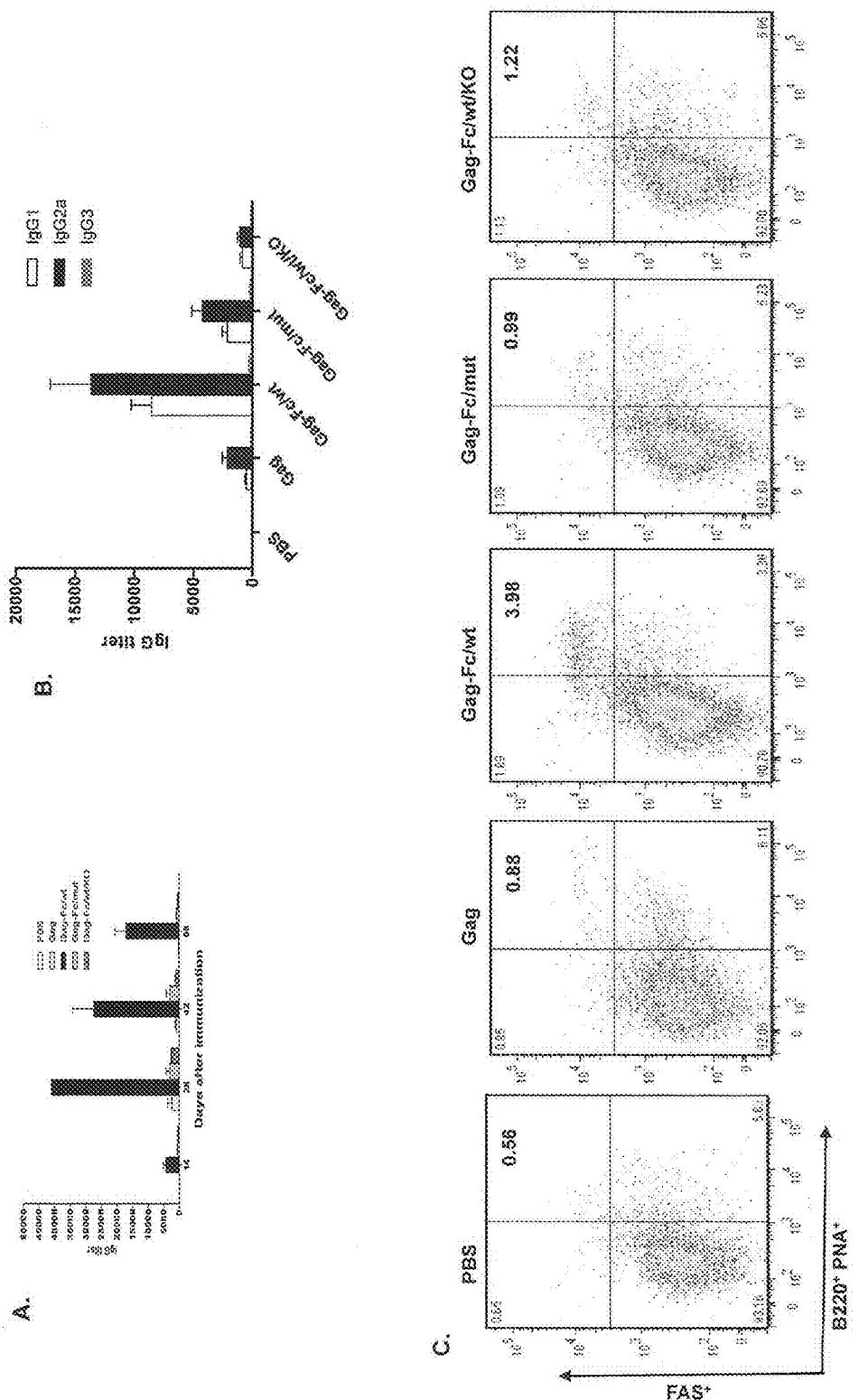

SEQUENCE LISTING

```
<160> NUMBER OF SEQ ID NOS: 12

<210> SEQ ID NO 1
<211> LENGTH: 14
<212> TYPE: PRT
<213> ORGANISM: Artificial Sequence
<220> FEATURE:
<223> OTHER INFORMATION: Insert of glycine and serine residues

<400> SEQUENCE: 1

Gly Ser Gly Gly Gly Gly Ser Gly Gly Gly
1               5                   10

Gly Ser Gly Ser

<210> SEQ ID NO 2
<211> LENGTH: 1020
<212> TYPE: DNA
<213> ORGANISM: Artificial sequence
<220> FEATURE:
<223> OTHER INFORMATION: Herpes Simplex Virus type 2 gD antigen

<400> SEQUENCE: 2
atggggcgtt tgacctccgg cgtcgggacg gcggccctgc                        40
tagttgtcgc ggtgggactc cgcgtcgtct gcgccaaata                        80
cgccttagca gacccctcgc ttaagatggc cgatcccaat                       120
cgatttcgcg ggaagaacct tccggttttg gaccagctga                       160
ccgacccccc cggggtgaag cgtgtttacc acattcagcc                       200
gagcctggag gacccgttcc agccccccag catcccgatc                       240
actgtgtact acgcagtgct ggaacgtgcc tgccgcagcg                       280
tgctcctaca tgccccatcg gaggcccccc agatcgtgcg                       320
cggggcttcg gacgaggccc gaaagcacac gtacaacctg                       360
accatcgcct ggtatcgcat gggagacaat tgcgctatcc                       400
ccatcacggt tatggaatac accgagtgcc cctacaacaa                       440
gtcgttgggg gtctgcccca tccgaacgca gccccgctgg                       480
agctactatg acagctttag cgccgtcagc gaggataacc                       520
tgggattcct gatgcacgcc cccgccttcg agaccgcggg                       560
tacgtacctg cggctagtga agataaacga ctggacggag                       600
atcacacaat ttatcctgga gcaccgggcc cgcgcctcct                       640
gcaagtacgc tctccccctg cgcatccccc cggcagcgtg                       680
cctcacctcg aaggcctacc aacagggcgt gacggtcgac                       720
agcatcggga tgttaccccg ctttatcccc gaaaaccagc                       760
gcaccgtcgc cctatacagc ttaaaaatcg ccgggtggca                       800
cggccccaag cccccgtaca ccagcaccct gctgccgccg                       840
gagctgtccg acaccaccaa cgccacgcaa cccgaactcg                       880
ttccggaaga ccccgaggac tcggccctct tagaggatcc                       920
cgccgggacg gtgtcttcgc agatcccccc aaactggcac                       960
atcccgtcga tccaggacgt cgcgccgcac cacgcccccg                      1000
ccgcccccag caacccgggc                                            1020
```

<210> SEQ ID NO 3
<211> LENGTH: 57
<212> TYPE: DNA
<213> ORGANISM: Artificial Sequence
<220> FEATURE:
<223> OTHER INFORMATION: primer

<400> SEQUENCE: 3
cccaagctta ccatggggcg tttgacctcc ggcgtcagat         40
cccgagccac ctcctcc         57

<210> SEQ ID NO 4
<211> LENGTH: 38
<212> TYPE: DNA
<213> ORGANISM: Artificial Sequence
<220> FEATURE:
<223> OTHER INFORMATION: Primer

<400> SEQUENCE: 4
ggacccaccc ccgcctgatc cgcccgggtt gctgggggg         38

<210> SEQ ID NO 5
<211> LENGTH: 58
<212> TYPE: DNA
<213> ORGANISM: Artificial Sequence
<220> FEATURE:
<223> OTHER INFORMATION: primer

<400> SEQUENCE: 5
ggatcaggcg ggggtgggtc cggaggaggt ggctcgggat         40
ctgagcccag agggccca         58

<210> SEQ ID NO 6
<211> LENGTH: 25
<212> TYPE: DNA
<213> ORGANISM: Artificial Sequence
<220> FEATURE:
<223> OTHER INFORMATION: primer

<400> SEQUENCE: 6
ccggaattct catttacccg gagtc         25

<210> SEQ ID NO 7
<211> LENGTH: 702
<212> TYPE: DNA
<213> ORGANISM: Artificial Sequence
<220> FEATURE:
<223> OTHER INFORMATION: mouse Fc fragment with C1q mutation

<400> SEQUENCE: 7
gagcccagag ggcccacaat caagccctgt cctccatgca         40
aatgcccagc acctaacctc ttgggtggac catccgtctt         80
catcttccct ccaaagatca aggatgtact catgatctcc         120
ctgagcccca tagtcacatg tgtggtggtg gatgtgagcg         160
aggatgaccc agatgtccag atcagctggt ttgtgaacaa         200
cgtggaagta cacacagctc agacacaaac ccatagagag         240
gattacaaca gtactctccg ggtggtcagt gccctcccca         280
tccagcacca ggactggatg agtggcaagg agttcaaatg         320
caaggtcaac aacaaagacc tcccagcgcc catcgagaga         360

| | |
|---|---|
| accatctcaa aacccaaagg gtcagtaaga gctccacagg | 400 |
| tatatgtctt gcctccacca gaagaagaga tgactaagaa | 440 |
| acaggtcact ctgacctgca tggtcacaga cttcatgcct | 480 |
| gaagacattt acgtggagtg gaccaacaac gggaaaacag | 520 |
| agctaaacta caagaacact gaaccagtcc tggactctga | 560 |
| tggttcttac ttcatgtaca gcaagctgag agtggaaaag | 600 |
| aagaactggg tggaaagaaa tagctactcc tgttcagtgg | 640 |
| tccacgaggg tctgcacaat caccacacga ctaagagctt | 680 |
| ctcccggact ccgggtaaat ga | 702 |

<210> SEQ ID NO 8
<211> LENGTH: 1689
<212> TYPE: DNA
<213> ORGANISM: Artificial Sequence
<220> FEATURE:
<223> OTHER INFORMATION: gD-Fc fusion polynucleotide

<400> SEQUENCE: 8

| | |
|---|---|
| aaatacgcct tagcagaccc ctcgcttaag atggccgatc | 40 |
| ccaatcgatt tcgcgggaag aaccttccgg ttttggacca | 80 |
| gctgaccgac cccccggggg tgaagcgtgt ttaccacatt | 120 |
| cagccgagcc tggaggaccc gttccagccc cccagcatcc | 160 |
| cgatcactgt gtactacgca gtgctggaac gtgcctgccg | 200 |
| cagcgtgctc ctacatgccc catcggaggc ccccagatc | 240 |
| gtgcgcgggg cttcggacga ggcccgaaag cacacgtaca | 280 |
| acctgaccat cgcctggtat cgcatgggag acaattgcgc | 320 |
| tatccccatc acggttatgg aatacaccga gtgcccctac | 360 |
| aacaagtcgt tgggggtctg ccccatccga acgcagcccc | 400 |
| gctggagcta ctatgacagc tttagcgccg tcagcgagga | 440 |
| taacctggga ttcctgatgc acgccccccgc cttcgagacc | 480 |
| gcgggtacgt acctgcggct agtgaagata aacgactgga | 520 |
| cggagatcac acaatttatc ctggagcacc gggcccgcgc | 560 |
| ctcctgcaag tacgctctcc ccctgcgcat cccccccggca | 600 |
| gcgtgcctca cctcgaaggc ctaccaacag ggcgtgacgg | 640 |
| tcgacagcat cgggatgtta ccccgcttta tccccgaaaa | 680 |
| ccagcgcacc gtcgccctat acagcttaaa aatcgccggg | 720 |
| tggcacggcc ccaagccccc gtacaccagc accctgctgc | 760 |
| cgccggagct gtccgacacc accaacgcca cgcaacccga | 800 |
| actcgttccg gaagacccg aggactcggc cctcttagag | 840 |
| gatcccgccg ggacggtgtc ttcgcagatc cccccaaact | 880 |
| ggcacatccc gtcgatccag gacgtcgcgc cgcaccacgc | 920 |
| ccccgccgcc cccagcaacc cgggcggatc aggcggggt | 960 |
| gggtccggag gaggtggctc gggatctgag cccagagggc | 1000 |

-continued

| | |
|---|---|
| ccacaatcaa gccctgtcct ccatgcaaat gcccagcacc | 1040 |
| taacctcttg ggtggaccat ccgtcttcat cttccctcca | 1080 |
| aagatcaagg atgtactcat gatctccctg agccccatag | 1120 |
| tcacatgtgt ggtggtggat gtgagcgagg atgacccaga | 1160 |
| tgtccagatc agctggtttg tgaacaacgt ggaagtacac | 1200 |
| acagctcaga cacaaaccca tagagaggat tacaacagta | 1240 |
| ctctccgggt ggtcagtgcc ctccccatcc agcaccagga | 1280 |
| ctggatgagt ggcaaggagt tcaaatgcaa ggtcaacaac | 1320 |
| aaagacctcc cagcgcccat cgagagaacc atctcaaaac | 1360 |
| ccaaagggtc agtaagagct ccacaggtat atgtcttgcc | 1400 |
| tccaccagaa gaagagatga ctaagaaaca ggtcactctg | 1440 |
| acctgcatgg tcacagactt catgcctgaa gacatttacg | 1480 |
| tggagtggac caacaacggg aaaacagagc taaactacaa | 1520 |
| gaacactgaa ccagtcctgg actctgatgg ttcttacttc | 1560 |
| atgtacagca gctgagagt ggaaaagaag aactgggtgg | 1600 |
| aaagaaatag ctactcctgt tcagtggtcc acgagggtct | 1640 |
| gcacaatcac cacacgacta agagcttctc ccggactccg | 1680 |
| ggtaaatga | 1689 |

<210> SEQ ID NO 9
<211> LENGTH: 20
<212> TYPE: DNA
<213> ORGANISM: Artificial Sequence
<220> FEATURE:
<223> OTHER INFORMATION: CpG sequence

<400> SEQUENCE: 9

| | |
|---|---|
| tccatgacgt tcctgacgtt | 20 |

<210> SEQ ID NO 10
<211> LENGTH: 38
<212> TYPE: DNA
<213> ORGANISM: Artificial Sequence
<220> FEATURE:
<223> OTHER INFORMATION: primer

<400> SEQUENCE: 10

| | |
|---|---|
| ctggtcgctt ccgtgctacc tagaacttta aatgcatg | 38 |

<210> SEQ ID NO 11
<211> LENGTH: 60
<212> TYPE: DNA
<213> ORGANISM: Artificial Sequence
<220> FEATURE:
<223> OTHER INFORMATION: primer

<400> SEQUENCE: 11

| | |
|---|---|
| agatcccgag ccacctcctc cggacccacc cccgcctgat | 40 |
| cccaaaactc ttgccttatg | 60 |

<210> SEQ ID NO 12
<211> LENGTH: 1458
<212> TYPE: DNA
<213> ORGANISM: Artificial Sequence
<220> FEATURE:
<223> OTHER INFORMATION: Gag P24 from HIV-I fused with Fc wild type
fragment of mouse IgG2a

<400> SEQUENCE: 12

| | |
|---|---:|
| atgcccatgg ggtctctgca accgctggcc accttgtacc | 40 |
| tgctggggat gctggtcgct tccgtgctac ctagaactt | 80 |
| aaatgcatgg gtaaaagtag tagaagagaa ggctttcagc | 120 |
| ccagaagtaa tacccatgtt ttcagcatta tcagaaggag | 160 |
| ccaccccaca agatttaaac accatgctaa acacagtggg | 200 |
| gggacatcaa gcagccatgc aaatgttaaa agagaccatc | 240 |
| aatgaggaag ctgcagaatg ggatagagta catccagtgc | 280 |
| atgcagggcc tattgcacca ggccagatga gagaaccaag | 320 |
| gggaagtgac atagcaggaa ctactagtac ccttcaggaa | 360 |
| caaataggat ggatgacaaa taatccacct atcccagtag | 400 |
| gagaaattta taaaagatgg ataatcctgg gattaaataa | 440 |
| aatagtaaga atgtatagcc ctaccagcat tctggacata | 480 |
| agacaaggac caaaagaacc ttttagagac tatgtagacc | 520 |
| ggttctataa aactctaaga gccgagcaag cttcacagga | 560 |
| ggtaaaaaat tggatgacag aaaccttgtt ggtccaaaat | 600 |
| gcgaacccag attgtaagac tattttaaaa gcattgggac | 640 |
| cagcggctac actagaagaa atgatgacag catgtcaggg | 680 |
| agtaggagga cccggccata aggcaagagt tttgggatca | 720 |
| ggcggggggtg ggtccggagg aggtggctcg ggatctgagc | 760 |
| ccagagggcc cacaatcaag ccctgtcctc catgcaaatg | 800 |
| cccagcacct aacctcttgg gtggaccatc cgtcttcatc | 840 |
| ttccctccaa agatcaagga tgtactcatg atctccctga | 880 |
| gccccatagt cacatgtgtg gtggtggatg tgagcgagga | 920 |
| tgacccagat gtccagatca gctggtttgt gaacaacgtg | 960 |
| gaagtacaca cagctcagac acaaacccat agagaggatt | 1000 |
| acaacagtac tctccgggtg gtcagtgccc tccccatcca | 1040 |
| gcaccaggac tggatgagtg caaggcatt cgcatgcgca | 1080 |
| gtcaacaaca agacctccc agcgcccatc gagagaacca | 1120 |
| tctcaaaacc caagggtca gtaagagctc cacaggtata | 1160 |
| tgtcttgcct ccaccagaag aagagatgac taagaaacag | 1200 |
| gtcactctga cctgcatggt cacagacttc atgcctgaag | 1240 |
| acatttacgt ggagtggacc aacaacggga aaacagagct | 1280 |
| aaactacaag aacactgaac cagtcctgga ctctgatggt | 1320 |
| tcttacttca tgtacagcaa gctggagtg aaaagaaga | 1360 |
| actgggtgga aagaaatagc tactcctgtt cagtggtcca | 1400 |

-continued

```
cgagggtctg cacaatcacc acacgactaa gagcttctcc                    1440
cggactccgg gtaaatga                                            1458
```

EFFICIENT MUCOSAL VACCINATION MEDIATED BY THE NEONATAL FC RECEPTOR

This invention was funded by the National Institutes of Health. The Government has certain rights in the invention pursuant to NIH grant R01AI065892, AI067965, and R21AI073139.

INTRODUCTION

Most pathogens initiate their infections through mucosal surfaces of the respiratory, gastrointestinal and urogenital tracts. An effective vaccine must therefore induce both mucosal and systemic immune responses to cope with early infection and pathogen spread (Neutra, M. R. & Kozlowski, P. A., 2006, Nat. Reb. Immunol 6, 148-158; Holmgren, J. & Czerkinsky, C., 2005, Nat. Med. 11 Suppl S45-S53; McGhee, J. R. et al., 1992, Vaccine 10, 75-88; Gallichan, W. S. & Rosenthal, K. L., 1998, J. Infect. Dis. 177, 1155-1161). Delivery of vaccine antigens through the mucosal surface would be an ideal route to achieve mucosal, and potentially, systemic immunity because of the close association between mucosal epithelial cells and the immune effector cells within the lamina propria (Neutra and Kozlowski, 2006, supra; Holmgren and Czerkinsky, 2005, supra; McGhee et al., 1992, supra). However, since epithelial monolayers lining the mucosal surfaces are impervious to macromolecule diffusion due to their intercellular tight junctions (Neutra, M. R. et al., 2001, Nat. Immunol. 2, 1004-1009), the mucosal epithelium is a natural barrier for vaccine delivery. Different approaches have been explored to circumvent this problem, such as targeting mucosal vaccines onto differentiated microfold (M) cells that punctuate the mucosal epithelium (Nochi, T. et al. 2007, J. Exp. Med. 204, 2789-2796). However, since columnar epithelial cells comprise the great majority of mucosal surfaces, alternative mucosal vaccine delivery strategies that target these abundant epithelial cells may increase the efficacy of mucosal vaccines.

Therefore, there is a need for a mucosal vaccine able to penetrate the mucosal epithelia and induce a systemic immune response that is both protective and long-lasting.

BRIEF DESCRIPTION OF THE INVENTION

The present invention satisfies the need above. In this application is described a method for mucosal vaccination which is shown to provide prolonged protection from infection at a site different than the vaccination site.

The present inventors took advantage of the ability of neonatal Fc receptor (FcRn) to transport immunoglobulin G (IgG) antibody across mucosal surfaces. FcRn is a MHC class I-related molecule which allows fetuses or newborns to obtain maternal IgG via the placental or intestinal route (Ghetie, V. and Ward, E. S., 2000, Annu. Rev. Immunol. 18, 739-766; He, W. et al., 2008, Nature 455, 542-546). FcRn is known to also transport IgG antibody across mucosal surfaces in adult life (Dickinson, B. L. et al., 1999, J. Clin. Invest. 104, 903-911; Roopenian, d. C. and Akilesh, S., 2007, Nat. Rev. Immunol. 7, 715-725; Baker, K. et al., 2009, Semin. Immunopathol. 31, 223-236; Yoshida, M. et al., 2006, J. clin. Invest. 116, 2142-2151) and lead to resistance to intestinal pathogens (Yoshida et al., 2006, supra). The FcRn receptor binds IgG (but not other immunoglobulin classes such as IgA, IgD, IgM and IgE) at a relatively lower pH, actively transports the IgG transcellularly in a luminal to serosal direction or vice versa, and then releases the IgG at a relatively higher pH found in the interstitial fluids or luminal surfaces. Observations of IgG transport across mucosal epithelia by FcRn imply that FcRn may also transport an antigen, if fused with the IgG Fc-fragment (Fc), across the mucosal barrier. Therefore, FcRn-mediated mucosal vaccine delivery, if feasible, may allow the host to specifically sample an Fc-fused subunit vaccine in the mucosal lumen, followed by transport of an intact antigen across the mucosal epithelial barrier.

Using two different model antigens from two different pathogens which cause disease and initiate infection at the mucosa of the genital tract of the subject, and further defined the protective immune response. The present inventors determined the ability of FcRn to deliver a vaccine, comprising a fusion of an Fc-fragment from an immunoglobulin subclass which binds the FcRn in the mucosa of the subject, with an antigen from a pathogen of interest, across the respiratory mucosal barrier. Intranasal administration of a gD antigen from herpes simplex virus type-2 (HSV-2), or the p24 protein from HIV Gag, fused to the Fc-fragment administered along with a CpG adjuvant resulted in local and systemic immunity including durable memory responses by B and T cells. The immune response was sufficient for protection against intravaginal challenge with the pathogen source of the antigen.

Immunological memory, an important criterion for any vaccine, is the formation and maintenance of a reservoir of memory T and B lymphocytes with both adequate size and quality to maintain efficient immune surveillance for prolonged periods thereby providing the host with ability to respond faster and more vigorously to a second encounter with the pathogen or vaccine antigen (Ahmed, R. and Gray, D., 1996, Science 272, 54-60; Bernasconi, N. L. et al., 2002, Science 298, 2199-2202). To date, immunological memory (Bernasconi, et al., 2002) has been a concern in protein-based subunit mucosal vaccine development because preparations elicited levels of immunity immediately after vaccination but that immunity waned rapidly over time. The Fc-antigen fusion protein vaccine described in this application overcomes this drawback.

A striking feature in this study is that FcRn targeted mucosal immunization promoted and sustained high levels of antigen-specific plasma cells and memory B and T cells at least 6 months after the boost confirming that the Fc-antigen fusion proteins induce strong antibody and cellular immune responses at both mucosal and systemic sites against the vaccine antigen.

Therefore, the present invention provides a composition and method for delivering a desired antigen across the mucosal epithelium. The method comprises taking advantage of the ability of the neonatal Fc receptor (FcRn) to transport IgG molecules through epithelial cells present in the respiratory, intestinal and other mucosal epithelia. The composition comprises the desired antigen fused to an Fc-fragment of an immunoglobulin recognized by the FcRn of the subject. When this fusion molecule is introduced to a mucosal tissue, the FcRn mediates the transport of the Fc-antigen fusion across polarized epithelial cells lining mucosal surfaces. When the antigen is from an infectious agent, transport of the Fc-antigen through the mucosal surface results in induction of both a humoral and systemic immune response protective against challenge with the infectious agent at a site different than the vaccination site.

Therefore, it is an object of the present invention to provide a method for transporting a desired antigen across a mucosal epithelium, comprising fusing said antigen with a Fc-fragment of an IgG to produce an Fc-antigen fusion protein and introducing said Fc-antigen fusion protein to a mucosal epithelium.

It is another object of the present invention to provide a composition comprising a nucleic acid encoding a Fc-fragment from an IgG for use in producing a fusion protein with the desired vaccine antigen. In one embodiment, the Fc encoded by the nucleic acid is comprised of the hinge region, and the CH2 and CH3 domains. Vectors comprising said nucleic acid and host cells transformed with said vectors are also an object of the invention.

It is yet another object of the present invention to provide novel vector constructs for cloning a desired antigen such that an Fc-antigen fusion protein can be recombinantly expressed, as well as host cells transformed with said vector.

It is also another object of the present invention to provide compositions comprising a fusion protein comprising a Fc-fragment of an IgG and a desired antigen.

It is yet another object of the present invention to provide a method for producing and purifying a fusion protein comprising a Fc-fragment from an IgG and a desired antigen, comprising:

growing a host cell containing a vector capable of expressing an Fc-antigen fusion protein in a suitable culture medium, causing expression of said vector sequence as defined above under suitable conditions for production of soluble protein and, and recovering said Fc-antigen fusion protein.

It is also an object of the present invention to provide kits for the preparation of an Fc-antigen fusion protein.

It is yet another object of the present invention to provide a mucosal vaccine, with or without adjuvant, comprising a Fc-antigen fusion protein of the present invention, wherein the antigen is from an infectious agent, in an amount effective to elicit an immune response in an animal against said infectious agent; and a pharmaceutically acceptable diluent, carrier, or excipient. The vaccine according to the present invention is inherently safe, is not painful to administer, and should not result in adverse side effects to the vaccinated individual.

It is another object of the present invention to provide a mucosal DNA vaccine comprising a polynucleotide or hybrid DNA encoding an Fc-antigen fusion peptide.

It is another object of the present invention to provide a method for eliciting in a subject an immune response against an infectious agent, the method comprising administering to a subject a DNA fragment comprising a Fc-antigen hybrid DNA.

It is another object of the present invention to provide a method for eliciting in a subject a mucosal and/or systemic immune response against an infectious agent, the method comprising administering to a subject a composition comprising Fc-antigen fusion protein of the present invention.

All the objects of the present invention are considered to have been met by the embodiments as set out below.

BRIEF DESCRIPTION OF THE DRAWINGS

FIG. 1. Design and characterization of HSV-2 gD fused to IgG Fc fragment.

(A). Schematic illustration for the genetic fusion of HSV-2 gD and murine Fcg2a cDNA to create a gD-Fc fusion gene. Mutations were made in the CH2 domain of Fcg2a fragment by using site-directed mutagenesis to replace Glu318, Lys320, and Lys322 with Ala residues to remove the complement C1q binding site, and His 310 and His 433 with Ala residues to eliminate FcRn binding sites. The fourteen codons for glycine and serine residues (GSGGGGSGGGGSGS, SEQ ID NO:1) were inserted between the gD and Fc fragments.

(B). The gD-Fc fusion proteins were secreted by CHO cells. The gD-Fc was recognized by either rabbit anti-mouse IgG (top panel) or a mAb anti-gD (bottom panel). The fusion protein was exhibited as a dimer under non-reducing (NR) or a monomer under reducing (R) condition.

FIG. 2. FcRn-targeted mucosal vaccination induces enhanced gD-specific antibody and T cell responses. The 20 ug gD-Fc/wt, gD-Fc/mut, gD, or PBS in combination with 20 ug CpG were i.n. administered into wild-type (WT) or FcRn knockout (KO) mice.

(A). Measurement of anti-HSV-2 gD-specific IgG antibody titers in serum before and after the boost immunization. HSV-2 gD-specific IgG antibody at indicated days was measured in serum by ELISA. Immunization conditions are displayed at the right. The curves represent mean values for each group (±S.E.M.). Values marked with asterisk in this and subsequent figures: *$P<0.05$; **$P<0.01$.

(B). Test of neutralizing activity in the immunized sera. Sera were heat-inactivated, diluted 10-fold, then in twofold steps in MEM with 2% FBS. HSV-2 (50 PFU) was added and incubated at 37° C. for 1 hr. Finally, the mixture were removed and washed, overlaid with 0.8% methylcellulose in 2% FBS containing DMEM and further incubated for 72 hr at 37° C. The titers were expressed as the reciprocal of the twofold serial dilution preventing the appearance of the cytopathic effects (CPE) over control sera. Each assay was done in triplicate.

(C). The percentage of IFN-γ producing T cells in the spleen 4 days after the boost. Spleen cells from the immunized mice were stimulated for 10 hr with purified gD or medium control. Lymphocytes were gated by forward and side scatter and T cells labeled with anti-CD3 and identified by their respective surface markers CD4 and CD8 and intracellular IFN-g staining. Immunization conditions are displayed on the bottom. Numbers represent the percentage of IFN-$g^+$ $CD3^+$ $CD4^+$ (left panel) or IFN-$g^+$ $CD3^+$ $CD8^+$ (right panel) T cells. Isotype controls included FITC-mouse-IgG1 with baseline response.

(D) Cytokine secretions from the stimulated spleen T cells. Spleen cells were collected on day 4 after the boost. Cells were stimulated in vitro specifically with different multiplicity of infection (MOI) of inactivated HSV-2 virus as indicated for 24 hr. Cytokines IFN-g, IL-2, and IL-4 in the culture supernatant were detected by ELISA. Data are representative of three experiments with three immunized mice pooled in each group.

FIG. 3. Local immune responses induced by FcRn-targeted mucosal immunization.

(A). Accumulation of activated B cells in germinal centers (GCs) in the mediastinal lymph nodes (MeLNs) and spleen. Representative flow cytometric analyses of GC B cells among CD19+ B220+ B cells in the MeLNs and spleen 10 days after the boost. $B220^+PNA^{high}$ cells are B cells that exhibit the phenotypic attributes of GC B cells. The GC staining in spleen was used as a positive control. Numbers are the percentage of activated GC B cells (PNA+FAS+) among gated B cells and are representative of three independent experiments.

(B). GC formation and presence of activated B cells following immunizations as indicated. Frozen MeLN sections at day 10 from the immunized mice were co-stained with biotin-PNA (developed with avidin-FITC) and Alexa647 labeled anti-IgD. Scale bar represents 50 mm.

(C). Quantitative analysis of GCs following immunization. The dynamics of the frequency of germinal center B cells (FAS+PNA+, gated on CD19+B220+ cells) were plotted on day 10, 22 and 35 after the boost. Data indicate the mean and S.E.M., n=5 mice.

(D). The formation of inducible bronchus-associated lymphoid tissue (iBALT). Frozen serial sections of the lung were stained with biotin-PNA (GC, red) and anti-B220 (B cells, green), followed by Alexa 488-conjugated IgG of corresponding species and Alexa 555-Avidin. The nucleus is stained with DAPI (blue). A germinal center-like structure is shown in the merged panel by the white color. The data are representative of sections from at least three independent mice. Images were originally obtained at 10× magnification. Scale bars represent 100 μm.

(E)+(F). Presence of HSV-2 gD-specific T lymphocytes in the lung (E) and MeLNs (F). Lung or MeLN cells from mice 4 days after the boost were collected. Lymphocytes were gated based on their forward scatter (FSC) vs. side scatter (SSC) profile. Intracellular staining for IFN-g was performed after surface staining of CD4 and CD8 molecules. The profiles shown are representative of five mice from three separate experiments. Numbers indicate percentages of IFN-g-producing T lymphocytes from gated $CD4^+$ and $CD8^+$ T cells.

Figure 4:
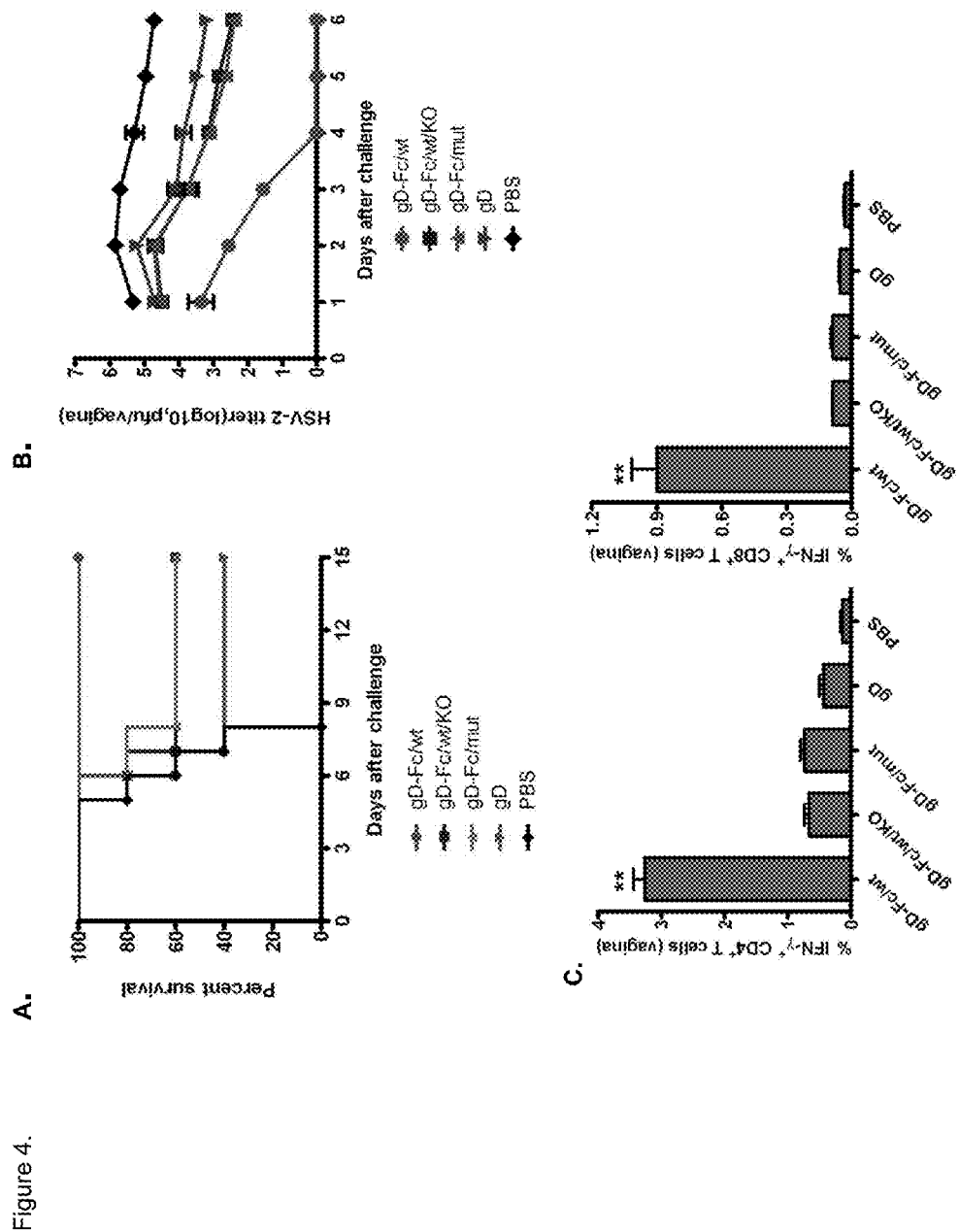

FIG. 4. FcRn-targeted mucosal immunization provides protective immunity to intravaginal (ivag) challenge with virulent HSV-2 186.

(A) Mean survival following genital HSV-2 challenge. Four weeks after the immunization, groups of five mice were challenged intravaginally with $1 \times 10^4$ pfu of HSV-2 strain 186. Percentage of mice from protection on the indicated days is calculated as the number of mice surviving divided by the number of mice in each group and represented two similar experiments.

(B) Mean of viral titers following HSV-2 challenge. Virus titers were measured from vaginal washes by taking swabs on the indicated days after HSV-2 inoculation based on a plaque assay on Vero cell monolayers.

(C). Increased presence of HSV-specific T lymphocytes in the vaginal epithelium after challenge. Lymphocytes were harvested from collagenase-digested vaginal tissues 4 days intravaginal inoculation of virus. Intracellular staining for IFN-g expression on $CD4^+$ and $CD8^+$ T cells was analyzed after gating on viable CD3+ lymphocytes. The numbers in each column show the percentage of IFN-g-positive T lymphocytes from the gated $CD4^+$ or $CD8^+$ T cells. Data shown are of a representative from three experiments using 3 mice per experiment.

Figure 5:
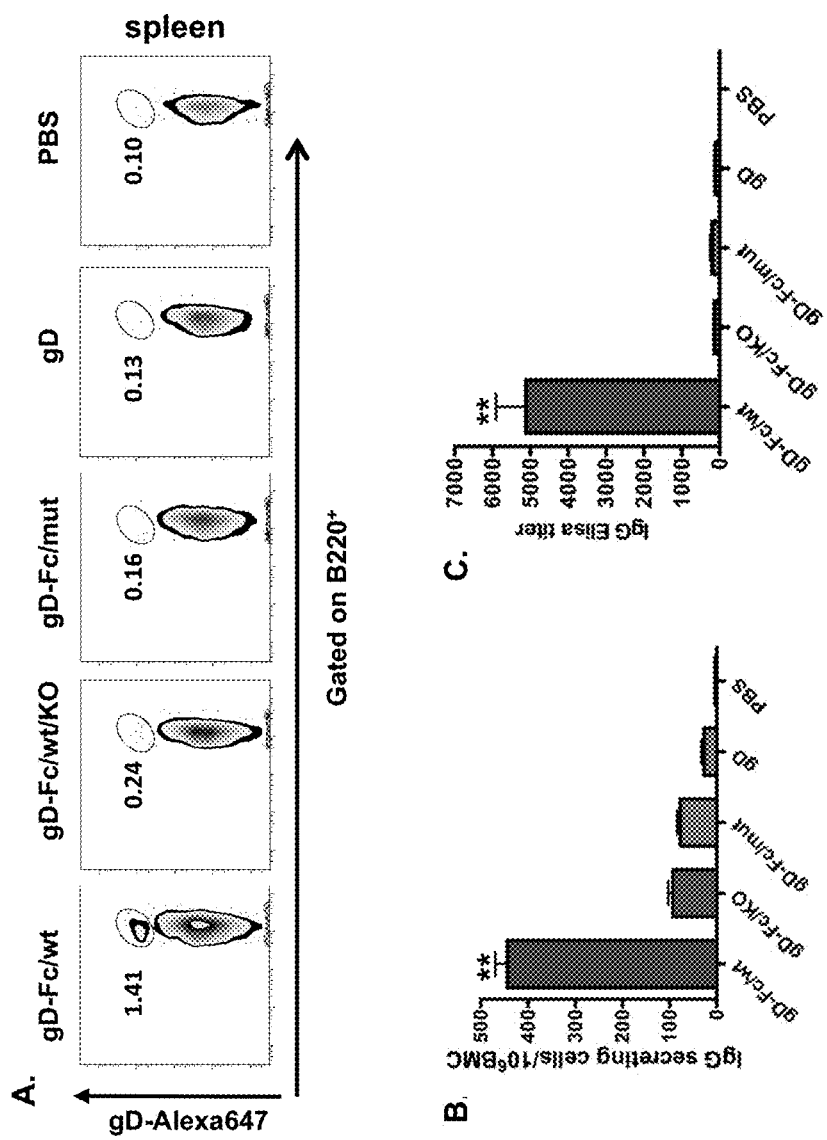
Figure 5:
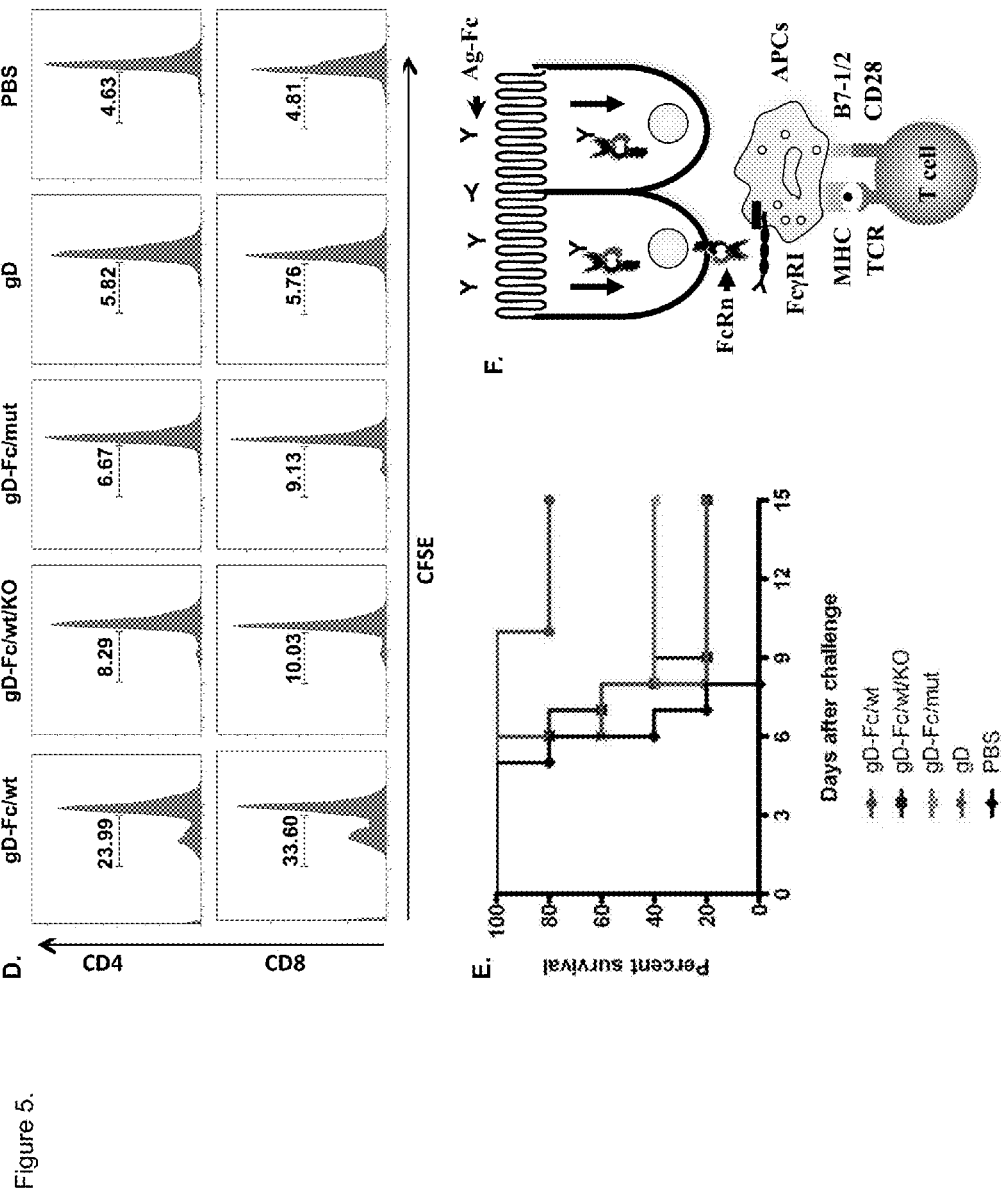

FIG. 5. Increased memory immune response in FcRn-targeted mucosal immunization.

(A). Induction of gD specific memory B cells in the spleen. The frequency of gD-specific memory B cells was assessed 6 months after the boost. Memory B cells, defined as $B220^+$ gD-surface$^+$, were analyzed 6 months after the boost by FACS. Purified gD proteins were labeled with Alexa Fluro647. Spleen cells ($2 \times 10^6$) were incubated with the 1 mg Alexa Fluro647-labeled gD proteins and B220 antibody. Numbers in the quadrants are the percentage of gD-specific memory B lymphocytes.

(B). Long-lived HSV gD-specific antibody-secreting cells in the bone marrow. Bone marrow cells removed 6 months after the boost were placed on gD-coated plates and quantified by ELISPOT analysis of IgG-secreting plasma cells. Data were pooled from two separate experiments with five mice in each experiment. The graphs were plotted based on the average ELISPOT for replicate wells. Values marked with asterisk are significantly greater (P<0.01) from the gD-Fc/wt protein-immunized mice than those of other groups as indicated.

(C). Durability of HSV-2 gD-specific serum IgG response. In two separate experiments, HSV-2 gD-specific IgG was quantified by ELISA in serum by endpoint titer from five mice at 6 months after the boost. HSV-specific IgG antibody was not detected in PBS-immunized mice.

(D). Long-lived gD specific T cell memory to FcRn-targeted mucosal vaccination. Spleen cells were isolated from the immunized mice six months after the boost, stained with CFSE, and stimulated in vitro with 20 mg/ml of purified gD for 4 days. Data are expressed in CFSE histograms of fluorescence intensity versus the number of fluorescing cells, indicating the percentage of the cell population positive for CD4 and CD8 antigen. Numbers in the quadrants are the percentage of $CD4^+$ and $CD8^+$ proliferating T cells. Representative flow cytometry profiles of two similar experiments with three mice per group are shown. Immunization conditions are displayed on the top.

(E). Mean survival following genital HSV-2 challenge six months following the boost. The immunized mice were challenged intravaginally with $1 \times 10^4$ pfu of HSV-2. Percentage of mice protected on the indicated days is calculated as the number of mice surviving divided by the number of mice in each group (n=5).

(F). Proposed model of FcRn-mediated mucosal vaccine delivery. The Fc-fused antigens are transported by FcRn and targeted to the mucosal antigen presenting cells (APCs), such as dendritic cells. Antigen is taken up by pinocytosis or FcgRI-mediated endocytosis in APCs, then processed and presented to T cells.

Figure 6:
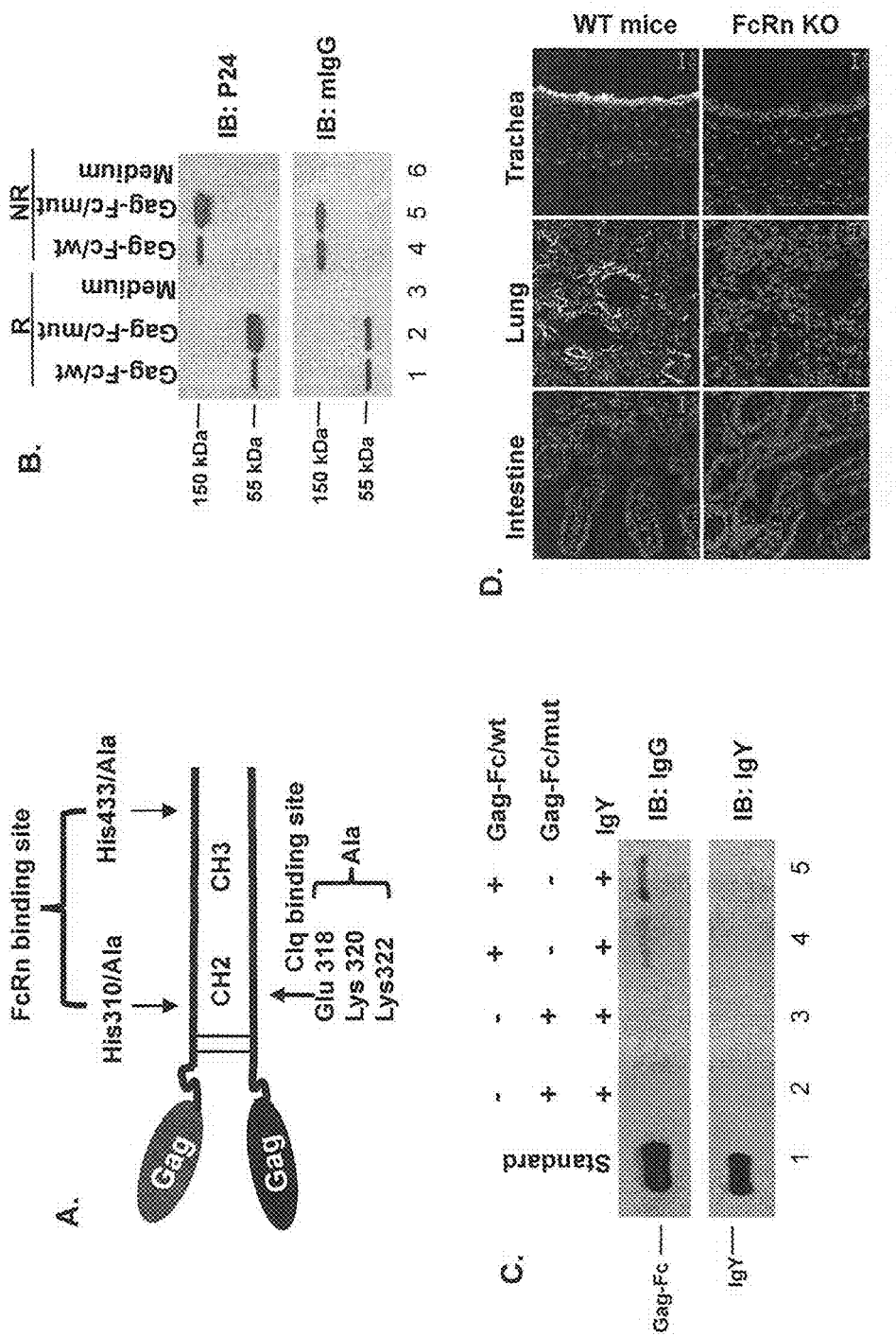
Figure 6:
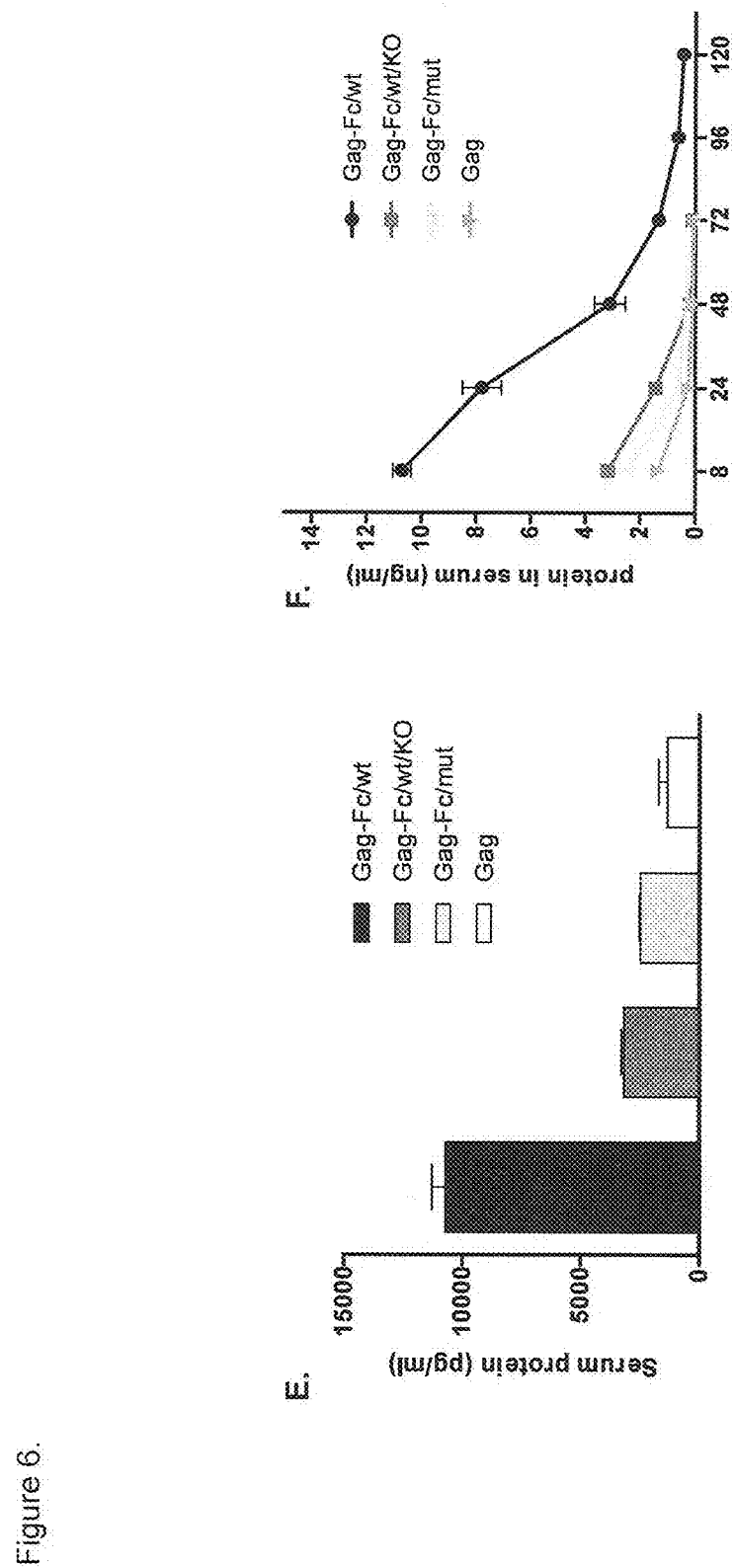

FIG. 6. Design and characterization of HIV-1 Gag fused to IgG Fc fragment and FcRn-dependent transcytosis of the Gag-Fc/wt.

(A). Schematic illustration for the genetic fusion of HIV Gag and murine Fcγ2a cDNA to create a Gag-Fc fusion gene. Mutations were made in the CH2 domain of Fcg2a fragment by using site-directed mutagenesis to replace Glu318, Lys320, and Lys322 with Ala residues to remove the complement C1q binding site, and His 310 and His 433 with Ala residues to eliminate FcRn binding sites.

(B). The Gag-Fc fusion proteins were secreted by CHO cells. The Gag-Fc was recognized by either a mAb anti-Gag (top panel) or rabbit anti-mouse IgG (bottom panel). The fusion protein appeared as a dimer under non-reducing (NR) or a monomer under reducing (R) condition.

(C). Transport of Gag-Fc/wt fusion proteins in MDCK-FcRn cell lines. MDCK-FcRn cells were plated onto 24-mm transwells and grown for 3-6 days to allow the formation of a polarized monolayer with resistance greater than 300 Ωcm$^2$. Purified Gag-Fc/wt (100 mg/ml) and chicken IgY were applied to the apical reservoir and transcytosis was allowed to proceed for 2 hr. The proteins were collected from the basolateral reservoir and blotted with anti-Gag antibody under reducing condition. The Gag-Fc/wt fusion protein (lanes 4&5, top panel), but not Gag-Fc/mut (lanes 2&3, top panel) or IgY (bottom panel), was detected by Western blot. Lane 1, representing Gag-Fc/wt or IgY protein, was used as a positive control. wt: wild-type; mut: mutant.

(D). Expression of mouse FcRn in the trachea and lung in adult mice. Frozen sections of tissue samples obtained from wt or FcRn KO mice were stained with affinity purified rabbit anti-FcRn antibody and followed by Alexa Fluro 488-conjugated IgG (green). FcRn staining was not observed in the presence of normal rabbit IgG. The nucleus is stained with DAPI (blue). The data are representative of sections from at least three independent mice. Images were originally obtained at 40× magnification. Scale bars represent 20 μm.

(E). Transport of the Gag-Fc/wt proteins across mucosal barrier. Purified, Gag, Gag-Fc/wt and Gag-Fc/mut proteins (20 mg) were intranasally inoculated into wild-type and FcRn KO mice as indicated. 8 hr later, the mouse sera were collected, the Gag or Gag-Fc protein concentration in blood circulation was measured by ELISA. Inoculation conditions are displayed. Star (**) denotes p<0.01.

(F). Persistence of the Gag-Fc/proteins in the sera. The protein concentrations in sera were measured by ELISA after the transfer at indicated time (hr).

Figure 7:
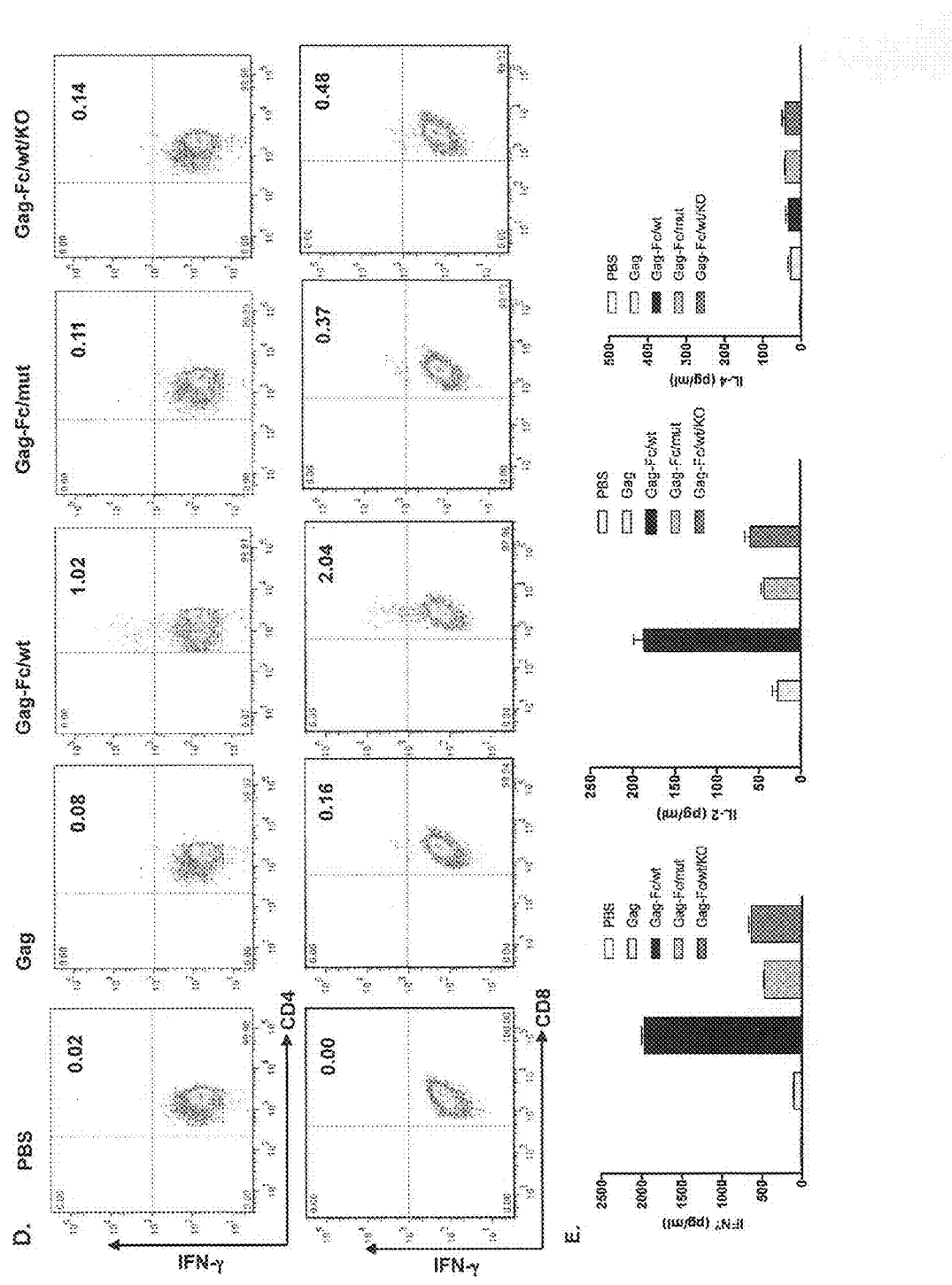

FIG. 7. FcRn-targeted mucosal vaccination induces enhanced Gag-specific antibody and T cell immune responses. 20 ug Gag-Fc/wt, Gag-Fc/mut, Gag alone with 20 ug CpG were i.n. administered into wild-type or FcRn KO mice.

(A). Measurement of anti-HIV Gag-specific IgG antibody titers in serum before and after the boost immunization. HIV Gag-specific IgG antibody at indicated days was measured in serum by ELISA. Immunization conditions are displayed at the right.

(B). Measurement of HIV Gag-specific IgG isotype titers in the serum. Blood samples were taken from mice by tail bleeding. HIV Gag-specific IgG isotype at 28 days was measured in serum by ELISA. Immunization conditions are displayed in the bottom.

(C). Detection of activated B cells in the germinal center (GC) in the immunized mice by flow cytometry. Representative flow cytometric analyses of GC B cells among B220+ B cells in the spleen 10 days after the boost. Numbers are the percentage of activated GC B cells (PNA+FAS+) among gated B220+ cells.

(D). The percentage of IFN-γ producing T cells in the spleen 7 days after the boost. Splenocytes from the immunized mice were stimulated for 18 hr with purified Gag or medium control. Lymphocytes were gated by forward and side scatter and T cells labeled with anti-CD3 and identified by their respective surface markers CD4 and CD8 and intracellular IFN-g staining. Immunization conditions are displayed on the top. Numbers in the quadrants represent the percentage of IFN-γ+ CD3+ CD4+ (top panel) or IFN-γ+ CD3+ CD8+ (bottom panel) T cells. Isotype controls included FITC-mouse-IgG1 and show baseline response.

(E). Cytokine secretions from the stimulated spleen T cells. Splenocytes were collected and pooled from three immunized mice per group on day 7 after the boost. Cells were stimulated in vitro specifically with purified Gag for 24 hr. Cytokines IFN-g, IL-2, and IL-4 in the culture supernatant were detected by ELISA. They are presented as picograms/ml of culture supernatant. Data are representative of three experiments with three mice pooled in each experiment.

Figure 8:
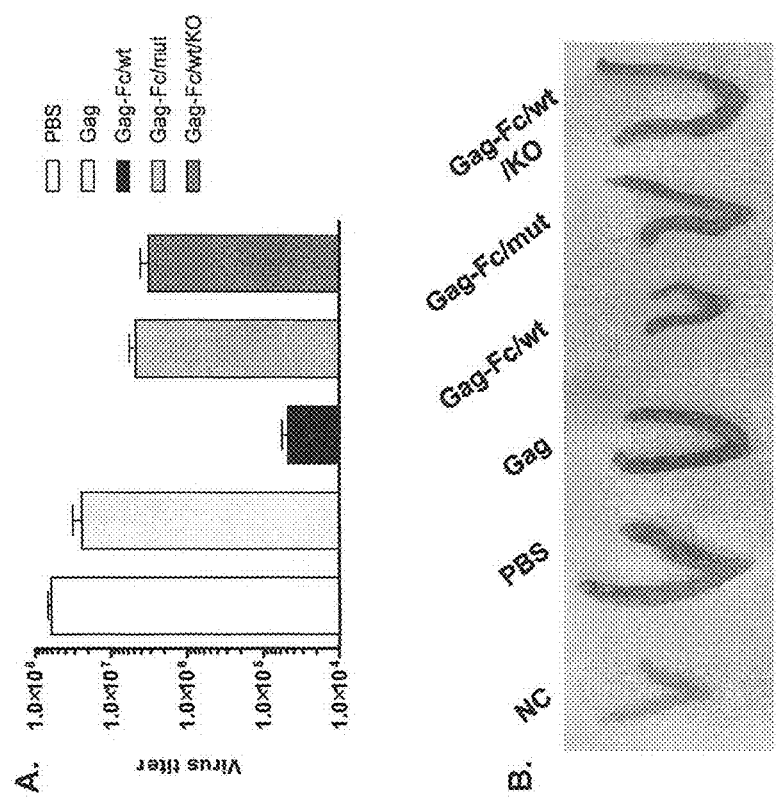

FIG. 8. FcRn-targeted mucosal immunization engenders protective immunity to intravaginal viral challenge.

(A). Mean of viral titers in ovaries following intravaginal challenge with vaccinia virus (VV) expressing HIV-1 Gag (rVV-Gag). Four weeks after the boost, groups of five mice were intravaginally challenged with $5 \times 10^7$ pfu of rVV-Gag. Mice were sacrificed 5 days after infection and paired ovaries were collected. Ovaries were homogenized and viral titers were determined by standard plaque assay on Vero cell monolayer. The data represented three similar experiments.

(B). Macroscopic pictures of uteri from normal mice or the immunized mice challenged with rVV-Gag are shown. Immunization conditions are displayed in the bottom.

Figure 9:
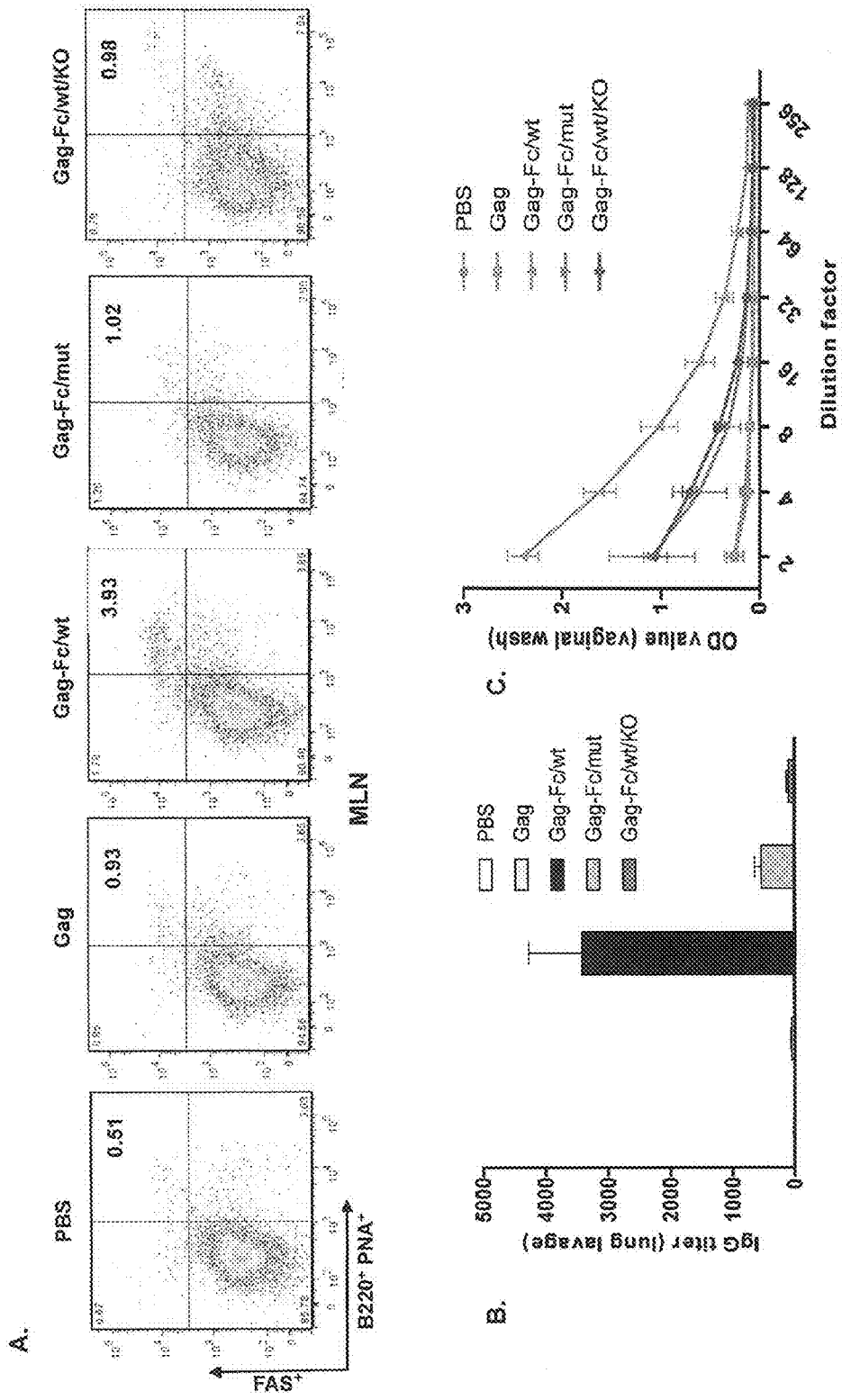
Figure 9:
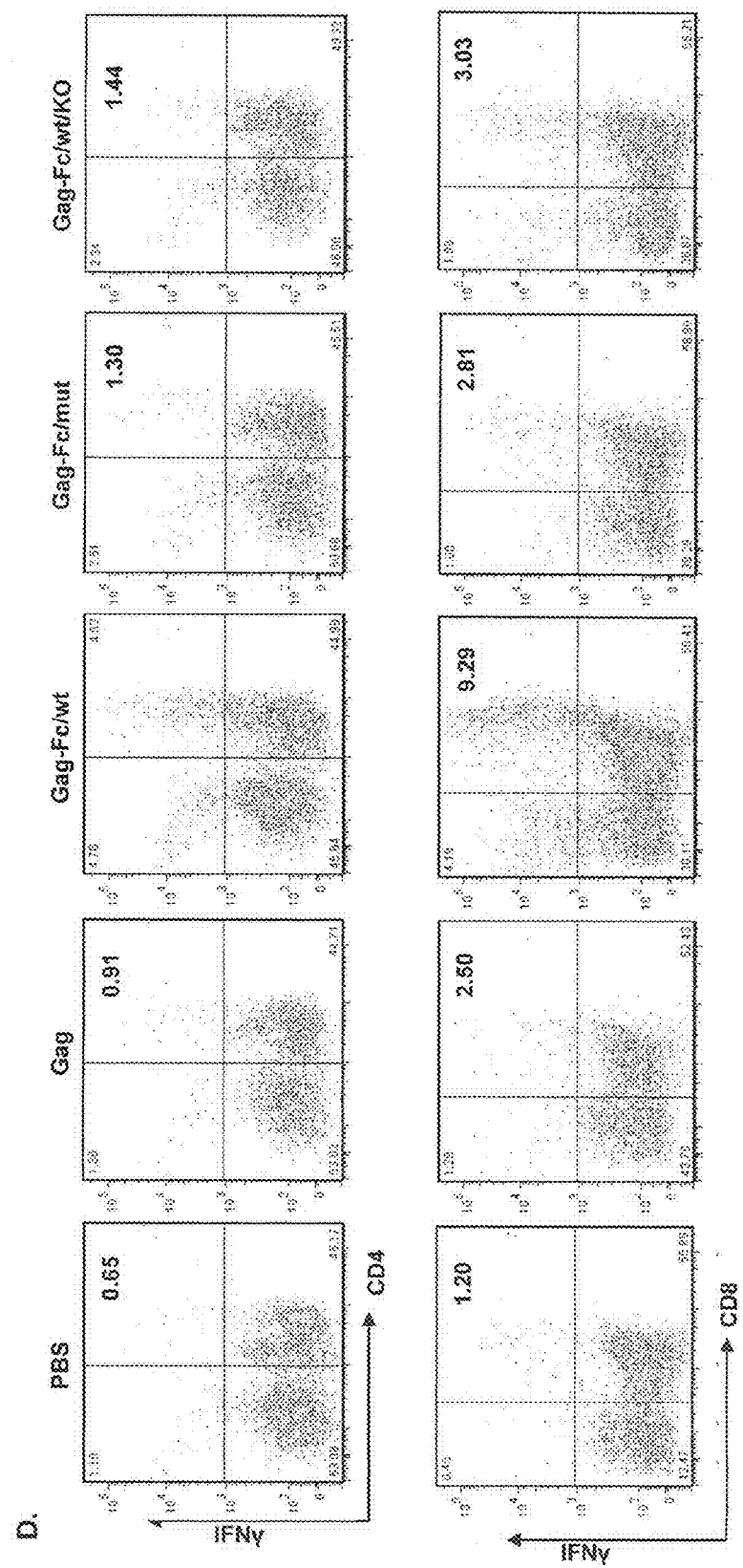

FIG. 9. Local immune responses induced by FcRn-targeted mucosal immunization.

(A). Detection of activated B cells in the germinal center (GC) in the immunized mice by flow cytometry. Representative flow cytometric analyses of GC B cells among B220+ B cells in the mediastinal lymph node (MLN) 10 days after the immunization. Numbers are the percentage of activated GC B cells (PNA+FAS+) among gated B220+ cells.

(B+C). HIV Gag-specific antibody responses in bronchial alveolar lavage (BAL) and vaginal secretions following immunization. BAL (B) and vaginal washes (C) were obtained from mice 10 days after the boost and Gag-specific IgG titers were determined by ELISA. Antibody titers for 3 mice from a representative experiment were quantified by endpoint titer. Titers of HIV Gag-specific IgG antibody from BAL and vaginal washes of naive mice always fell below the limit of detection and are omitted from the figure for clarity. The data shown are representative of three independent experiments. Asterisk (*) indicates significant difference among groups (P≤0.05).

(D). Increased presence of HIV Gag-specific T lymphocytes in the vaginal epithelia after challenge. Lymphocytes were harvested from collagenase-treated vaginal tissues 5 days after intravaginal inoculation of rVV-Gag. Intracellular staining for IFN-g expression on CD4+ and CD8+ T cells was analyzed after gating on viable CD3+ lymphocytes. The numbers in each column show the percentage of IFN-g-positive T lymphocytes from the gated CD4+ or CD8+ T cells. Isotype controls included FITC conjugated mouse-IgG1 and show baseline response. Data shown are of a representative from three experiments using 3 mice per experiment.

Figure 10:
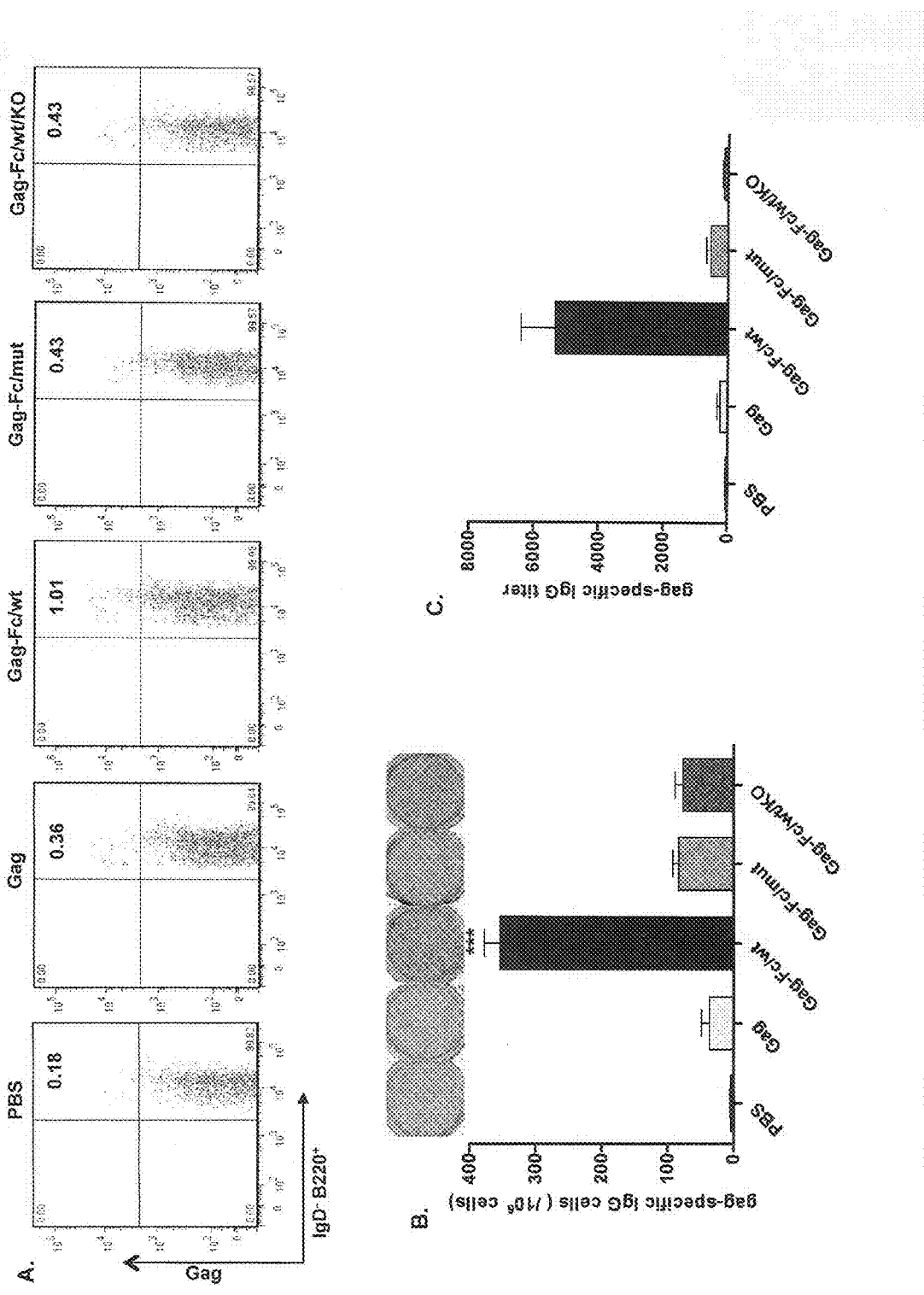
Figure 10:
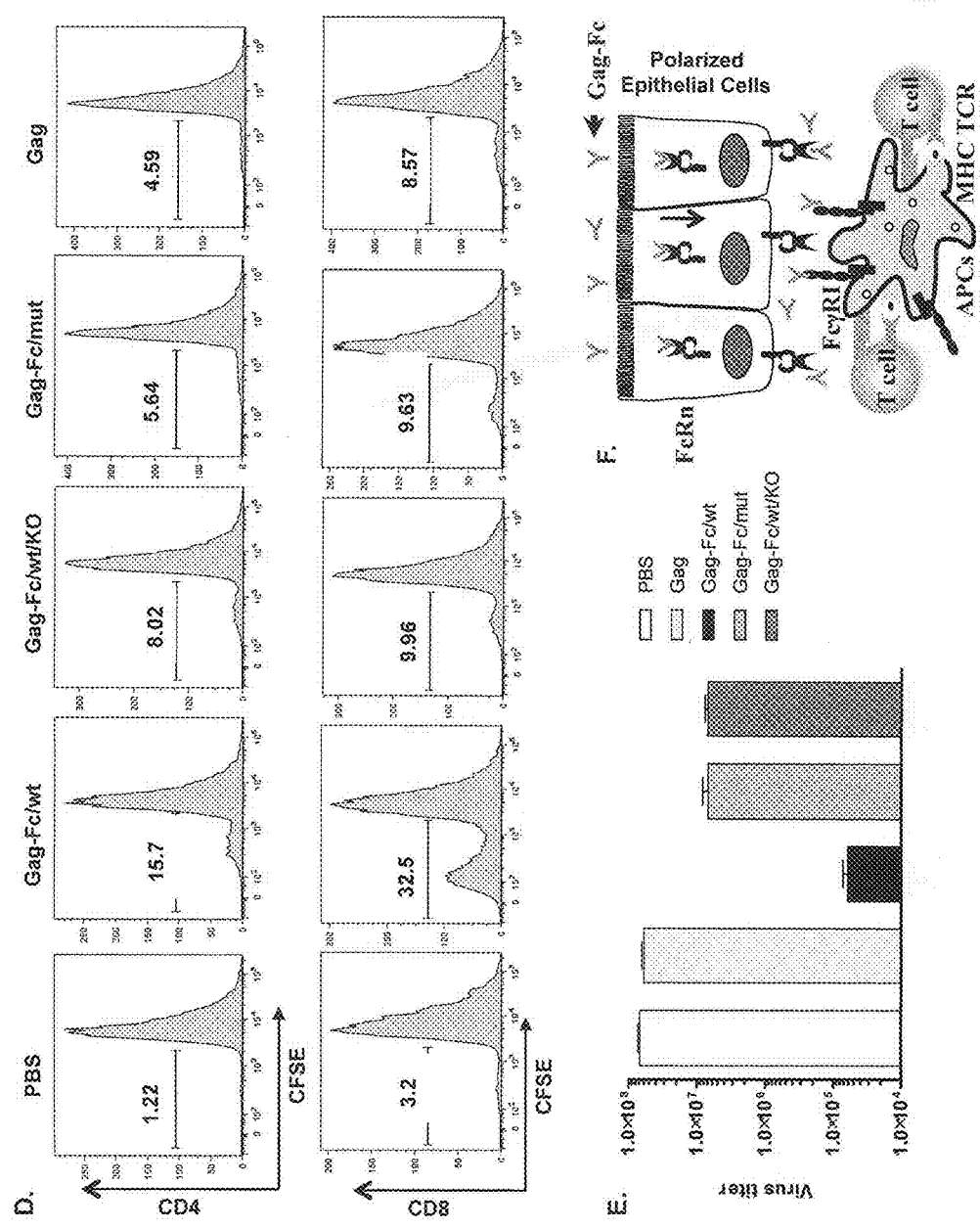

FIG. 10. Increased memory immune response in FcRn-targeted mucosal immunization.

(A). Induction of Gag specific memory B cells in the spleen. The frequency of Gag-specific memory B cells was assessed 4 months after the boost. The Gag-specific memory B cells, defined as B220+IgG+IgD−, were analyzed 4 months after the boost by FACS. Purified HIV Gag proteins were labeled with Alexa Fluro647. Splenocytes ($2 \times 10^6$) were incubated with the 1 ug Alexa Fluro647-labeled Gag proteins and B220 antibody. Numbers in the quadrants are the percentage of HIV Gag-specific memory B lymphocytes.

(B). Long-lived HIV Gag-specific antibody-secreting cells in the bone marrow. Bone marrow cells removed 4 months after the boost were placed on Gag-coated plates and quantified by ELISPOT analysis of IgG-secreting plasma cells. Data were pooled from three separate experiments with three mice in each experiment. The graphs were plotted based on the average ELISPOTs for replicate wells (top panel). Values marked with asterisk are significantly greater (P<0.01) from the Gag-Fc/wt fusion protein-immunized mice than those for other groups as indicated in the bottom.

(C). Durability of HIV Gag-specific serum IgG response. In two separate experiments, HIV Gag-specific IgG was quantified by ELISA in serum by endpoint titer from three mice at 4 months after the boost. HIV-specific IgG antibody was not detected in naive mice.

D). Long-lived HIV Gag-specific T cell memory response to FcRn-targeted mucosal vaccination. Splenocytes were isolated four months after the boost, stained with CFSE, and stimulated in vitro with 20 ug/ml of purified Gag for 4 days. Data are expressed in CFSE histograms of fluorescence intensity versus the number of fluorescing cells, indicating the percentage of the cell population positive for CD4 or CD8 antigen. Numbers in the quadrants are the percentage of CD4+ and CD8+ proliferating T cells. Data are representative flow cytometry profiles of two similar experiments with three mice per group. Immunization conditions are displayed on the top.

(E). Mean of viral titers in ovaries following vaginal challenge with rVV-Gag. Four months after the boost, groups of five mice were intravaginally challenged with $5 \times 10^7$ pfu of rVV-Gag and sacrificed 5 days after challenge. Ovaries were collected for each mouse and viral titers were measured by a plaque assay. The data represented three similar experiments.

(F). Proposed model of FcRn-mediated mucosal vaccine delivery. The Fc-fused HIV gag antigens are transported by FcRn across epithelial mucosal barrier and targeted to the mucosal antigen presenting cells (APCs), such as dendritic cells. Antigen is taken up by pinocytosis or FcgRI-mediated endocytosis in APCs, then processed and presented or cross presented to T cells. TCR: T cell receptor; APC, antigen presenting cells.

DETAILED DESCRIPTION

In the description that follows, a number of terms used in recombinant DNA and immunology are extensively utilized. In order to provide a clearer and consistent understanding of the specification and claims, including the scope to be given such terms, the following definitions are provided.

The term 'biological sample' intends a fluid or tissue of a mammalian individual (e.g. an anthropoid, a human), reptilian, avian, or any other zoo or farm animal that commonly contains antibodies produced by the individual. Such components are known in the art and include, without limitation, blood, plasma, serum, urine, spinal fluid, lymph fluid, secretions of the respiratory, intestinal or genitourinary tracts, tears, saliva, milk, white blood cells and myelomas. Body components include biological liquids. The term 'biological fluid' refers to a fluid obtained from an organism. Some biological fluids are used as a source of other products, such as clotting factors (e.g. Factor VIII), serum albumin, growth hormone and the like.

The term 'immunologically reactive' means that the antigen in question will react specifically with antibodies present in a body component from an infected individual.

The term 'immune complex' intends the combination formed when an antibody binds to an antigen.

The term 'purified' as applied to proteins herein refers to a composition wherein the desired protein comprises at least 35% of the total protein component in the composition. The desired protein preferably comprises at least 40%, more preferably at least about 50%, more preferably at least about 60%, still more preferably at least about 70%, even more preferably at least about 80%, even more preferably at least about 90%, and most preferably at least about 95% of the total protein component. The composition may contain other compounds such as carbohydrates, salts, lipids, solvents, and the like, without affecting the determination of the percentage purity as used herein. An 'isolated' Fc-antigen fusion protein intends a fusion protein composition that is at least 35% pure.

The term 'recombinantly expressed' used within the context of the present invention refers to the fact that the proteins of the present invention are produced by recombinant expression methods be it in prokaryotes, or lower or higher eukaryotes as discussed in detail below.

The term 'lower eukaryote' refers to host cells such as yeast, fungi and the like. Lower eukaryotes are generally (but not necessarily) unicellular. Preferred lower eukaryotes are yeasts, particularly species within *Saccharomyces. Schizosaccharomyces, Kluveromyces, Pichia* (e.g. *Pichia pastoris*), *Hansenula* (e.g. *Hansenula polymorpha, Yarowia, Schwaniomyces, Schizosaccharomyces, Zygosaccharomyces* and the like. *Saccharomyces cerevisiae, S. carlsberoensis* and *K. lactis* are the most commonly used yeast hosts, and are convenient fungal hosts.

The term 'prokaryotes' refers to hosts such as *E. coli, Lactobacillus, Lactococcus, Salmonella, Streptococcus, Bacillus subtilis* or *Streptomyces*. Also these hosts are contemplated within the present invention.

The term 'higher eukaryote' refers to host cells derived from higher animals, such as mammals, reptiles, insects, and the like. Presently preferred higher eukaryote host cells are derived from Chinese hamster (e.g. CHO), monkey (e.g. COS and Vero cells), baby hamster kidney (BHK), pig kidney (PK15), rabbit kidney 13 cells (RK13), the human osteosarcoma cell line 143 B, the human cell line HeLa and human hepatoma cell lines like Hep G2, and insect cell lines (e.g. *Spodoptera frugiperda*). The host cells may be provided in suspension or flask cultures, tissue cultures, organ cultures and the like. Alternatively the host cells may also be transgenic animals.

The term 'polypeptide' refers to a polymer of amino acids and does not refer to a specific length of the product; thus, peptides, oligopeptides, and proteins are included within the definition of polypeptide. This term also does not refer to or exclude post-expression modifications of the polypeptide, for example, glycosylations, acetylations, phosphorylations and the like. Included within the definition are, for example, polypeptides containing one or more analogues of an amino acid (including, for example, unnatural amino acids, PNA, etc.), polypeptides with substituted linkages, as well as other modifications known in the art, both naturally occurring and non-naturally occurring.

The term 'recombinant polynucleotide or nucleic acid' intends a polynucleotide or nucleic acid of genomic, cDNA, semisynthetic, or synthetic origin which, by virtue of its origin or manipulation: (1) is not associated with all or a portion of a polynucleotide with which it is associated in nature, (2) is linked to a polynucleotide other than that to which it is linked in nature, or (3) does not occur in nature.

The term 'recombinant host cells', 'host cells', 'cells', 'cell lines', 'cell cultures', and other such terms denoting microorganisms or higher eukaryotic cell lines cultured as unicellular entities refer to cells which can be or have been, used as recipients for a recombinant vector or other transfer polynucleotide, and include the progeny of the original cell which has been transfected. It is understood that the progeny of a single parental cell may not necessarily be completely identical in morphology or in genomic or total DNA complement as the original parent, due to natural, accidental, or deliberate mutation.

The term 'replicon' is any genetic element, e.g., a plasmid, a chromosome, a virus, a cosmid, etc., that behaves as an autonomous unit of polynucleotide replication within a cell; i.e., capable of replication under its own control.

The term 'vector' is a replicon further comprising sequences providing replication and/or expression of a desired open reading frame.

The term 'control sequence' refers to polynucleotide sequences which are necessary to effect the expression of coding sequences to which they are ligated. The nature of such control sequences differs depending upon the host organism; in prokaryotes, such control sequences generally include promoter, ribosomal binding site, and terminators; in eukaryotes, generally, such control sequences include promoters, terminators and, in some instances, enhancers. The term 'control sequences' is intended to include, at a minimum, all components whose presence is necessary for expression, and may also include additional components whose presence is advantageous, for example, leader sequences which govern secretion.

The term 'promoter' is a nucleotide sequence which is comprised of consensus sequences which allow the binding of RNA polymerase to the DNA template in a manner such that mRNA production initiates at the normal transcription initiation site for the adjacent structural gene.

The expression 'operably linked' refers to a juxtaposition wherein the components so described are in a relationship permitting them to function in their intended manner. A control sequence 'operably linked' to a coding sequence is ligated in such a way that expression of the coding sequence is achieved under conditions compatible with the control sequences.

An 'open reading frame' (ORF) is a region of a polynucleotide sequence which encodes a polypeptide and does not contain stop codons; this region may represent a portion of a coding sequence or a total coding sequence.

A 'coding sequence' is a polynucleotide sequence which is transcribed into mRNA and/or translated into a polypeptide when placed under the control of appropriate regulatory sequences. The boundaries of the coding sequence are determined by a translation start codon at the 5'-terminus and a translation stop codon at the 3'-terminus. A coding sequence can include but is not limited to mRNA, DNA (including cDNA), and recombinant polynucleotide sequences.

The term 'immunogenic' refers to the ability of a substance to cause a humoral and/or cellular response, whether alone or when linked to a carrier, in the presence or absence of an adjuvant. 'Neutralization' refers to an immune response that blocks the infectivity, either partially or fully, of an infectious agent. A 'vaccine' is an immunogenic composition capable of eliciting protection against disease, whether partial or complete. A vaccine may also be useful for treatment of an infected individual, in which case it is called a therapeutic vaccine.

The term 'therapeutic' refers to a composition capable of treating a disease or infection. The term 'effective amount' for a therapeutic or prophylactic treatment refers to an amount of epitope-bearing polypeptide sufficient to induce an immunogenic response in the individual to which it is administered, or to otherwise detectably immunoreact in its intended system (e.g., immunoassay). Preferably, the effective amount is sufficient to effect treatment, as defined above. The exact amount necessary will vary according to the application. For vaccine applications or for the generation of polyclonal antiserum/antibodies, for example, the effective amount may vary depending on the species, age, and general condition of the individual, the severity of the condition being treated, the particular polypeptide selected and its mode of administration, etc. It is also believed that effective amounts will be found within a relatively large, non-critical range. An appropriate effective amount can be readily determined using only routine experimentation. Preferred ranges of for prophylaxis of disease are about 0.01 to 1000 ug/dose, more preferably about 0.1 to 100 ug/dose, most preferably about 10-50 ug/dose. Several doses may be needed per individual in order to achieve a sufficient immune response and subsequent protection against disease.

More particularly, the enhanced delivery methods and compositions of the present invention provide for effective mucosal delivery of an Fc-antigen vaccine for prevention or treatment of disease or infection in mammalian subjects.

The invention is useful whenever it is desirable to deliver an antigen across an epithelial barrier to the immune system. The invention thus may be used to deliver antigens across intestinal epithelial tissue, lung epithelial tissue and other mucosal surfaces including nasal surfaces, vaginal surfaces, and colon surfaces. The invention may be used to induce in a subject an immune response by stimulating a humoral antibody response against an antigen, or by stimulating T cell activity. As used herein, subject means: humans, primates, horses, cows, sheep, pigs, goats, dogs, cats, chickens and rodents.

The invention involves the formation of a fusion protein comprising the Fc-fragment of an IgG and an antigen. A fusion protein is a polypeptide resulting from the expression of a hybrid DNA, the hybrid DNA created by fusing two or more nucleic acids encoding two or more proteins or peptides. The region of the Fc-fragment of IgG that binds to the FcRn receptor in humans has been described based upon X-ray crystallography (Burmaister, W. P. et al., Nature, 1994; 372:379-378.) The major contact area of Fc with the FcRn receptor is near the junction of the $C_{H2}$ and $C_{H3}$ domains. Potential contacts are residues 248, 250-257, 272, 285, 288, 290-291, 308-311 and 314 in $C_{H2}$ and 385-387, 428 and 433-436 in $C_{H3}$. The foregoing Fc-FcRn contacts are all within a single Ig heavy chain. Within the scope of the invention are nucleotide sequences encoding human Fc.

It has been noted previously that two FcRn receptors can bind a single Fc molecule. The crystallographic data suggest that in such a complex, each FcRn molecule binds a single polypeptide of the Fc homodimer. Therefore, in another aspect, a Fc heterodimer is provided wherein each arm of the Fc molecule is fused to a different antigen, whether the antigens are for the same disease or for different diseases. Alternatively, one Fc arm is fused to a desired antigen and the other Fc arm is fused to an adjuvant of interest. It is understood that variations on antigens, such as, among others, chimeric antigens produced from fusing two or more immunogenic epitopes from two or more antigens into one fusion protein, then fused to Fc, are within the skill of a person in the art.

The Fc-fragment should be chosen from an immunoglobulin known to bind the FcRn in the mucosa of the subject receiving the antigen-Fc vaccine. Immunoglobulin subclasses recognized by FcRn in different epithelial mucosa of animal subjects are known to a person in the art and can be found in Ober, R. J. et al, 2001, Int. Immunol. 13, 1551-9.

In accordance with the present invention, the Fc-antigen fusion protein may be produced by recombinant genetic engineering techniques known in the art, for example, DNA ligation, or PCR-based gene assembly as described in the Examples below. Other methods known in the art can be used.

Given the foregoing information, those of ordinary skill in the art will readily recognize that the Fc region of IgG can be modified according to well-recognized procedures such as site-directed mutagenesis and the like to yield modified IgG or modified Fc fragments or portions thereof that will be bound by the FcRn receptor. Such modifications include modifications remote from the FcRn contact sites as well as modifications within the contact sites that preserve or even enhance binding. If the Fc-antigen fusion protein is composed entirely of gene-encoded amino acids, or a portion of it is so composed, the fusion protein or the relevant portion may also be synthesized using conventional recombinant genetic engineering techniques.

For recombinant production, established methods (Sambrook et al., Molecular Cloning: A Laboratory Manual. Cold Spring Harbor Press, Cold Spring Harbor, N.Y. 1989) would be used to engineer DNA encoding a fusion protein comprised of the antigenic peptide or protein and a Fc. This DNA would be placed in an expression vector and introduced into bacterial or eukaryotic cells by established methods. The fusion protein would be purified from the cells or from the culture medium by established methods. Methods for recombinant protein and peptide production are well known in the art (see, e.g., Maniatis et al., 1989, Molecular Cloning A Laboratory Manual, Cold Spring Harbor Laboratory, N.Y.; and Ausubel et al., 1989, Current Protocols in Molecular Biology, Greene Publishing Associates and Wiley Interscience, N.Y.).

In accordance with the present invention, an Fc may be fused to a peptide or protein derivative such as those listed herein including, but not limited to, antigens, allergens, pathogens or to other proteins or protein derivatives of potential therapeutic interest such as growth factors, colony stimulating factors, growth inhibitory factors, signaling molecules, hormones, steroids, neurotransmitters, or morphogens that would be of use when delivered across an epithelial barrier.

Included within the definition of biologically active peptides and proteins, or antigens for use within the invention are natural or synthetic, therapeutically or prophylactically active, peptides (comprised of two or more covalently linked amino acids), proteins, peptide or protein fragments, peptide or protein analogs, and chemically modified derivatives or salts of active peptides or proteins.

An antigen as used herein falls into four classes: 1) antigens that are characteristic of a pathogen; 2) antigens that are characteristic of an autoimmune disease; 3) antigens that are characteristic of an allergen; and 4) antigens that are characteristic of a tumor. Antigens in general include polysaccharides, glycolipids, glycoproteins, peptides, proteins, carbohydrates and lipids from cell surfaces, cytoplasm, nuclei, mitochondria and the like.

Antigens that are characteristic of pathogens include antigens derived from viruses, bacteria, parasites or fungi. Examples of important pathogens include vibrio choleras, enterotoxigenic *Escherichia coli*, rotavirus, *Clostridium difficile*, *Shigella* species, *Salmonella typhi*, parainfluenza virus, influenza virus, *Streptococcus pneumonias*, *Borella burgdorferi*, HIV, *Streptococcus mutans*, *Plasmodium falciparum*, *Staphylococcus aureus*, rabies virus, Epstein-Barr virus, and herpes simplex virus. Specific antigens are known to those of skill in the art, for example, influenza HA, NA, M2, HIV gp120, *mycobacterium tuberculosis* Ag85B and ESAT6, *Streptococcus pneumonia* PspA, PsaA, and CbpA, respiratory syncytial virus (RSV) F and G protein, human papilloma virus protein, to name a few.

Viruses in general include but are not limited to those in the following families: picornaviridae; caliciviridae; togaviridae; flaviviridae; coronaviridae; rhabdoviridae; filoviridae; paramyxoviridae; orthomyxoviridae; bunyaviridae; arenaviridae; reoviridae; retroviridae; hepadnaviridae; parvoviridae; papovaviridae; adenoviridae; herpesviridae; and poxyviridae.

Bacteria in general include but are not limited to: *P. aeruginosa; E. coli, Klebsiella* sp.; *Serratia* sp.; *Pseudomanas* sp.; *P. cepacia; Acinetobacter* sp.; *S. epidermis; E. faecalis; S. pneumonias; S. aureus; Haemophilus* sp.; *Neisseria* Sp.; *N. meningitidis; Bacteroides* sp.; *Citrobacter* sp.; *Branhamella* sp.; *Salmonelia* sp.; *Shigella* sp.; *S. pyogenes; Proteus* sp.; *Clostridium* sp.; *Erysipelothrix* sp.; *Lesteria* sp.; *Pasteurella multocida; Streptobacillus* sp.; *Spirillum* sp.; *Fusospirocheta* sp.; *Treponema pallidum; Borrelia* sp.; *Actinomycetes; Mycoplasma* sp.; *Chlamydia* sp.; *Rickettsia* sp.; *Spirochaeta; Legionella* sp.; *Mycobacteria* sp.; *Ureaplasma* sp.; *Streptomyces* sp.; *Trichomoras* sp.; and *P. mirabilis*.

Parasites include but are not limited to: *Plasmodium falciparum, P. vivax, P. ovale, P. malaria; Toxoplasma gondii; Leishmania mexicana, L. tropica, L. major, L. aethiopica, L. donovani, Trypanosoma cruzi, T. brucei, Schistosoma mansoni, S. haematobium, S. japonium; Trichinella spiralis; Wuchereria bancrofti; Brugia malayli; Entamoeba histolytica; Enterobius vermiculoarus; Taenia solium, T. saginata, Trichomonas vaginatis, T. hominis, T. tenax; Giardia lamblia; Cryptosporidium parvum; Pneumocytis carinii, Babesia bovis, B. divergens, B. microti, Isospore belli, L hominis; Dientamoeba fragiles; Onchocerca volvulus; Ascaris lumbricoides, Necator americanis; Ancylostoma duodenale; Strongyloides stercoralis; Capillaria philippinensis; Angiostrongylus cantonensis; Hymenolepis nana; Diphyllobothrium latum; Echinococcus granulosus, E. multilocularis; Paragonimus westermani, P. caliensis; Chlonorchis sinensis; Opisthorchis felineas, G. Viverini, Fasciola hepatica Sarcoptes scabiei, Pediculus humanus; Phthirius pubis;* and *Dermatobia hominis*.

Fungi in general include but are not limited to: *Cryptococcus neoformans; Blastomyces dermatitidis; Aiellomyces dermatitidis; Histoplasfria capsulatum; Coccidioides immitis; Candids* species, including *C. albicans, C. tropicalis, C. parapsilosis, C. guilliermondii* and *C. krusei, Aspergillus* species, including *A. fumigatus, A. flavus* and *A. niger, Rhizopus* species; *Rhizomucor* species; *Cunninghammella* species; *Apophysomyces* species, including *A. saksenaea, A. mucor* and *A. absidia; Sporothrix schenckii, Paracoccidioides brasiliensis; Pseudallescheria boydii, Torulopsis glabrata;* and *Dermatophyres* species.

Antigens that are characteristic of autoimmune disease typically will be derived from the cell surface, cytoplasm, nucleus, mitochondria and the like of mammalian tissues. Examples include antigens characteristic of uveitis (e.g. S antigen), diabetes mellitus, multiple sclerosis, systemic lupus erythematosus, Hashimoto's thyroiditis, myasthenia gravis, primary myxoedema, thyrotoxicosis, rheumatoid arthritis, pernicious anemia, Addison's disease, scleroderma, autoimmune atrophic gastritis, premature menopause (few cases), male infertility (few cases), juvenile diabetes, Goodpasture's syndrome, pemphigus vulgaris, pemphigoid, sympathetic opthalmia, phacogenic uveitis, autoimmune haemolytic anemia, idiopathic thrombocylopenic purpura, idiopathic feucopenia, primary biliary cirrhosis (few cases), ulcerative colitis, Siogren's syndrome, Wegener's granulomatosis, poly/dermatomyositis, and discold lupus erythromatosus.

Antigens that are allergens are generally proteins or glycoproteins, although allergens may also be low molecular weight allergenic haptens that induce allergy after covalently combining with a protein carrier (Remington's Pharmaceutical Sciences). Allergens include antigens derived from pollens, dust, molds, spores, dander, insects and foods. Specific examples include. the urushiols (pentadecylcatechol or heptadecyicatechol) of *Toxicodendron* species such as poison ivy, poison oak and poison sumac, and the sesquiterpenoid lactones of ragweed and related plants.

Antigens that are characteristic of tumor antigens typically will be derived from the cell surface, cytoplasm, nucleus, organelles and the like of cells of tumor tissue. Examples include antigens characteristic of tumor proteins, including proteins encoded by mutated oncogenes; viral proteins associated with tumors; and tumor mucins and glycolipids. Tumors include, but are not limited to, those from the following sites of cancer and types of cancer: lip, nasopharynx, pharynx and oral cavity, esophagus, stomach, colon, rectum, liver, gall bladder, binary tree, pancreas, larynx, lung and bronchus, melanoma of skin, breast, cervix, uteri, uterus, ovary, bladder, kidney, brain and other parts of the nervous system, thyroid, prostate, testes, Hodgkin's disease, non-Hodgkin's lymphoma, multiple myeloma and leukemia. Viral proteins associated with tumors would be those from the classes of viruses noted above. Antigens characteristic of tumors may be proteins not usually expressed by a tumor precursor cell, or may be a protein which is normally expressed in a tumor precursor cell, but having a mutation characteristic of a tumor. An antigen characteristic of a tumor may be a mutant variant of the normal protein-having an altered activity or subcellular distribution. Mutations of genes giving rise to tumor antigens, in addition to those specified above, may be in the coding region, 5' or 3' noncoding regions, or introns of a gene, and may be the result of point mutations frameshifts, deletions, additions, duplications, chromosomal rearrangements and the like. One of ordinary skill in the art is familiar with the broad variety of alterations to normal gene structure and expression which gives rise to tumor antigens. Specific examples of tumor antigens include: proteins such as Ig-idiotype of B cell lymphoma, mutant cyclin-dependent kinase 4 of melanoma, Pmel-17 (gp 100) of melanoma, MART-1 (Melan-A) of melanoma, p15 protein of melanoma, tyrosinase of melanoma, MAGE 1, 2 and 3 of melanoma, thyroid medullary, small cell lung cancer, colon and/or bronchial squamous cell cancer, BAGE of bladder, melanoma, breast, and squamous-cell carcinoma, gp75 of melanoma, oncofetal antigen of melanoma; carbohydrate/lipids such as muci mucin of breast, pancreas, and ovarian cancer, GM2 and GD2 gangliosides of melanoma; oncogenes such as mutant p53 of carcinoma, mutant ras of colon cancer and HER21neu proto-onco-gene of breast carcinoma; viral products such as human papilloma virus proteins of squamous cell cancers of cervix and esophagus. It is also contemplated that proteinaceous tumor antigens may be presented by HLA molecules as specific peptides derived from the whole protein. Metabolic processing of proteins to yield antigenic peptides is well known in the art; for example see U.S. Pat. No. 5,342,774 (Boon et al.). The present method thus encompasses delivery of antigenic peptides and such peptides in a larger polypeptide or whole protein which give rise to antigenic peptides.

Generally, subjects can receive an effective amount of the tumor antigen, and/or peptide derived therefrom by one or more of the methods detailed below. Initial doses can be followed by booster doses, following immunization protocols standard in the art. Delivery of tumor antigens thus may stimulate proliferation of cytolytic T lymphocytes.

In one embodiment, fusion proteins of the present invention are constructed in which the fusion consists of an Fc fragment (starting with the amino acids E-P-R-G at the N-terminus of the hinge region, including the CH2 regions, and continuing through the T-P-G-K sequence in CH3 region) fused to one of the above listed proteins.

When administered, the Fc-antigen fusion peptides of the present invention are administered in pharmaceutically acceptable preparations. Such preparations may routinely contain pharmaceutically acceptable concentrations of salt, buffering agents, preservatives, compatible carriers, supplementary immune potentiating agents such as adjuvants and cytokines, and optionally other therapeutic agents.

The Fc-antigen fusion peptides of the invention may be administered in a purified form or in the form of a pharmaceutically acceptable salt. When used in medicine the salts should be pharmaceutically acceptable, but non-pharmaceutically acceptable salts may conveniently be used to prepare pharmaceutically acceptable salts thereof and are not excluded from the scope of the invention. Such pharmaceutically acceptable salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, pharmaceutically acceptable salts can be prepared as alkyline metal or alkyline earth salts, such as sodium, potassium or calcium salts of the carboxylic acid group.

Suitable buffering agents include: acetic acid and salt (1-2% W/V); citric acid and a salt (1-3% W/V); boric acid and a salt (0.5-2:5,% WN); sodium bicarbonate (0.5-1.0% W/V); and phosphoric acid and a salt (0.8-2% W/V). Suitable preservatives include benzalkonium chloride (0.003-0.03% W/V); chlotubutanol (0.3-0.9% W/V); parabens (0.01-0.25% W/V) and thimerosal (0.004-0.02% W/V).

The term "carrier" as used herein, and described more fully below, means one or more solid or liquid filler, dilutants or encapsulating substances which are suitable for administration to a human or other mammal. The "carrier" may be an organic or inorganic ingredient, natural or synthetic, with which the active ingredient is combined to facilitate administration.

The components of the pharmaceutical compositions are capable of being commingled with the Fc-antigen fusion protein of the present invention, and with each other, in a manner such that there is no interaction which would substantially impair the desired pharmaceutical efficacy. The components of oral drug formulations include diluents, binders, lubricants, glidants, disintegrants, coloring agents and flavoring agents.

Encapsulating substances for the preparation of enteric-coated oral formulations include cellulose acetate phthalate, polyvinyl acetate phthalate, hydroxypropyl methylcellulose phthalate and methacrylic acid ester copolymers. Solid oral formulations such as capsules or tablets are preferred. Elixirs and syrups also are well known oral formulations. The components of aerosol formulations include solubilized active ingredients, antioxidants, solvent blends and propellants for solution formulations, and micronized and suspended active ingredients, dispersing agents and propellants for suspension formulations. The oral, aerosol and nasal formulations of the invention can be distinguished from injectable preparations of the prior art because such formulations may be nonaseptic, whereas injectable preparations must be aseptic.

The term "adjuvant" is intended to include any substance which is incorporated into or administered simultaneously with the fusion protein of the invention and which nonspecifically potentiates the immune response in the subject. Adjuvants include aluminum compounds, e.g., gels, aluminum hydroxide and aluminum phosphate, and Freund's complete or incomplete adjuvant (in which the fusion protein is incorporated in the aqueous phase of a stabilized water in paraffin oil emulsion). The paraffin oil may be replaced with different types of oils, e.g., squalene or peanut oil. Other materials with adjuvant properties include, flagellin, BCG (attenuated *Mycobacterium tuberculosis*), calcium phosphate, levamisole, isoprinosine, polyanions (e.g., poly A:U) leutinan, pertussis toxin, cholera toxin, lipid A, saponins and peptides, e.g. muramyl dipeptide. dimethyl dioctadecyl-ammonium bromide (DDA); monophosphoryl lipid A (MPL); LTK63, lipophilic quaternary ammonium salt-DDA, Trehalose dimycolate and synthetic derivatives, DDA-MPL, DDA-TDM, DDA-TDB, IC-31, aluminum salts, aluminum hydroxyide, aluminum phosphate, potassium aluminum phosphate, Montanide ISA-51, ISA-720, microparticles, immunostimulatory complexes, liposomes, virosomes, virus-like particles, CpG oligonucleotides, cholera toxin, heat-labile toxin from *E. coli*, lipoproteins, dendritic cells, IL-12, GM-CSF, nanoparticles including calcium phosphate nanoparticles, combination of soybean oil, emulsifying agents, and ethanol to form a nanoemulsion; AS04, ZADAXIN, or combinations thereof. Rare earth salts, e.g., lanthanum and cerium, may also be used as adjuvants. The amount of adjuvants depends on the subject and the particular fusion protein used and can be readily determined by one skilled in the art without undue experimentation.

In a preferred embodiment of the invention, the adjuvant is immunostimulatory oligonucleotides containing unmethylated CpG dinucleotides ("CpG"). CpGs are known in the art as being adjuvants when administered by both systemic and mucosal routes (WO 96/02555, EP 468520, Davis et al., J. Immunol, 1998, 160(2): 870-876, McCluskie and Davis, J. Immunol., 1998, 161(9): 4463-6). CpG is an abbreviation for cytosineguanosinc dinucicotide motifs present in DNA. Historically, it was observed that the DNA fraction of BCG could exert an anti-tumour effect. In further studies, synthetic oligonucleotides derived from BCG gene sequences were shown to be capable of inducing immunostimulatory effects (both in vitro and in vivo). The authors of these studies concluded that certain palindromic sequences, including a central CG motif, carried this activity. The central role of the CG motif in immunostimulation was later elucidated in a publication by Krieg, 1995, Nature 374, p. 546. Detailed analysis has shown that the CG motif has to be in a certain sequence context, and that such sequences are common in bacterial DNA but are rare in vertebrate DNA. The immunostimulatory sequence is often: Purine, Purine, C, G, pyrimidine, pyrimidine; wherein the dinucleotide CG motif is not methylated, but other unmethylated CpG sequences are known to be immunostimulatory and may be used in the present invention.

CpG when formulated into vaccines, is generally administered in free solution together with free antigen (WO 96/02555; McCluskie and Davis, supra) or covalently conjugated to an antigen (PCT Publication No. WO 98/16247), or formulated with a carrier such as aluminium hydroxide ((Hepatitis surface antigen) Davis et al. supra; Brazolot-Millan et al., Proc. Natl. Acad. Sci., USA, 1998, 95(26), 15553-8).

Other supplementary immune potentiating agents, such as cytokines, may be delivered in conjunction with the Fc-antigen fusion peptides of the invention. The cytokines contemplated are those that will enhance the beneficial effects that result from administering the immunomodulators according to the invention. Cytokines are factors that support the growth and maturation of cells, including lymphocytes. It is believed that the addition of cytokines will augment cytokine activity stimulated in vivo by carrying out the methods of the invention. The preferred cytokines are interleukin (IL)-1, IL-2, gamma-interferon and tumor necrosis factor α. Other useful cytokines are believed to be IL-3, IL-4, IL-5, IL-6, IL-7, IL-8, IL-9, IL-10, IL-11, IL-12, IL-13, erythropoietin, leukemia inhibitory factor, oncostatin-M, ciliary neurotrophic factor, growth hormone, prolactin, CD40-ligand, CD27-ligand, CD30-ligand, alpha-interferon, beta-interferon, and tumor necrosis factor β. Other cytokines known to modulate T-cell activity in a manner likely to be useful according to the invention are colony stimulating factors and growth factors including granulocyte and/or macrophage stimulating factors (GM-CSF, G-CSF and CSF-1) and platelet derived, epidermal, insulin-like, transforming and fibroblast growth factors. The selection of the particular cytokines will depend upon the particular modulation of the immune system that is desired. The activity of cytokines on particular cell types is known to those of ordinary skill in the art.

The precise amounts of the foregoing cytokines used in the invention will depend upon a variety of factors, including the Fc-antigen selected, the dose and dose-timing selected, the mode of administration and the characteristics of the subject. The precise amounts selected can be determined without undue experimentation, particularly since a threshold amount will be any amount which will enhance the desired immune response. Thus, it is believed that nanogram to milligram amounts are useful, depending upon the mode of delivery, but that nanogram to microgram amounts are likely to be most useful because physiological levels of cytokines are correspondingly low.

The preparations of the invention are administered in effective amounts. An effective amount is that amount of a Fc-antigen fusion protein that will alone, or together with further doses, stimulate an immune response as desired. This may involve the stimulation of a humoral antibody response resulting in an increase in antibody titer in serum, improved mucosal immunity, a clonal expansion of cytotoxic T lymphocytes or tolerance to an antigen, including a self antigen. It is believed that doses ranging from 1 nanogram/kilogram to 100 milligrams/kilogram, depending upon the mode of administration, will be effective. The preferred range is believed to be between about 500 nanograms and 500 micrograms/kilogram, and most preferably between 1 microgram and 100 micrograms/kilogram. The absolute amount will depend upon a variety of factors, including the Fc-antigen fusion protein selected, the immune modulation desired, whether the administration is in a single or multiple doses, and individual patient parameters including age, physical condition, size and weight. For treatment of a subject with a tumor the size, type, location and metastases of the tumor may be factored in when determining the amount of Fc-antigen to administer. These factors are well known to those of ordinary skill in the art and can be addressed with no more than routine experimentation.

A variety of administration routes are available. The particular mode selected will depend, of course, upon the particular Fc-antigen fusion protein selected, the particular condition being treated and the dosage required for therapeutic efficacy. The methods of this invention, generally speaking, involve delivering the Fc-antigen fusion protein of the invention to an epithelial surface. Preferred modes of administration are oral, intrapulmonary, intrabinary and intranasal.

Compositions may be conveniently presented in unit dosage form and may be prepared by any of the methods well known in the art of pharmacy. All methods include the step of bringing the Fc-antigen fusion protein into association with a carrier which constitutes one or more accessory, ingredients. In general, the compositions are prepared by uniformly and intimately bringing the Fc-antigen fusion protein into association with a liquid carrier, a finely divided solid carrier, or both, and then, if necessary, shaping the product.

The preferred amount of Fc-antigen fusion protein in all pharmaceutical preparations made in accordance with the present invention should be a therapeutically effective amount thereof which is also a medically acceptable amount thereof. Actual dosage levels of Fc-antigen fusion protein in the pharmaceutical compositions of the present invention may be varied so as to obtain an amount of Fc-antigen fusion protein which is effective to achieve the desired therapeutic response for a particular patient, pharmaceutical composition of Fc-antigen fusion protein, and mode of administration, without being toxic to the patient.

The selected dosage level and frequency of administration will depend upon a variety of factors including the route of administration, the time of administration, the rate of excretion of the therapeutic agent(s) including Fc-antigen fusion protein, the duration of the treatment, other drugs, compounds and/or materials used in combination with Fc-antigen fusion protein, the age, sex, weight, condition, general health and prior medical history of the patient being treated and the like factors well known in the medical arts. For example, the dosage regimen is likely to vary with pregnant women, nursing mothers and children relative to healthy adults.

A physician having ordinary skill in the art can readily determine and prescribe the therapeutically effective amount of the pharmaceutical composition required. For example, the physician could start doses of Fc-antigen fusion protein employed in the pharmaceutical composition of the present invention at levels lower than that required to achieve the desired therapeutic effect and gradually increase the dosage until the desired effect is achieved.

The pharmaceutical compositions of the present invention, including the Fc-antigen fusion protein to a therapeutic as the active agent are suitable preferably for oral, sublingual, and intranasal delivery. The pharmaceutical compositions are suitable for the delivery of the Fc-antigen fusion protein to epithelial barriers. The pharmaceutical compositions may also be formulated to be suitable for parenteral, transdermal, intradermal and intravenous delivery.

The pharmaceutical compositions, containing biologically active Fc-antigen fusion protein as the active agent, that are suitable for transmucosal delivery via oral cavity delivery are in the form of a solid as lingual, buccal or sublingual tablets, troches, (lozenges), powders, time-release granules, pellets or the like may also be used, or in the form of a liquid as a liquid drop or drops, aerosol spray or mist, applied sublingually (under the tongue), on top of the tongue, or buccally (between the cheek and gingiva). The rate of oral mucosal membrane absorption of Fc-antigen fusion protein, is controlled by the specific liquid or solid dosage formulation selected. Specific formulations allow the process of absorption to take place over a sustained, but relatively short period of time, allowing for a gradual build up and constant blood level of the Fc-antigen fusion protein.

For prolonged delivery, the active ingredient can be formulated as a depot preparation, for administration by implantation; e.g., subcutaneous, intradermal, or intramuscular injection. Thus, for example, the active ingredient may be formulated with suitable polymeric or hydrophobic materials (e.g., as an emulsion in an acceptable oil) or ion exchange resins, or as sparingly soluble derivatives; e.g., as a sparingly soluble salt form of the Fc-antigen fusion protein.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound. By way of example, but not by limitation, the Fc-antigen fusion protein may be conjugated to the following therapeutics for epithelial barrier targeted delivery:

For buccal or sublingual administration, the compositions may take the form of tablets or lozenges formulated in conventional manner. For rectal and vaginal routes of administration, the active ingredient may be formulated as solutions (for retention enemas) suppositories or ointments.

For administration by inhalation, the active ingredient can be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The coordinate administration methods of the instant invention optionally incorporate effective mucolytic or mucus-clearing agents, which serve to degrade, thin or clear mucus from intranasal mucosal surfaces to facilitate absorption of intranasally administered biotherapeutic agents. Within these methods, a mucolytic or mucus-clearing agent is coordinately administered as an adjunct compound to enhance intranasal delivery of the biologically active agent. Alternatively, an effective amount of a mucolytic or mucus-clearing agent is incorporated as a processing agent within a multi-processing method of the invention, or as an additive within a combinatorial formulation of the invention, to provide an improved formulation that enhances intranasal delivery of biotherapeutic compounds by reducing the barrier effects of intranasal mucus.

Agents disclosed herein may be administered to subjects by a variety of mucosal administration modes, including by oral, rectal, vaginal, intranasal, intrapulmonary, or transdermal delivery, or by topical delivery to the eyes, ears, skin or other mucosal surfaces. Optionally, fusion proteins, and other biologically active agents disclosed herein can be coordinately or adjunctively administered by non-mucosal routes, including by intramuscular, subcutaneous, intravenous, intra-atrial, intra-articular, intraperitoneal, or parenteral routes. In other alternative embodiments, the biologically active agent(s) can be administered ex vivo by direct exposure to cells, tissues or organs originating from a mammalian subject, for example as a component of an ex vivo tissue or organ treatment formulation that contains the biologically active agent in a suitable, liquid or solid carrier.

Compositions according to the present invention are often administered in an aqueous solution as a nasal or pulmonary spray and may be dispensed in spray form by a variety of methods known to those skilled in the art. Preferred systems for dispensing liquids as a nasal spray are disclosed in U.S. Pat. No. 4,511,069. Such formulations may be conveniently prepared by dissolving compositions according to the present invention in water to produce an aqueous solution, and rendering the solution sterile. The formulations may be presented in multi-dose containers, for example in the sealed dispensing system disclosed in U.S. Pat. No. 4,511,069. Other suitable nasal spray delivery systems have been described in Transdermal Systemic Medication, Chien, Y. W. Ed., Elsevier Publishers, New York, 1985; and in U.S. Pat. No. 4,778,810 (each incorporated herein by reference). Additional aerosol delivery forms may include, e.g., compressed air-, jet-, ultrasonic-, and piezoelectric nebulizers, which deliver the biologically active agent dissolved or suspended in a pharmaceutical solvent, e.g., water, ethanol, or a mixture thereof.

Nasal and pulmonary spray solutions of the present invention typically comprise the drug or drug to be delivered, optionally formulated with a surface active agent, such as a nonionic surfactant (e.g., polysorbate-80), and one or more buffers. In some embodiments of the present invention, the nasal spray solution further comprises a propellant. The pH of the nasal spray solution is optionally between about pH 6.8 and 7.2, but when desired the pH is adjusted to optimize delivery of a charged macromolecular species (e.g., a therapeutic protein or peptide) in a substantially unionized state. The pharmaceutical solvents employed can also be a slightly acidic aqueous buffer (pH 4-6). Suitable buffers for use within these compositions are as described above or as otherwise known in the art. Other components may be added to enhance or maintain chemical stability, including preservatives, surfactants, dispersants, or gases. Suitable preservatives include, but are not limited to, phenol, methyl paraben, paraben, m-cresol, thiomersal, benzylalkonium chloride, and the like. Suitable surfactants include, but are not limited to, oleic acid, sorbitan trioleate, polysorbates, lecithin, phosphotidyl cholines, and various long chain diglycerides and phospholipids. Suitable dispersants include, but are not limited to, ethylenediaminetetraacetic acid, and the like. Suitable gases include, but are not limited to, nitrogen, helium, chlorofluorocarbons (CFCs), hydrofluorocarbons (HFCs), carbon dioxide, air, and the like.

Within alternate embodiments, mucosal formulations are administered as dry powder formulations comprising the biologically active agent in a dry, usually lyophilized, form of an appropriate particle size, or within an appropriate particle size range, for intranasal delivery. Minimum particle size appropriate for deposition within the nasal or pulmonary passages is often about 0.5u mass median equivalent aerodynamic diameter (MMEAD), commonly about 1 u MMEAD, and more typically about 2u MMEAD. Maximum particle size appropriate for deposition within the nasal passages is often about 10 u MMEAD, commonly about 8 u MMEAD, and more typically about 4 u MMEAD. Intranasally respirable powders within these size ranges can be produced by a variety of conventional techniques, such as jet milling, spray drying, solvent precipitation, supercritical fluid condensation, and the like. These dry powders of appropriate MMEAD can be administered to a patient via a conventional dry powder inhaler (DPI) which rely on the patient's breath, upon pulmonary or nasal inhalation, to disperse the power into an aerosolized amount. Alternatively, the dry powder may be administered via air assisted devices that use an external power source to disperse the powder into an aerosolized amount, e.g., a piston pump.

Dry powder devices typically require a powder mass in the range from about 1 mg to 20 mg to produce a single aerosolized dose ("puff"). If the required or desired dose of the biologically active agent is lower than this amount, the powdered active agent will typically be combined with a pharmaceutical dry bulking powder to provide the required total powder mass. Preferred dry bulking powders include sucrose, lactose, dextrose, mannitol, glycine, trehalose, human serum albumin (HSA), and starch. Other suitable dry bulking powders include cellobiose, dextrans, maltotriose, pectin, sodium citrate, sodium ascorbate, and the like.

To formulate compositions for mucosal delivery within the present invention, the biologically active agent can be combined with various pharmaceutically acceptable additives, as well as a base or carrier for dispersion of the active agent(s). Desired additives include, but are not limited to, pH control agents, such as arginine, sodium hydroxide, glycine, hydrochloric acid, citric acid, etc. In addition, local anesthetics (e.g., benzyl alcohol), isotonizing agents (e.g., sodium chloride, mannitol, sorbitol), adsorption inhibitors (e.g., Tween 80), solubility enhancing agents (e.g., cyclodextrins and derivatives thereof), stabilizers (e.g., serum albumin), and reducing agents (e.g., glutathione) can be included. When the composition for mucosal delivery is a liquid, the tonicity of the formulation, as measured with reference to the tonicity of 0.9% (w/v) physiological saline solution taken as unity, is typically adjusted to a value at which no substantial, irreversible tissue damage will be induced in the nasal mucosa at the site of administration. Generally, the tonicity of the solution is adjusted to a value of about ⅓ to 3, more typically ½ to 2, and most often ¾ to 1.7.

The biologically active agent may be dispersed in a base or vehicle, which may comprise a hydrophilic compound having a capacity to disperse the active agent and any desired additives. The base may be selected from a wide range of suitable carriers, including but not limited to, copolymers of polycarboxylic acids or salts thereof, carboxylic anhydrides (e.g. maleic anhydride) with other monomers (e.g. methyl (meth)acrylate, acrylic acid, etc.), hydrophilic vinyl polymers such as polyvinyl acetate, polyvinyl alcohol, polyvinylpyrrolidone, cellulose derivatives such as hydroxymethylcellulose, hydroxypropylcellulose, etc., and natural polymers such as chitosan, collagen, sodium alginate, gelatin, hyaluronic acid, and nontoxic metal salts thereof. Often, a biodegradable polymer is selected as a base or carrier, for example, polylactic acid, poly(lactic acid-glycolic acid) copolymer, polyhydroxybutyric acid, poly (hydroxybutyric acid-glycolic acid) copolymer and mixtures thereof. Alternatively or additionally, synthetic fatty acid esters such as polyglycerin fatty acid esters, sucrose fatty acid esters, etc. can be employed as carriers. Hydrophilic polymers and other carriers can be used alone or in combination, and enhanced structural integrity can be imparted to the carrier by partial crystallization, ionic bonding, cross-linking and the like. The carrier can be provided in a variety of forms, including, fluid or viscous solutions, gels, pastes, powders, microspheres and films for direct application to the nasal mucosa. The use of a selected carrier in this context may result in promotion of absorption of the biologically active agent.

The biologically active agent can be combined with the base or carrier according to a variety of methods, and release of the active agent may be by diffusion, disintegration of the carrier, or associated formulation of water channels. In some circumstances, the active agent is dispersed in microcapsules (microspheres) or nanocapsules (nanospheres) prepared from a suitable polymer, e.g., isobutyl 2-cyanoacrylate (see, e.g., Michael, et al., J. Pharmacy Pharmacol. 43:1-5, 1991), and dispersed in a biocompatible dispersing medium applied to the nasal mucosa, which yields sustained delivery and biological activity over a protracted time.

To further enhance mucosal delivery of pharmaceutical agents within the invention, formulations comprising the active agent may also contain a hydrophilic low molecular weight compound as a base or excipient. Such hydrophilic low molecular weight compounds provide a passage medium through which a water-soluble active agent, such as a physiologically active peptide or protein, may diffuse through the base to the body surface where the active agent is absorbed. The hydrophilic low molecular weight compound optionally absorbs moisture from the mucosa or the administration atmosphere and dissolves the water-soluble active peptide. The molecular weight of the hydrophilic low molecular weight compound is generally not more than 10000 and preferably not more than 3000. Exemplary hydrophilic low molecular weight compound include polyol compounds, such as oligo-, di- and monosaccharides such as sucrose, mannitol, lactose, L-arabinose, D-erythrose, D-ribose, D-xylose, D-mannose, D-galactose, lactulose, cellobiose, gentibiose, glycerin and polyethylene glycol. Other examples of hydrophilic low molecular weight compounds useful as carriers within the invention include N-methylpyrrolidone, and alcohols (e.g., oligovinyl alcohol, ethanol, ethylene glycol, propylene glycol, etc.). These hydrophilic low molecular weight compounds can be used alone or in combination with one another or with other active or inactive components of the intranasal formulation.

The compositions of the invention may alternatively contain as pharmaceutically acceptable carriers substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc. For solid compositions, conventional nontoxic pharmaceutically acceptable carriers can be used which include, for example, pharmaceutical grades of mannitol, lactose, starch, magnesium stearate, sodium saccharin, talcum, cellulose, glucose, sucrose, magnesium carbonate, and the like.

Therapeutic compositions for administering the biologically active agent can also be formulated as a solution, microemulsion, or other ordered structure suitable for high concentration of active ingredients. The carrier can be a solvent or dispersion medium containing, for example, water, ethanol, polyol (for example, glycerol, propylene glycol, and liquid polyethylene glycol, and the like), and suitable mixtures thereof. Proper fluidity for solutions can be maintained, for example, by the use of a coating such as lecithin, by the maintenance of a desired particle size in the case of dispersible formulations, and by the use of surfactants. In many cases, it will be desirable to include isotonic agents, for example, sugars, polyalcohols such as mannitol, sorbitol, or sodium chloride in the composition. Prolonged absorption of the biologically active agent can be brought about by including in the composition an agent which delays absorption, for example, monostearate salts and gelatin.

In certain embodiments of the invention, the biologically active agent is administered in a time release formulation, for example in a composition which includes a slow release polymer. The active agent can be prepared with carriers that will protect against rapid release, for example a controlled release vehicle such as a polymer, microencapsulated delivery system or bioadhesive gel. Prolonged delivery of the active agent, in various compositions of the invention can be brought about by including in the composition agents that delay absorption, for example, aluminum monosterate hydrogels and gelatin. When controlled release formulations of the biologically active agent is desired, controlled release binders suitable for use in accordance with the invention include any biocompatible controlled-release material which is inert to the active agent and which is capable of incorporating the biologically active agent. Numerous such materials are known in the art. Useful controlled-release binders are materials that are metabolized slowly under physiological conditions following their intranasal delivery (e.g., at the nasal mucosal surface, or in the presence of bodily fluids following transmucosal delivery). Appropriate binders include but are not limited to biocompatible polymers and copolymers previously used in the art in sustained release formulations. Such biocompatible compounds are non-toxic and inert to surrounding tissues, and do not trigger significant adverse side effects such as nasal irritation, immune response, inflammation, or the like. They are metabolized into metabolic products that are also biocompatible and easily eliminated from the body.

Exemplary polymeric materials for use in this context include, but are not limited to, polymeric matrices derived from copolymeric and homopolymeric polyesters having hydrolysable ester linkages. A number of these are known in the art to be biodegradable and to lead to degradation products having no or low toxicity. Exemplary polymers include polyglycolic acids (PGA) and polylactic acids (PLA), poly(DL-lactic acid-co-glycolic acid) (DL PLGA), poly(D-lactic acid-coglycolic acid) (D PLGA) and poly(L-lactic acid-co-glycolic acid) (L PLGA). Other useful biodegradable or bioerodable polymers include but are not limited to such polymers as poly(ε-caprolactone), poly(ε-aprolactone-CO-lactic acid), poly(ε-aprolactone-CO-glycolic acid), poly(beta-hydroxy butyric acid), poly(alkyl-2-cyanoacrilate), hydrogels such as poly(hydroxyethyl methacrylate), polyamides, poly(amino acids) (i.e., L-leucine, glutamic acid, L-aspartic acid and the like), poly (ester urea), poly (2-hydroxyethyl DL-aspartamide), polyacetal polymers, polyorthoesters, polycarbonate, polymaleamides, polysaccharides and copolymers thereof. Many methods for preparing such formulations are generally known to those skilled in the art. J. R. Robinson, ed., Sustained and Controlled Release Drug Delivery Systems, Marcel Dekker, Inc., New York, 1978, incorporated herein by reference. Other useful formulations include controlled-release compositions such as are known in the art for the administration of leuprolide (trade name: Lupron™), e.g., microcapsules, U.S. Pat. Nos. 4,652,441 and 4,917,893, each incorporated herein by reference, lactic acid-glycolic acid copolymers useful in making microcapsules and other formulations, U.S. Pat. Nos. 4,677,191 and 4,728,721, each incorporated herein by reference, and sustained-release compositions for water-soluble peptides. U.S. Pat. No. 4,675,189, incorporated herein by reference.

The mucosal formulations of the invention typically must be sterile and stable under all conditions of manufacture, storage and use. Sterile solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders, methods of preparation include vacuum drying and freeze-drying which yields a powder of the active ingredient plus any additional desired ingredient from a previously sterile-filtered solution thereof. The prevention of the action of microorganisms can be accomplished by various antibacterial and antifungal agents, for example, parabens, chlorobutanol, phenol, sorbic acid, thimerosal, and the like.

In more detailed aspects of the invention, the biologically active agent is stabilized to extend its effective half-life following delivery to the subject, particularly for extending metabolic persistence in an active state within the physiological environment (e.g., at the nasal mucosal surface, in the bloodstream, or within a connective tissue compartment or fluid-filled body cavity). For this purpose, the biologically active agent may be modified by chemical means, e.g., chemical conjugation, N-terminal capping, PEGylation, or recombinant means, e.g., site-directed mutagenesis or construction of fusion proteins, or formulated with various stabilizing agents or carriers. Thus stabilized, the active agent administered as above retains biological activity for an extended period (e.g., 2-3, up to 5-10 fold greater stability) under physiological conditions compared to its non-stabilized form.

In accordance with the various treatment methods of the invention, the biologically active agent is delivered to a mammalian subject in a manner consistent with conventional methodologies associated with management of the disorder for which treatment or prevention is sought. In accordance with the disclosure herein, a prophylactically or therapeutically effective amount of the biologically active agent is administered to a subject in need of such treatment for a time and under conditions sufficient to prevent, inhibit, and/or ameliorate a selected disease or condition or one or more symptom(s) thereof.

Mucosal administration according to the invention allows effective self-administration of treatment by patients, provided that sufficient safeguards are in place to control and monitor dosing and side effects. Mucosal administration also overcomes certain drawbacks of other administration forms, such as injections, that are painful and expose the patient to possible infections and may present drug bioavailability problems. For nasal and pulmonary delivery, systems for controlled aerosol dispensing of therapeutic liquids as a spray are well known. In one embodiment, metered doses of active agent are delivered by means of a specially constructed mechanical pump valve (U.S. Pat. No. 4,511,069, incorporated herein by reference). This hand-held delivery device is uniquely nonvented so that sterility of the solution in the aerosol container is maintained indefinitely.

For prophylactic and treatment purposes, the biologically active agent(s) disclosed herein may be administered to the subject in a single bolus delivery, via continuous delivery (e.g., continuous transdermal, mucosal, or intravenous delivery) over an extended time period, or in a repeated administration protocol (e.g., by an hourly, daily or weekly, repeated administration protocol). In this context, a therapeutically effective dosage of the biologically active agent(s) may include repeated doses within a prolonged prophylaxis or treatment regimen, that will yield clinically significant results to alleviate one or more symptoms or detectable conditions associated with a targeted disease or condition as set forth above. Determination of effective dosages in this context is typically based on animal model studies followed up by human clinical trials and is guided by determining effective dosages and administration protocols that significantly reduce the occurrence or severity of targeted disease symptoms or conditions in the subject. Suitable models in this regard include, for example, murine, rat, porcine, feline, non-human primate, and other accepted animal model subjects known in the art. Alternatively, effective dosages can be determined using in vitro models (e.g., immunologic and histopathologic assays). Using such models, only ordinary calculations and adjustments are typically required to determine an appropriate concentration and dose to administer a therapeutically effective amount of the biologically active agent(s) (e.g., amounts that are intranasally effective, transdermally effective, intravenously effective, or intramuscularly effective to elicit a desired response). In alternative embodiments, an "effective amount" or "effective dose" of the biologically active agent(s) may simply inhibit or enhance one or more selected biological activity(ies) correlated with a disease or condition, as set forth above, for either therapeutic or diagnostic purposes.

The actual dosage of biologically active agents will of course vary according to factors such as the disease indication and particular status of the subject (e.g., the subject's age, size, fitness, extent of symptoms, susceptibility factors, etc.), time and route of administration, other drugs or treatments being administered concurrently, as well as the specific pharmacology of the biologically active agent(s) for eliciting the desired activity or biological response in the subject. Dosage regimens may be adjusted to provide an optimum prophylactic or therapeutic response. A therapeutically effective amount is also one in which any toxic or detrimental side effects of the biologically active agent is outweighed in clinical terms by therapeutically beneficial effects. A non-limiting range for a therapeutically effective amount of a biologically active agent within the methods and formulations of the invention is 0.01 ug/kg-10 mg/kg, more typically between about 0.05 and 5 mg/kg, and in certain embodiments between about 0.2 and 2 mg/kg. Alternatively, a non-limiting range for a therapeutically effective amount of a biologically active agent within the methods and formulations of the invention is between about 0.001 pmol to about 100 pmol per kg body weight, between about 0.01 pmol to about 10 pmol per kg body weight, between about 0.1 pmol to about 5 pmol per kg body weight, or between about 0.5 pmol to about 1.0 pmol per kg body weight. Dosages within this range can be achieved by single or multiple administrations, including, e.g., multiple administrations per day, daily or weekly administrations. Per administration, it is desirable to administer at least one microgram of the biologically active agent (e.g., one or more Fc-antigen fusion proteins), more typically between about 10 ug and 5.0 mg, and in certain embodiments between about 100 ug and 1.0 or 2.0 mg to an average human subject. It is to be further noted that for each particular subject, specific dosage regimens should be evaluated and adjusted over time according to the individual need and professional judgment of the person administering or supervising the administration of the permeabilizing peptide(s) and other biologically active agent(s).

Dosage of biologically active agents may be varied by the attending clinician to maintain a desired concentration at the target site. For example, a selected local concentration of the biologically active agent in the bloodstream may be about 1-50 nanomoles per liter, sometimes between about 1.0 nanomole per liter and 10, 15 or 25 nanomoles per liter, depending on the subject's status and projected or measured response. In an alternative example, a selected local concentration of the biologically active agent in the bloodstream may be between about 0.1 pmol/L to about 1000 pmol/L of blood plasma or CSF, between about 1.0 pmol/L to about 100 pmol/L of blood plasma or CSF, between about 1.0 pmol/L to about 10 pmol/L of blood plasma or CSF, or between about 5.0 pmol/L to about 10 pmol/L of blood plasma or CSF. Higher or lower concentrations may be selected based on the mode of delivery, e.g., trans-epidermal, rectal, oral, or intranasal delivery versus intravenous or subcutaneous delivery. Dosage should also be adjusted based on the release rate of the administered formulation, e.g., of a nasal spray versus powder, sustained release oral versus injected particulate or transdermal delivery formulations, etc. To achieve the same serum concentration level, for example, slow-release particles with a release rate of 5 nanomolar (under standard conditions) would be administered at about twice the dosage of particles with a release rate of 10 nanomolar.

The instant invention also includes kits, packages and multicontainer units containing the above described pharmaceutical compositions, active ingredients, and/or means for administering the same for use in the prevention and treatment of diseases and other conditions in mammalian subjects. Briefly, these kits include a container or formulation that contains one or more Fc-antigen fusion proteins, in combination with mucosal delivery enhancing agents disclosed herein formulated in a pharmaceutical preparation for mucosal delivery. The biologically active agent(s) is/are optionally contained in a bulk dispensing container or unit or multi-unit dosage form. Optional dispensing means may be provided, for example a pulmonary or intranasal spray applicator. Packaging materials optionally include a label or instruction indicating that the pharmaceutical agent packaged therewith can be used mucosally, e.g., intranasally, for treating or preventing a specific disease or condition. In more detailed embodiments of the invention, kits include one or more mucosal delivery-enhancing agents selected from: (a) aggregation inhibitory agents; (b) charge modifying agents; (c) pH control agents; (d) degradative enzyme inhibitors; (e) mucolytic or mucus clearing agents; (f) ciliostatic agents; (g) membrane penetration-enhancing agents (e.g., (i) a surfactant, (ii) a bile salt, (iii) a phospholipid or fatty acid additive, mixed micelle, liposome, or carrier, (iv) an alcohol, (v) an enamine, (vi) an NO donor compound, (vii) a long-chain amphipathic molecule, (viii) a small hydrophobic penetration enhancer; (ix) sodium or a salicylic acid derivative; (x) a glycerol ester of acetoacetic acid, (xi) a cyclodextrin or beta-cyclodextrin derivative, (xii) a medium-chain fatty acid, (xiii) a chelating agent, (xiv) an amino acid or salt thereof, (xv) an N-acetylamino acid or salt thereof, (xvi) an enzyme degradative to a selected membrane component, (xvii) an inhibitor of fatty acid synthesis, (xviii) an inhibitor of cholesterol synthesis; or (xix) any combination of the membrane penetration enhancing agents of (i)-(xviii)); (h) secondary modulatory agents of epithelial junction physiology, such as nitric oxide (NO) stimulators, chitosan, and chitosan derivatives; (i) vasodilator agents; (j) selective transport-enhancing agents; and (k) stabilizing delivery vehicles, carriers, supports or complex-forming species with which the biologically active agent is/are effectively combined, associated, contained, encapsulated or bound to stabilize the active agent for enhanced mucosal delivery.

The contents of all cited references (including literature references, issued patents, published patent applications, and co-pending patent applications) cited throughout this application are hereby expressly incorporated by reference.

Other features of the invention will become apparent in the course of the following descriptions of exemplary embodiments which are given for illustration of the invention and are not intended to be limiting thereof.

The following MATERIALS AND METHODS were used in the examples that follow.

Materials and Method for HSV-2 gD-Fc Vaccine.

Cells, Antibodies, and Virus.

Inner Medullary Collecting Duct (IMCD) cell line and IMCD cells expressing rat FcRn were obtained from Dr. Neil Simister at Brandies University. Vero and Chinese hamster ovary (CHO-K) cells were purchased from American Tissue Culture Collection (ATCC). IMCD, Vero, and CHO cells were maintained in DMEM complete medium (Invitrogen Life Technologies) supplemented with 10 mM HEPES, 10% fetal bovine serum, 2 mM L-glutamine, non-essential amino acids, and penicillin (0.1 mg/ml)/streptomycin (0.292 mg/ml). Recombinant IMCD and CHO cells were grown under 400 mg/ml of G418 if necessary. Cells from spleen or bone marrow were grown in complete RPMI 1640 medium. Herpes Simplex Virus-2 (HSV-2) strain 186 was from Dr. Lawrence Stanberry (Columbia University, New York, N.Y.) and HSV-2 stocks were prepared by infection of Vero cell monolayers at a multiplicity of infection (MOI) of 0.01. All cells and viruses were grown in a humidified atmosphere of 5% $CO_2$ at 37° C. Affinity purified antibody for mouse FcRn was made as previously described (30). HRP-conjugated donkey anti-rabbit or rabbit anti-mouse antibody was purchased from Pierce (Rockland). Purified mouse IgG and chicken IgY was from Rockland Laboratories, and HRP-conjugated goat anti-mouse IgG1, IgG2a and IgG3 were from Southern Biotech. All DNA modifying enzymes were purchased from New England Biolabs. Purified HSV-2 glycoprotein D was purchased from Meridian Life Science.

Expression of gD-Fc Fusion Proteins.

The cDNA encoding the extracellular domain of HSV-2 gD (SEQ ID NO:2) with the signal peptide, 1-25 aa, nucleotides 1-75 of SEQ ID NO:2, which will be cleaved off in the mature form of gD was amplified by PCR from a plasmid provided by Dr. Patricia G. Spear (Northwestern University) using the primer pair (5'-cccaagcttaccatggggcgtttgacctccg-gcgtc-3' (SEQ ID NO:3, 5'-agatcccgagccacctcctcc ggacccac-ccccgcctgatccgcccgggttgctgggggg-3', SEQ ID NO:4). The antisense primer introduces an extension with fourteen codons for glycine and serine residues (GSGGGGSGGGGSGS, SEQ ID NO:1). The Fc-fragment of mouse IgG2a containing the hinge, an extended CH2 and a CH3 domain was amplified by RT-PCR from the OKT3 hybridoma using primer pair, forward primer: 5'-GGA TCA GGC GGG GGT GGG TCC GGA GGA GGT GGC TCG GGA TCT GAG CCC AGA GGGCCC A-3' (SEQ ID NO:5) (Bolded letter represents the GS linker sequence), and reverse primer: 5'-CCGGAATTCTCATTTACCCG-GAGTC-3' SEQ ID NO:6). The mouse IgG2a Fc fragment was used because mouse IgG2a, but not IgG1, is capable of binding mouse FcgRI, a high affinity receptor for IgG. Similarly, the forward primer for IgG2a Fc has complementary glycine and serine codons for gD. A mutant Fc (HQ310 and HN433), unable to bind mouse FcRn, was made by oligonucleotide site-directed mutagenesis (Clontech) and designated as an Fc/mut. To construct a nonlytic Fc fragment, oligonucleotide site-directed mutagenesis was used to replace the C1q binding motif Glu318, Lys320, Lys322 with Ala residues (14) (SEQ ID NO:7). Fusions were then performed in a PCR-based gene assembly approach by mixing the cDNA for gD and the Fc fragment. All these DNA fragments were ligated into the pCDNA3 vector. Each construct was verified by DNA sequencing.

The plasmids containing the chimeric gD-Fc fragment (SEQ ID NO:8) were transfected into CHO cells. G418-resistant clones were selected for secretion of gD-Fc fusion protein. SDS-PAGE and Western blot were performed to assess the recombinant fusion proteins in serum-free medium (Invitrogen). The highest secreting clones were screened. Recombinant proteins were purified from CHO cell supernatants by affinity chromatography using Protein A Sepharose 4 Fast Flow (Amersham) or goat anti-mouse IgG affinity column (Rockland). Protein concentration was measured with Coomassie (Bradford) protein assay kit (Pierce) using mouse IgG2a as standard.

Western Blot and SDS-PAGE Gel Electrophoresis.

The proteins or cell lysates were resolved on a 12% SDS-PAGE gel under a reducing or non-reducing condition. Proteins were transferred onto a nitrocellulose membrane (Schleicher & Schuell). The membranes were blocked with 5% non-fat milk, probed separately with anti-gD, anti-IgG Fc Ab or anti-mouse FcRn for 1 hr, and followed by incubation with HRP-conjugated rabbit anti-mouse or donkey anti-rabbit Ab. All blocking, incubation, and washing were performed in PBST solution (PBS and 0.05% Tween 20). Proteins were visualized by ECL (Pierce).

In Vitro and In Vivo Transcytosis.

The in vitro IgG transport assay was performed as a modification from previously-described methods (15, 36). IMCD cells expressing rat FcRn were grown on transwell filter inserts (Corning Costar) to form a monolayer exhibiting transepithelial electrical resistances (TER, 300 $\Omega \cdot cm^2$). TER was measured using a tissue-resistance measurement equipped with planar electrodes (World Precision Instruments). Monolayers were equilibrated in Hanks' balanced salt solution. Fusion proteins (50 ug/ml) were applied to the apical compartment, and incubated with DMEM medium supplied with or without 1 mg/ml of mouse IgG or chicken IgY as competitors for 2 hr at 37° C. degree.

Transported proteins were sampled from the basolateral chamber and analyzed by reducing SDS-PAGE and Western blot-ECL. For in vivo transport, the biotinylated 20 ug of fusion proteins or gD alone in 20 ul of PBS were administered intranasally (i.n.) into the mice that were anethesitized with 100 ul of avertin (40 mg/ml). 8 hr later or at indicated time points, transported proteins in sera were determined by ELISA.

Mouse Immunization and Virus Challenge.

Six to eight week-old Female inbred C57BL/6 mice were purchased from Charles River. FcRn knockout mice on a C57BL/6 background (16) were from the Jackson Laboratory. All mice were housed in the animal resources facility at the University of Maryland. All animal studies were reviewed and approved by the Institutional Animal Care and Use Committee. To overcome the possible mucosal immune tolerance (37, all proteins and PBS were mixed with immunostimulatory DNA rich in CG motifs CpG ODN 1826 (abbreviated CpG). Groups of 5 mice were intranasally immunized with 20 μl of 20 ug gD-Fc/wt, gD-Fc/mut, or recombinant gD alone in combination with 20 mg CpG (5'-TCCATGACGTTCCTGACGTT-3', SEQ ID NO:9) (Invivogen) per immunization at weeks 0 and 2 with an intraperitoneal injection of 100 ul of avertin (40 mg/ml). An additional group of 5 mice was mock-immunized with PBS following the same schedule. Mice were kept on their backs under anesthesia to allow the inoculum to be taken up.

Mice were inoculated with viruses intravaginally as described previously (27, 38). Briefly, prior to inoculation, each mouse was subcutaneously treated with 3 mg of medroxyprogesterone acetate (Depo-Provera) 10 days prior to virus inoculation. Hormonal pretreatment was necessary to induce susceptibility of mice to genital HSV-2 inoculation, which may reflect thinning of the genital epithelium or induction of the HSV entry receptor, nectin-1, on vaginal epithelial cells. Mice anesthetized by avertin (40 mg/ml, Sigma) were infected intravaginally with $1 \times 10^4$ pfu/100 ml of HSV-2 strain 186. Mice were kept on their backs under the influence of anesthesia for 45 min to allow infection. Mice were monitored for 15 days for the disease and death. Mice exhibiting severe disease symptom were euthanized. For virus titration, virus was inoculated into Vero cells and incubated for 45 min at 37° C. The cells were washed and DMEM containing 0.8% methcellulose and 2% FBS was added to overlay the cells. The cells were cultured for 3 days, the overlay was removed, and the cells were fixed with 3.7% formaldehyde for 1 hr, and stained with 1% crystal violet.

Preparation of Single-Cell Suspensions from Lymph Nodes, Spleen, Lung, and Vaginal Tissues.

Spleens and lymph nodes (39) were made into single-cell suspensions by passage through a sterile mesh screen. Cells were resuspended in Hanks' balanced salt solution (HBSS) and counted by trypan blue dye exclusion. For each experiment, cells were generally pooled from 3-5 mice in each group. For preparation of single-cell suspension from the lung, mice were anesthetized with 400 ul of avertin (40 mg/ml) by i.p. injection. Lungs were perfused with 10 ml PBS through the right ventricle, removed, minced with blades, and incubated with HBSS containing 2.5 mM HEPES and 1.3 mM EDTA at 37° C. for 30 min, followed by treatment at 37° C. for 1 hr with 2.5 mg/ml collengase D (Roche) in RPMI 1640 medium containing 5% FBS. The resulting cells were filtered through a 70-mm cell strainer (BD) and used for FACS analysis.

For isolation of vaginal cells, the vagina was excised, cut longitudinally, and minced with a sterile scalpel in complete RPMI 1640 culture medium. Minced tissues (epithelium and lamina propria) were digested in complete medium with sterile 0.25% collagenase D (Sigma). Digestion was accomplished with shaking incubation at 37° C. for 30 min. After digestion, tissues and cells were filtered through a sterile gauze mesh and washed with RPMI 1640 medium, and additional tissue debris was excluded by slow-speed centrifugation for 1 min. Cells were collected from the supernatant by centrifugation, resuspended in HBSS, and counted by trypan blue dye exclusion.

Flow Cytometry.

Single cell suspensions from the spleen, lung or vaginal tissues were collected and cells were spun down. Erythrocytes were then lysed in 0.14 M $NH_4Cl$, 0.017 M Tris-HCl at pH 7.2 on ice for 5 min. Cells were preincubated with an Fc block (mAb to CD16-CD32, 2.4G2, PharMingen) and washed in FACS buffer (HBSS, 2% bovine serum albumin, 0.01% sodium azide). Cells were incubated with specific antibody (0.25 ug/$10^6$ cells/100 ul) directly conjugated to fluorsecein isothiocyante (FITC), phycoerythrin (PE), washed, transferred to FACS buffer, and analyzed using a FACSAire (Becton Dickinson, Mountain View, Calif.) and FlowJo software (Tree Star). The mAbs (PharMingen) we used were anti-CD3c, 500A2; anti-CD4, RM4-5; anti-CD8, 53-6.7; anti-IFN-γ, XMG1.2; anti-B220, RA3-6B2; FAS, Jo2; CD19, 1D3. PNA was from Sigma. Purified HSV-2 gD proteins were labeled with Alexa Fluro647 protein labeling kit (Invitrogen) according to the manufacture's instruction. Cells incubated with isotype control antibodies were used to determine the background fluorescence. The isotype control antibodies included in each experiment were considered the true baseline fluorescence used to evaluate and illustrate the results for the cell-specific antigen markers.

T Cell Proliferation.

Single cell suspensions from mouse spleen were suspended in RPMI-1640 with 1% FCS, 2.5 mM Hepes at $10^7$/ml. Carboxyfluorescein diacetate succinimidyl ester (CFSE, 5 mM stock, Invitrogen) was 10-fold diluted with PBS, 4 ul of diluted CFSE was then added into $10^7$/ml cells for a 2 uM final concentration. The reaction was incubated for 10 min at 37° C. Cold FBS (1 ml) was added and incubated on ice for 5 min to stop the reaction. The cells were washed twice with RPMI-1640 with 10% FCS. Labeled cells ($5\times10^5$) were plated into 96 well plates in 200 ul of medium and cultured for 5 days. The cells were then harvested and subjected to flow cytometry assay.

Intracellular Cytokine Staining.

Intracellular IFN-γ production by primed $CD4^+$ and $CD8^+$ T cells was evaluated using bulk splenocytes or isolated lung or vaginal infiltrating lymphocytes incubated for 4 hr with 25 ug/ml of the purified gD protein or medium alone. Cells were then cultured for another 6 hr in the presence of brefeldin A (Sigma). The cells were then washed and incubated with anti-CD16/CD32 antibody to block Fcγ receptors, and stained with anti-mouse CD4, CD8, and CD3 antibodies for 15 min at 4° C. After fixation and membrane penetration with Cytofix/Cytoperm Plus (BD Biosciences), cells were stained for intracellular IFN-γ for 30 min on ice. Cells were washed three times, resuspended in FACS buffer, and analyzed by flow cytometry.

Enzyme-Linked Immunosorbent Assay (ELISA), Enzyme-Linked Immunosorbent Spot (ELISPOT), and Neutralization Test.

For the detection of gD-specific antibodies in serum, bronchial lavage and vaginal fluid, high-binding ELISA plates (Maxisorp, Nunc) were coated with 5 μg/ml of recombinant gD protein in PBS and incubated overnight at 4° C. Plates were then washed three times with 0.02% Tween 20 in PBS and blocked with 1% BSA in PBS for 1 hr at room temperature. Samples were serially diluted in 0.25% BSA-PBS and incubated for 2 hr at room temperature. HRP-conjugated rabbit anti-mouse IgG antibody (1:2,000, Pierce) or anti-mouse subclass-specific antibodies (1:5000, SouthernBiotech) was added and followed by colorimetric assay using substrate tetramethyl benzidine and a Victor III microplate reader (Perkin Elmer). Titers represent the highest dilution of samples showing a 2-fold $OD_{450}$ value over controls. Neutralizing antibodies were measured by a standard virus neutralization assay. Sera were heat-inactivated, diluted 10-fold, then in two-fold steps in MEM with 2% FBS. Fifty PFU of HSV-2 was added per well and incubated at 37° C. for 1 hr. Then, plaque assays were performed. The titers were expressed as the reciprocal of the twofold serial dilution preventing the appearance of the CPE. Each assay was done in triplicate.

For measuring gD-specific antibody-producing plasma cells, the 96-well ELISPOT plates (Millipore) were coated with 5 ug/ml gD and blocked with RPMI 5% FCS (Invitrogen) for 90 min at 37° C. and 5% $CO_2$. Serial dilutions of bone marrow single-cell suspensions were prepared in RPMI and incubated in the coated wells for 24 hr at 37° C. in 5% $CO_2$. Cells were removed, and plates were washed 5 times with 0.1% Tween 20 in PBS, then incubated with biotin labeled goat anti-mouse IgG-specific antibody (1:1500, Sigma) for 2 hr. After washing the cells, with PBS, the avidin conjugated HRP (1:2,000, Vector Laboratories) was added and incubated for 1 hr, followed by substrate from the AEC kit (BD Biosciences). Spots were counted with ELISPOT Reader and analyzed with software (Zesis). Mouse cytokines IFN-γ, IL-2, and IL-4 from the cell culture supernatant were analyzed by ELISA according to the manufacturer's instructions (BD Biosciences).

Immunofluorescence.

Immunofluorescence was performed as previously described (40). Briefly, frozen serial sections of tissues were cold-fixed in acetone for 3 min at 4° C. and blocked with 10% normal goat serum and stained with biotin-PNA (germinal centers, red), Alexa 647-IgD or anti-B220 (B cells, green), followed by Alexa 555-avidin or 488 Fluro-conjugated IgG of the corresponding species. After each step, cells were washed at least three times with 0.1% Tween-20 in PBS. Cover slips were mounted on slides with Prolong™ intifada kit (Molecular Probes) and examined using a Zees LSM 510 confocal fluorescence microscopy. Images were processed by Adobe Photoshop 7.0.

Passive Transfer of Immune Sera.

Sera were collected from 3-5 mice per group 4 weeks after the immunization, then pooled, heat inactivated and stored frozen at −80° C. until use. Mice received a single intraperitoneal (i.p.) injection of 0.3 ml immune sera 3 days prior to challenge to allow distribution and equilibration of antibody to all tissues prior to virus inoculation. Mice were challenged intravaginally with $1\times10^4$ PFU HSV-2 186 strain.

Statistics Analysis.

To compare survival curves, Kaplan-Meier log-rank analyses were used. Antibody titers, serum gD concentration, cytokine concentration and virus titers were assessed by using the unpaired two-tailed t test. Graph Pad Prism 5 provided the software for the statistical analysis.

Example 1

FcRn-mediated mucosal vaccine delivery, if feasible, may allow the host to specifically sample an Fc-fused subunit vaccine in the mucosal lumen, followed by transport of an intact antigen across the mucosal epithelial barrier. To test this possibility, we used a model pathogen herpes simplex virus type-2 (HSV-2), which causes sexually-transmitted disease and initiates infection primarily at the mucosa of the genital tract (4). The development of HSV-2 subunit vaccine is mainly focused on its major envelope glycoprotein D (gD), because of its key role in the early steps of viral infection and its being major target for both humoral and cellular immunity. Therefore, in this study, we determined the ability of FcRn to deliver the model antigen, HSV-2 gD that plays a key role in the early steps of viral infection and its being major target for both humoral and cellular immunity, across the mucosal barrier and further define protective immune responses and mechanisms relevant to this mode of mucosal vaccine delivery.

Example 2

FcRn can Efficiently Transport Intact Subunit Vaccine Antigens Across the Respiratory Mucosal Barrier.

To target gD to FcRn, we first generated the fusion protein, gD-Fc/wt, by cloning the extracellular domain of HSV-2 gD in frame with a modified form of the mouse IgG2a Fc fragment (FIG. 1). We also generated a similarly modified gD-Fc/mut fusion protein that cannot not bind FcRn owing to H to A substitutions at positions 310 and 433 (13). In both cases, the complement C1q-binding motif was eliminated to abrogate C1q binding (14) (data not shown). Comparison of these fusion proteins allowed us to evaluate the efficiency of FcRn-mediated transport and immunization efficacy. To ascertain whether the gD-Fc/wt but not the gD-Fc/mut fusion proteins were transported by FcRn, two criteria were applied. First, IMCD cells expressing FcRn (15) were evaluated for their ability to transport gD-Fc proteins in a transwell model. Indeed, FcRn-dependent transcytosis of intact gD-Fc/wt was detected in IMCD cells expressing FcRn (15) (data not shown). Second, we determined whether the gD-Fc/wt reached the bloodstream after intranasal (i.n.) inoculation. FcRn expression in mouse trachea and lung and its absence in the adult intestine were confirmed. To investigate the ability of gD-Fc/wt, gD-Fc/mut and gD proteins to undergo mucosal transport in vivo, 20 ug of the these proteins were administered i.n. and their presence in serum was measured 8 hr later using an ELISA. In comparison with gD and gD-Fc/mut, gD-Fc/wt protein was abundantly detected in the sera of FcRn WT mice. Dependence on FcRn was further confirmed by the finding that the serum concentrations of gD-Fc/wt after administration into FcRn knockout (KO) mice (16) was greatly reduced as compared with that observed in FcRn WT mice (Data not shown). These results showed that efficient delivery of gD across the respiratory barrier to the bloodstream was dependent on the Fc moiety and its ability to interact with FcRn.

Example 3

Figure 3:
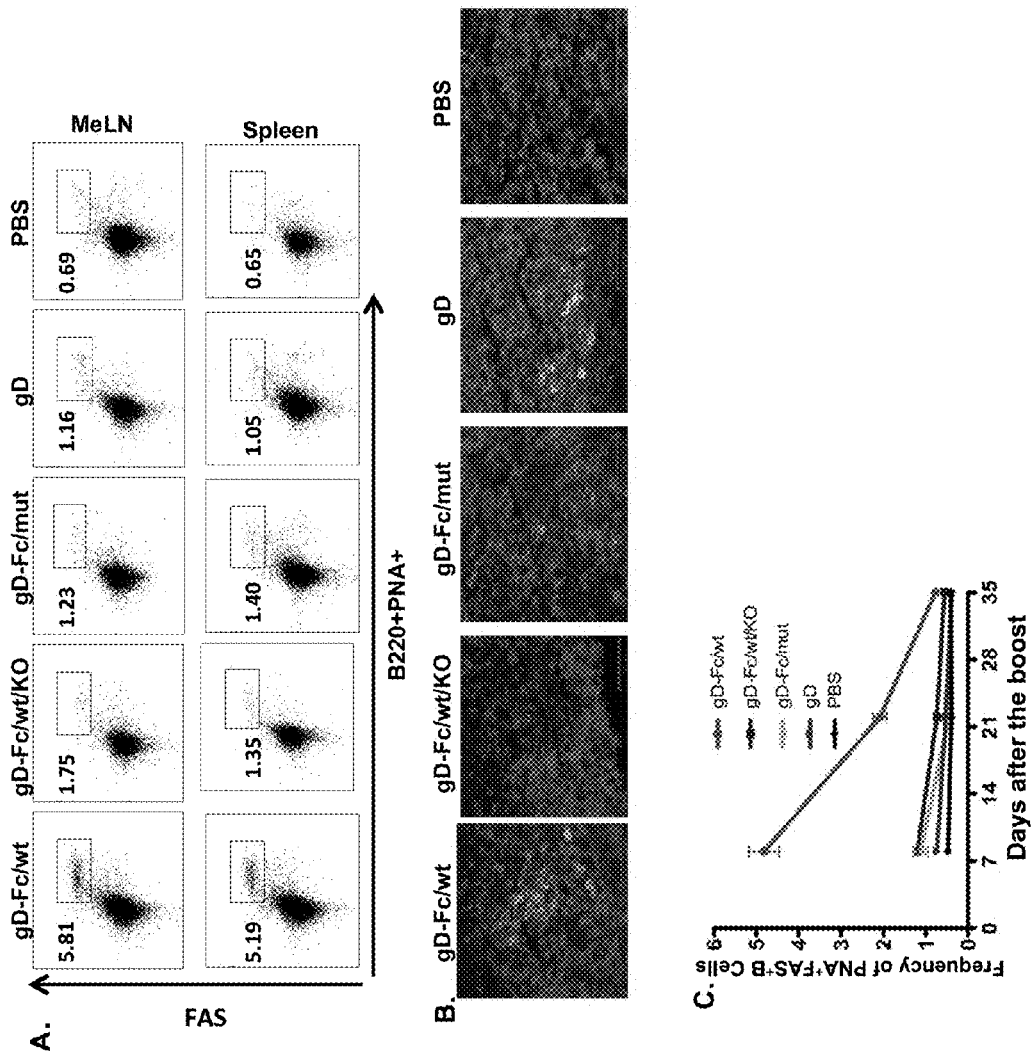
Figure 3:
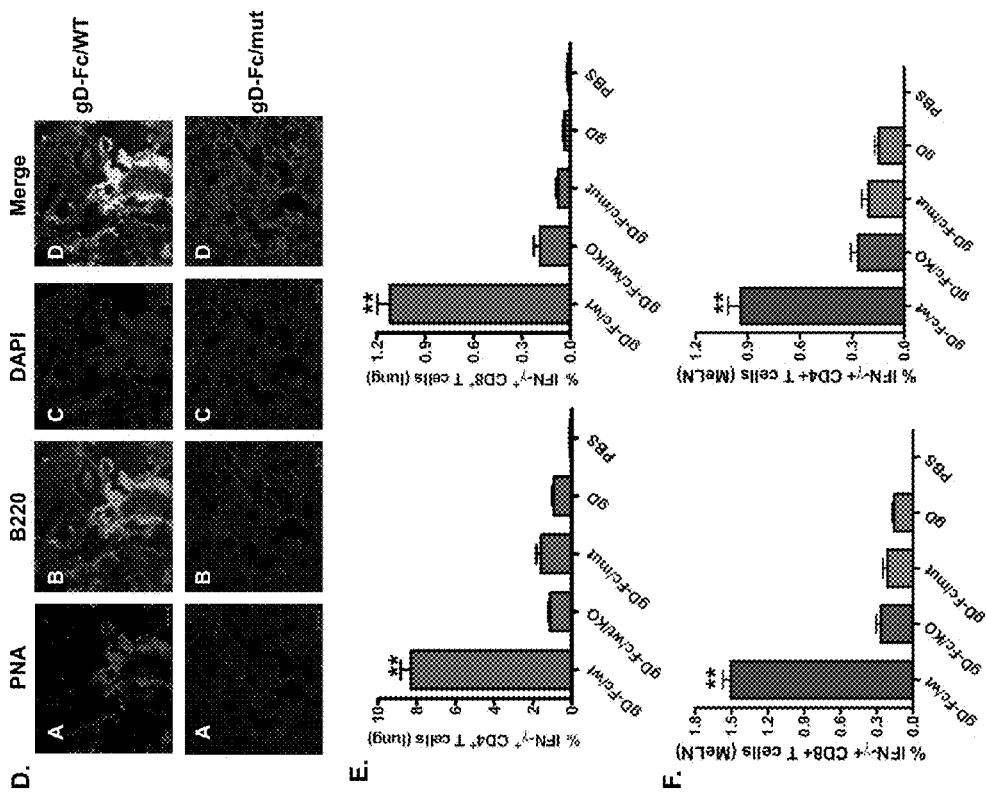

Engagement of FcRn Greatly Increased the Efficiency by which gD Antigens Induced Antigen-Specific Antibody and Cellular Immune Responses.

We then determined whether FcRn-dependent transport augmented immune response potential of the gD protein. Mice were immunized i.n. with the gD-Fc, gD protein, or PBS, all in combination with CpG, and boosted after 2 wks. The gD unlinked to an Fc fragment allowed us to evaluate FcRn-independent effects in vivo, and also determine the magnitude of any observed enhancement in immune responses conferred by inclusion of the Fc and FcRn engagement. Given the tolerogenic potential of at least some immature dendritic cells (DCs) in vivo, we co-administrated CpG, a ligand for Toll-like receptor 9 (TLR-9), in an effort to overcome possible mucosal tolerance (17). In a different study, we found that co-administration of CpG ODN with an Fc fusion protein was required in order to induce a robust IgG response (unpublished data). We first measured antibody responses to gD in vaccinated animals at various time points up to 56 days. Significantly higher titers of IgG were seen in the gD-Fc/wt immunized mice when compared with the gD, gD-Fc/mut, gD-wt/KO immunized and PBS-treated groups (FIG. 2A). Moreover, sera from the gD-Fc/wt immunized mice exhibited strong neutralizing activity (FIG. 2B) and were able to most efficiently protect from intravaginal (ivag) challenge after passive transfer as compared with sera from all other groups (Data not shown). Likewise, gD-Fc/wt proteins induced strong IFN-γ-producing $CD8^+$ and $CD4^+$ T cell responses, as evidenced by significantly higher frequency of IFN-γ producing $CD4^+$ (FIG. 2C) and $CD8^+$ (FIG. 2C) T cells in response to gD stimulation in the spleens of FcRn WT mice immunized with gD-Fc/wt relative to the other groups. The cytokine responses were dominated by IFN-γ and IL-2 and with a lack of IL-4 production (FIG. 2D). This dominant Th1 cytokine response was also supported by a major IgG2a subclass in the sera of the immunized mice (data not shown). It remains uncertain whether this polarized T cell response is caused by mucosal immunization as the result of FcRn targeting or, more likely, by the CpG used in as adjuvant, as CpG favorably induces Th1-type immune responses (17).

It is important to note that an important consequence of FcRn-targeted mucosal delivery of subunit vaccine was to elicit a strong mucosal immune response. This result is strongly supported by several lines of evidence. First, the nasopharynx-associated lymphoid tissue (NALT) and the mediastinal lymph nodes (MeLNs) draining the lung are usually the site where mucosal immune responses are initiated against antigens administered intranasally and reaching the lung (18). To ascertain the ability of the FcRn-targeted mucosal immunization to induce local humoral immune responses, we monitored the germinal center (GC) reaction in the MeLNs and spleens 10 days after the boost. Activated GCs are characterized by the presence of peanut agglutinin (PNA)-positive areas and high-level expression of Fas apoptotic death receptor in activated B cells (19). As shown in FIG. 3A, the gD-Fc/wt immunization induced a substantially higher of $FAS^+PNA^+$ $B220^+$ B cells in the MeLN or spleen in comparison with the percentages of other groups which was further validated by immunofluorescence imaging (FIG. 3B). In addition, the GC structure in the MeLNs in WT mice immunized by the gD-Fc/wt proteins was sustained much longer in comparison with that of other groups of the immunized animals (FIG. 3C). Administration of CpG alone failed to elicit appreciable GCs in the draining MeLNs, spleens, or lungs (data not shown). The formation and maintenance of GC generally leads to the differentiation of memory B cells and long-lived plasma cells. We also examined the mesenteric, cervical and inguinal lymph nodes and we failed to detect GC formation or the significant number of IFNγ secreting T cells at those sites. Second, it has been shown that i.n. administrated antigens can induce bronchus-associated lymphoid tissue (iBALT) in the lung, which is similar to GC structures (19). As shown in FIG. 3D, such GC-like structures could be detected in the lungs of gD-Fc/wt, but not gD-Fc/mut immunized mice or other groups of immunized animals by co-localization of PNA- and B220-positive signals. It was also absent from other groups of immunized animals. Appearance of the GC in the iBALT in the lung is best explained by local induction due to the presence of the transported gD antigen in the MeLNs and lung, again emphasizing that the MeLNs play a major role as the inductive site. Third, antibodies, in particular IgA and IgG, represent the first defense line on mucosal surfaces. In order to assess the ability of FcRn-targeted mucosal immunization to induce gD-specific antibody in mucosal secretions, bronchial alveolar lavage (BAL) and vaginal washes were collected 10 days following the boost and analyzed for gD-specific IgG and IgA by ELISA. Significantly increased levels of gD-specific IgG were present in the BAL and vaginal washes (data not shown) of the gD-Fc/wt protein immunized mice. WT, but not FcRn KO, mice that received the gD-Fc/wt had high levels of gD-specific IgG in BAL and vaginal washes ($p<0.01$, data not shown), suggesting the induction of mucosal IgG is FcRn-mediated. Of note is the observation that BAL- or vaginal IgG levels were much higher than that of IgA, despite high IgA levels in the nasal washings (data not shown). Indeed, IgG appears a major isotype of immunoglobulin in the lower respiratory tract and reproductive tract. Fourth, with respect to T cell immune responses in the lung and MeLNs, 4 days after the boost we detected significantly higher frequency of IFN-γ producing CD4+ and CD8+ T cells (FIGS. 3E and 3F) in response to gD stimulation in the mice immunized with the gD-Fc/wt in comparison with other groups. We conclude that antigen targeting to FcRn combined with the mucosal adjuvant CpG produced strong antibody as well as T cell mucosal immune responses. Considering that an efficient protective vaccine should induce immunity in the mucosa in order to hinder pathogen penetration and spreading, the data presented here suggest that FcRn-targeted mucosal immunization may provide an efficient approach for the development of protective mucosal vaccines.

Preferably, an effective mucosal subunit vaccine should also elicit both humoral and cell-mediated immunity not only at the mucosal delivery site, but also in systemic compartments that can access mucosal tissues distant from the immunization site (1-3). Studies have found that mucosal immunization using the intranasal route is effective for generating antibody and T cell immune responses in the female genital tract (1,2,4). Perhaps intranasal immunization stimulates cells in the NALT and its draining lymph nodes, leading to the migration of antibody secreting cells and T cells generated in the airway into the genital tract (20). We ivag challenged immunized mice with a lethal dose of HSV-2 186 strain 4 weeks following the boost. As expected, all PBS treated control mice succumbed to lethal infection. All FcRn wt mice immunized with the gD-Fc/wt survived with no obvious symptoms (data not shown), while gD-Fc/wt-immunized FcRn KO mice were incompletely protected (FIG. 4A). These data indicate that full protection is dependent on FcRn. Additionally, virus titers measured in the vaginal washes showed that the gD-Fc/wt immunized mice had eliminated the virus by day 4 after challenge (FIG. 4B). In contrast, the other groups of mice essentially failed to control viral replication. Several immune mechanisms may account for the protection of the distal vaginal mucosa. First, both mucosal and systemic antibody responses may play an important protective role. This conclusion was supported by evidence that the sera passively transferred from the gD-Fc immunized mice conferred a high level of protection (data not shown) and a significant amount of gD-specific IgG appeared in the vaginal secretions (data not shown). IgG is a major protective antibody in mouse vaginal secretions after immunization with attenuated HSV-2 (21). Second, T lymphocytes were present in the vaginal epithelium of HSV-2 challenged mice at a time coincident with virus clearance. IFN-γ is clearly indispensable for resistance to HSV-2 infections (20). The gD-Fc/wt protein induced a significantly higher frequency of IFN-γ producing CD4+ and CD8+ T cells in the vaginal tissues from the challenged mice (FIG. 4C) in comparison with other groups. The strong T cell response induced by FcRn targeted immunization could also provide resistance through direct lysis of MHC class I or II-bearing infected epithelial cells. Overall these results demonstrate that FcRn targeted mucosal immunization efficiently induced protective immunity.

Example 4

FcRn Targeted Mucosal Delivery of Vaccine Engendered an Effective Memory Immune Response.

Immunological memory is characterized by increased levels of effector T and B cells and by the host's ability to respond faster and more vigorously to a second encounter with the pathogen or vaccine antigen (22, 23). Hence, an important criterion for any vaccine is the formation and maintenance of a reservoir of memory lymphocytes with both adequate size and quality to maintain efficient immune surveillance for prolonged periods. Immunological memory (23) has been a concern in protein-based subunit mucosal vaccine development because preparations elicited levels of immunity immediately after vaccination but that immunity waned rapidly over time. However, a striking feature in this study is that FcRn targeted mucosal immunization promoted and sustained high levels of gD-specific plasma cells and memory B and T cells at least 6 months after the boost. This conclusion is strongly supported by several lines of evidence. First, gD-Fc/wt immunized mice developed significantly higher numbers of splenic memory B cells responsive to gD stimulation 6 months after the boost (FIG. 5A). By ELISPOT, we also found the significantly higher number of gD-specific IgG secreting plasma cells in the bone marrow of mice immunized with gD-Fc/wt in comparison with that of other groups (FIG. 5B). It remains to be determined if gD-specific IgA-secreting plasma cells also develop. Second, higher titers of gD-specific IgG were maintained for six months, the latest point tested after a boost in the mice immunized with the gD-Fc/wt, but high titers were not observed in groups that did not enable FcRn trafficking (FIG. 5C). Both the increase in GC and memory B cells in the spleen and the existence of long-lived plasma cells in the bone marrow niche can account for the maintenance of high levels of gD-specific IgG in circulation. Third, an important feature of memory T cells as opposed to the effector population is their proliferative potential upon reencounter with an antigen. We detected significant numbers of CD4+ (FIG. 5D, upper panel) and CD8+ (FIG. 5D, bottom panel) memory T cell proliferation by CFSE in response to gD recall in the mice immunized with gD-Fc/wt, but not in any of the other groups. This result was also verified by significantly increased numbers of actively proliferating T cells over time (data not shown). These data indicate that the gD-specific T cells had maintained a significant proliferative potential at least 6 months after the boost. Although the reason for the high memory T cell activity is not completely clear, IL-2-producing T cells formed in the responding T cell population (data not shown) may be important since IL-2 plays an important role in the successful long-term survival of memory T cells in vivo (24). Fourth, to test if the memory immune response elicited from FcRn targeted mucosal immunization could provide protection, we again ivag challenged the immunized mice with a lethal dose of HSV-2 186 strain 6 months after the boost. Mice immunized with the gD-Fc/wt proteins exhibited less severe disease symptoms (data not shown) and had 80% survival (FIG. 5E), while the majority of mice in other groups succumbed to lethal mucosal infection.

Overall, this study shows that the FcRn/IgG transport pathway can be exploited to greatly enhance the efficacy of mucosally administered vaccines. Previous studies have taken advantage of Fc fusion proteins to augment the T cell immune response to myelin basic protein (25) and mucosally administered inactivated *Francisella tularensis*/antibody immune complexes have been shown enhance protection against the highly virulent strain of *F. tularensis* (26). We have shown that FcRn targeted mucosal immunization differs notably between WT and FcRn KO mice or the gD-Fc/wt and the gD-Fc/mut immunized mice in terms of mucosal and systemic immune responses, cytokine expression profiles, the maintenance of T and B cell memory and long lived bone marrow plasma cells, and resistance to infection. We established this principle using a modified form of the mouse IgG2a Fc fragment to facilitate the vaccine antigen delivery across mucosal the barrier. We are determining the efficiency of FcRn dependent delivery of mucosal vaccines using other subclasses of IgG, for example IgG1, IgG2b, and IgG3.

Earlier studies have shown intranasal and intravaginal immunization with gD or gB proteins in combination with CpG elicited immune responses and conferred partial protection to subsequent vaginal challenge with HSV-2 (27-29). Lindqvist et al. (30) showed better protection, however, these mice were intranasally or intravaginally immunized three times by gD plus α-galactosylceramide. The mechanism by which "plain" gD or gB proteins crossed the airway or female genital epithelial barrier in those studies is not clear. Conditions that might explain passive mucosal transfer include the treatment of mice with agents that could compromise the integrity of the alveolo-capillary or mucosal epithelial barrier (31, 32), such use of volatile anesthetics or 0.5% Tween in α-galactosylceramide preparation (27-30). Moreover, injections with Depo-Provera before vaginal immunization (28-30) may affect tightness of the vaginal epithelial cells because Provera is a long-acting progesterone formulation and induces a diestrus-like state in genital tract of female mice (4). In agreement with a previous report (33), our other studies on examinations of the effect of CpG on protein transport across the nasal/tracheal mucosa (unpublished data) are not consistent with an effect of CpG on mucosal permeability or passive transfer. Regardless of the mechanism by which plain vaccine antigens may cross the mucosal barrier, our results clearly document the benefits of FcRn targeting to maximize the potential of mucosally administered vaccines to counteract mucosal pathogens, without the need for agents that may damage or otherwise compromise the integrity of mucosal barriers.

We suggest, without being bound to any theory, the following model for FcRn-targeted immunization (FIG. 5F). In general, mucosal DCs capture antigens in mucosal-associated lymphoid tissues, and subsequently migrate to draining lymph nodes where they can prime T cells (33, 34) and initiate the cognate B cell response. Persistence of vaccine antigens can facilitate long-term memory immune responses (22, 23). Thus, while FcRn-mediated transport is necessary for efficient vaccine proven necessary for effective mucosal immunization, the ability of FcRn to protect gD-Fc/wt proteins from degradation may further support the development of systemic immunity by increasing the persistence of gD-Fc/wt in circulation. Furthermore, this same protection property may augment long-term humoral immunity by maintaining serum high levels of IgG antibodies specific for gD-Fc/wt. It remains to be determined whether this delivery method can augment pre-existing immunity. Taken together, these results suggest that FcRn-targeted mucosal immunization could prove to be an effective strategy for maximizing the efficacy of vaccinations directed against a broad range of mucosal pathogens.

The following references were cited in Examples 1-4.
1. Neutra, M. R. & Kozlowski, P. A, *Nat. Rev. Immunol.* 6, 148-158 (2006).
2. Holmgren, J. & Czerkinsky, C., *Nat. Med.* 11(4 Suppl), S45-53 (2005).
3. McGhee, J. R. et al., *Vaccine* 10, 75-88 (1992).
4. Gallichan, W. S. & Rosenthal, K. L., *J. Infect. Dis.* 177, 1155-1161 (1988).
5. Neutra, M. R., et al., *Nat. Immunol.* 2, 1004-1009 (2001).
6. Nochi, T. et al., *J. Exp. Med.* 204, 2789-2796 (2007).
7. Ghetie, V. & Ward, E. S., *Annu. Rev. Immunol.* 18, 739-766 (2000).
8. He, W. et al., *Nature* 455, 542-546 (2008).
9. Dickinson, B. L. et al., *J. Clin. Invest.* 104, 903-911 (1999).
10. Roopenian, D. C., & Akilesh, S., *Nat. Rev. Immunol.* 7, 715-725 (2007).
11. Baker, K. et al., *Semin. Immunopathol.* 223-236 (2009).
12. Yoshida, M. et al., *J. Clin. Invest.* 116, 2142-2151 (2006).
13. Kim, J. K. et al., *Eur. J. Immunol.* 24, 2429-2434 (1994).
14. Duncan, A. R. & Winter, G., *Nature* 332, 738-740 (1988).
15. McCarthy, K. M., et al., *J. Cell Sci.* 113, 1277-1285 (2000).
16. Roopenian, D. C. et al., 170, 3528-3533 (2003).
17. van Duin, D. et al., *Trends Immunol.* 27, 49-55 (2006).
18. Wolf, A. J. et al., *J. Exp. Med.* 205, 105-115 (2008).
19. Moyron-Quiroz, J. E. et al., *Nat. Med.* 10, 927-934 (2004).
20. Milligan, G. N. et al., *Virology* 318, 507-515 (2004).
21. Parr, E. L. & Parr, M. B., *J. Virol.* 71, 8109-9115 (1997).
22. Ahmed, R. & Gray, D., *Science* 272, 54-60 (1996).
23. Bernasconi, N. L. et al., *Science* 298, 2199-2202 (2002).
24. Dooms, H. et al., *J. Exp. Med.* 204, 547-557 (2007).
25. Mi, W. et al., *J Immunol.* 181:7550-7561 (2008).
26. Rawool, D. B. et al., *J. Immunol.* 180, 5548-5557 (2008).
27. Gallichan, W. S. et al., *J. Immunol.* 166, 3451-3457 (2001).
28. Kwant, A., & Rosenthal, K. L., *Vaccine.* 22, 3098-3104 (2004).
29. Tengvall, S. et al., *J. Virol.* 80, 5283-5291 (2006).
30. Lindqvist, M. et al., *J. Immunol.* 182, 6435-6443 (2009).
31. ChangLai, S. P. et al., *Respiration.* 66, 506-510 (1999).
32. Lin, H., et al., *Int. J. Pharm.* 330, 23-31 (2007).
33. Kodama, S. et al., *Laryngoscope.* 116, 331-335 (2006).
34. Kelsall, B. L., & Rescigno, *Nat. Immunol.* 5, 1091-1095 (2004).
35. Yoshida, M. et al., *Immunity* 20, 76-783 (2004).

The following Materials and Methods were used in Examples 5-10 below.

Mice, Cells, Antibodies, Viruses.

Six to eight week-old female inbred C57BL/6 mice were purchased from the National Cancer Institute or Charles River. FcRn knockout mice on a C57BL/6 background (19) were from the Jackson Laboratory. All mice were bred and maintained in HEPA-filtered caging units. Animal experiments were approved by the Animal Care and Use Committee at the University of Maryland.

Madin-Darby canine kidney (MDCK) cells expressing rat FcRn were obtained from Dr. Pamela Bjorkman at the California Institute of Technology. Vero and Chinese hamster ovary (CHO-K) cells were purchased from the American Tissue Culture Collection (ATCC). MDCK, Vero, and CHO cells were maintained in DMEM complete medium (Invitrogen Life Technologies) supplemented with 10 mM HEPES, 10% fetal bovine serum, 2 mM L-glutamine, non-essential amino acids, and penicillin (0.1 ug/ml)/streptomycin (0.292 ug/ml). Recombinant MDCK and CHO cells were also grown under 400 ug/ml of G418 if necessary. Cells from spleen or bone marrow were grown in complete RPMI 1640 medium. All cells were maintained in a humidified atmosphere of 5% $CO_2$ at 37° C. Affinity-purified antibody for mouse FcRn was produced as previously described (20). Purified mouse IgG and chicken IgY were from Rockland Laboratories (Gilbertsville, Pa.). HRP-conjugated donkey anti-rabbit or rabbit anti-mouse antibody was purchased from Pierce (Rockland, Ill.); HRP-conjugated goat anti-mouse IgG1, IgG2a and IgG3 were from Southern Biotech.

All DNA modifying enzymes were purchased from New England Biolab (Ipswich, Mass.). The purified recombinant HIV Gag p24 proteins were from Meridian Life Science (Cincinnati, Ohio). Mouse anti-Gag p24 hybridoma and recombinant vaccinia virus expressing Gag (rVV-Gag) were acquired from the NIH AIDS Research & Reference Reagent Program. The rVV-Gag stocks were prepared by infection of Vero cell monolayer at a multiplicity of infection (MOI) of 0.1. DMEM complete medium was added and infected cells were cultured for 2-3 days until the CPE appears. Viruses were released from cells by three times freeze and thaw, cell debris was centrifuged, and supernatant was stored at −80° C. Virus was titrated with Vero cells with a standard plaque assay.

Western Blot and SDS-PAGE Gel Electrophoresis.

Purified proteins or cell lysates were resolved on 12% SDS-PAGE gels under a reducing or non-reducing condition. Proteins were transferred to a nitrocellulose membranes (Schleicher & Schuell); membranes were blocked with 5% non-fat milk, probed separately with primary antibodies for 1 hr, followed by incubation with HRP-conjugated rabbit anti-mouse or donkey anti-rabbit Ab for 1 hr. All blocking, incubation, and washing steps were performed in PBST solution (PBS and 0.05% Tween 20). Proteins were visualized by the ECL method (Pierce, Rockland, Ill.).

Expression of Gag-Fc Fusion Proteins.

The cDNA encoding Gag P24 from the HIV-1 isolate BH10 was amplified by PCR from a plasmid pBKBH10S provided by NIH AIDS Reference Reagent Program using forward primer: 5'-ctggtcgcttccgtgctacctagaactttaaatgcatg-3', SEQ ID NO:10 and reverse primer: 5'-agatcccgagccac-ctcctccggacccaccccgcctgatcccaaaactctt gccttatg-3', SEQ ID NO:11. The antisense primer introduces an extension with 12 codons for glycine and serine residues (GSSGGGSSGGSSS, SEQ ID NO:1). The Fc-fragment of mouse IgG2a containing hinge, CH2 and CH3 domains, was amplified by RT-PCR from the OKT3 hybridoma. Similarly, the forward primer for IgG2a Fc has complementary glycine and serine codons for Gag. A mutant Fc (HQ310 and HN433) was made by oligonucleotide site-directed mutagenesis (Clontech, Mountain View, Calif.) and designated as an Fc/mut as described previously (15). To construct a nonlytic Fc fragment, oligonucleotide site-directed mutagenesis was used to replace the C1q binding motif Glu318, Lys320, Lys322 with Ala residues (21). Fusions were then performed in a PCR-based gene assembly approach by mixing the cDNA for Gag and the Fc fragments. All these DNA fragments were digested by BamH I and EcoR I, then ligated into an engineered pCDNA3 vector carrying a CD5 protein secretion signal sequence. Each construct was verified by DNA sequencing.

Plasmids containing the chimeric Gag-Fc/wt (SEQ ID NO:12) or Gag-Fc/mut fragment were transfected into CHO cells by Effectene (Qiagen, Valencia, Calif.). G418-resistant clones were selected for secretion of Gag-Fc fusion proteins. SDS-PAGE and Western blot were performed to assess the recombinant fusion proteins in serum-free medium (Invitrogen, Carlsbad, Calif.) using HRP conjugated rabbit anti-mouse IgG or anti-Gag p24 antibody. Recombinant proteins were made from CHO cell supernatants cleaned first by ultrafiltration and purified further by affinity chromatography using Protein A Sepharose 4 Fast Flow (Amersham Pharmacia, Piscataway, N.J.) for Gag-Fc/wt or goat anti-mouse IgG affinity column (Rockland) for Gag-Fc/mut proteins. Protein concentrations were measured with Bradford protein assay kits (Pierce) using mouse IgG2a as standards.

In Vitro and In Vivo Transcytosis.

The in vitro IgG transport assay was performed as a modification of previously-described methods (22, 23). MDCK cells expressing rat FcRn (23) were grown on transwell filter inserts (Corning, Lowell, Mass.) to form a monolayer exhibiting transepithelial electrical resistances (TER, 300 $\Omega \cdot cm^2$) measured with planar electrodes (World Precision Instruments). Monolayers were equilibrated in serum free medium for 3 hr. Fusion proteins at a final concentration of 0.1 mg/ml were applied to the apical compartment, and incubated with DMEM medium supplied with or without 1 mg/ml of chicken IgY as competitors for 1 hr at 37° C. Transported proteins were sampled from the basolateral chamber and analyzed by reducing SDS-PAGE and Western blot-ECL. For in vivo transport, 20 ug of Gag-Fc fusion proteins or Gag alone in 20 ul of PBS were administered intranasally (i.n.) into the wild type or FcRn KO mice that were anethesitized with 100 ul of avertin (40 mg/ml). 8 hr later or at indicated time points, transported proteins in sera were determined by ELISA.

Mouse Immunization and Virus Challenge.

Groups of 5 mice were immunized intranasally with 20-30 μl of 20 ug Gag-Fc/wt, Gag-Fc/mut, or Gag proteins in combination with 20 ug CpG ODN1826 (5'-TCCAT-GACGTTCCTGACGTT-3', (SEQ ID NO:9) (InvivoGen, San Diego, Calif.) at weeks 0 and 2, respectively. An additional group of 5 mice was mock-immunized with PBS following the same schedule. For intranasal inoculation, 20 ul proteins or PBS were applied to each nostril of mice anesthetized with 100 ul of avertin (Sigma, 40 mg/ml). Mice were kept on their backs under anesthesia to allow the inoculums to be taken up.

Mice were challenged with viruses by intravaginal inoculation as described previously (24). Five days before each inoculation, mice were treated subcutaneously with 2 mg of medroxyprogesterone acetate (Depo-Provera). Mice were anesthetized by avertin (40 mg/ml, Sigma) and exposed intravaginally to rVV-Gag ($5 \times 10^7$ PFU) in 30 μl of PBS. Mice were kept on their backs under the anesthesia for 1 hr. Five days after challenge, mice were sacrificed. Paired ovary tissues were removed and homogenized in nylon mesh. For virus titration, serially diluted ovary samples were inoculated into Vero cells and incubated for 45 min at 37° C. The cells were washed and DMEM containing 0.8% methcellulose and 2% FBS was overlayed on the cells. The cells were cultured for 3 days, the overlay was removed, and the cells were fixed with 3.7% formaldehyde for 1 hr, and stained with 1% crystal violet.

Clear plaques were counted to determine the virus titer in terms of plaque forming units (pfu).

Enzyme-Linked Immunosorbent Assay (ELISA) and ELISPOT.

HIV Gag p24-specific antibodies were detected in serum, bronchial lavage and vaginal fluid. High-binding ELISA plates (Maxisorp, Nunc) were coated with 1 μg/ml of purified p24 protein in PBS and incubated overnight at 4° C. Plates were then washed three times with 0.2% Tween 20 in 50 mM Tris buffer and blocked with 1% BSA in PBS for 2 hr at room temperature. All samples were diluted 10-fold in PBS then transferred to counted plates and incubated for 2 hr at room temperature. HRP-conjugated rabbit anti-mouse IgG antibody (1:2,000, Pharmingen) or anti-mouse subclass-specific antibodies (1:5000, SouthernBiotech) was added and a colorimetric assay was done with tetramethyl benzidine (KPL) and a Victor III microplate reader (Perkin Elmer). Antibody titers represent the highest dilution of samples showing a 2-fold $OD_{450}$ value over controls. The mean log of the end-point dilutions was determined and used to calculate the average end-point titer. Each assay was done in triplicate. Mouse cytokines IFN-γ, IL-2, and IL-4 from the cell culture supernatant were analyzed by ELISA according to the manufacturer's instructions (BD Biosciences).

For measuring HIV Gag-specific antibody-producing plasma cells, 96-well ELISPOT plates (Millipore) were coated with 5 ug/ml Gag and blocked with RPMI 5% FCS (Invitrogen) for 90 min at 37° C. in 5% $CO_2$. Serial dilutions of bone marrow single-cell suspensions were prepared in RPMI and incubated in the coated wells for 24 hr at 37° C. in 5% $CO_2$. Cells were removed; plates were washed 5 times with 0.1% Tween 20 in PBS and then incubated with biotin labeled goat anti-mouse IgG-specific antibody (1:1500, Sigma) for 2 hr. After washing the cells with PBS, avidin conjugated HRP (1:2,000, Vector Laboratories) was added and incubated for 1 hr, and developed with substrate from the AEC kit (BD Biosciences). Spots were counted with an ELISPOT Reader and analyzed with software (Zesis).

Preparation of Single-Cell Suspensions from Spleen and Vaginal Tissues.

Spleens were made into single-cell suspensions by passing through a sterile mesh screen. Cells were resuspended in Hanks' balanced salt solution (HBSS) and counted by trypan blue dye exclusion. For each experiment, cells were generally pooled from 3 mice. Vaginal cells were isolated from tissue that was excised, cut longitudinally, and minced with a sterile scalpel in complete RPMI 1640 culture medium. Minced tissues (epithelium and lamina propria) were digested in complete medium with sterile 0.25% collagenase D. Digestion was accomplished with shaking incubation at 37° C. for 30 min. After collagenase treatment, tissues and cells were filtered through a sterile gauze mesh, washed with RPMI 1640 medium and additional tissue debris was excluded by slow-speed centrifugation for 1 min. Cells were collected from the supernatant by centrifugation, resuspended in HBSS and viable cells were counted by trypan blue dye exclusion.

Flow Cytometry.

Single cell suspensions were obtained from spleen or vaginal tissues.

Erythrocytes were lysed in 0.14 M $NH_4Cl$, 0.017 M Tris-HCl at pH 7.2 on ice for 5 min. Cells were preincubated with an Fc block (mAb to CD16-CD32, 2.4G2, PharMingen, San Diego, Calif.) and washed in FACS buffer (HBSS, 2% bovine serum albumin, 0.01% sodium azide). Blocked cells were incubated with specific antibody directly conjugated to fluorsecein isothiocyante (FITC), phycoerythrin (PE), allophycocyanin (APC), cyanine dye Cy7 (Cy7), and peridininchlorophyll proteins (PerCP) then washed, transferred to FACS buffer, and analyzed using a FACSAira (Becton Dickinson, Mountain View, Calif.) and FlowJo software (Tree Star). The mAbs (PharMingen) we used were anti-CD3c, 500A2; anti-CD4, RM4-5; anti-CD8, 53-6.7; anti-IFN-γ, XMG1.2; anti-B220, RA3-6B2; FAS, Jo2. Peanut agglutinin (PNA)-FITC was from Sigma. Purified HIV Gag proteins were labeled with Alexa Fluro647 protein labeling kit (Invitrogen) according to the manufacturer's instruction. Cells were incubated with isotype control antibodies to determine the background fluorescence. The isotype control antibodies included in each experiment were considered the true baseline fluorescence used to evaluate and illustrate the results for cell-specific antigen markers.

T Cell Proliferation Assay.

Carboxyfluorescein diacetate succinimidyl ester (CFSE, 5 mM stock, Invitrogen) dilution was used to assess T cell proliferation in response to Gag antigen. CFSE was added single cell suspensions $10^7$ cells/ml from spleens, in pre-warmed PBS/0.1% BSA for a 2 mM final concentration; reactions were incubated for 10 min at 37° C. then stopped with 5 volumes of ice-cold culture media and 5 min on ice. The cells were washed three times with RPMI-1640 containing 10% FCS. After labeling with CFSE, the splenic T cells were added in the presence of HIV Gag p24 protein (20 µg/ml), medium alone, or anti-CD3 (0.1 µg/ml) and anti-CD28 (2 µg/ml) as a positive control. Cells ($5 \times 10^5$) were cultured for 4 days. The cells were then harvested and subjected to flow cytometry assay.

Intracellular Cytokine Staining.

Intracellular IFN-γ production by primed $CD4^+$ and $CD8^+$ T cells was evaluated using bulk splenocytes or isolated vaginal infiltrating lymphocytes incubated for 12 hr with 20 ug/ml of the purified Gag protein or medium alone. Cells were then cultured for another 6 hr in the presence of 10 µg/ml brefeldin A (Sigma) to accumulate intracellular cytokines. Cells were washed, incubated for 15 min at 4° C. with 2.4G2 mAb to block Fcγ receptors, and stained with PE-conjugated anti-mouse CD3c and FITC conjugated anti-CD4 and APC-Cy™7 conjugated anti-mouse CD8a for 30 min at 4° C. The cells were fixed and permeabilized (Cytofix/Cytoperm Plus, BD Biosciences) and stained with APC-anti-IFN-γ (XMG 1.2) mAbs for 30 min at 4° C. (BD Biosciences). Cells were washed three times, resuspended in FACS buffer and analyzed by flow cytometry and FlowJo software. All plots were gated on low forward and side scatter CD3+ cells.

Histological Analysis.

Immunohistochemical staining of mouse FcRn was performed using an affinity-purified rabbit anti-mouse FcRn antibody (20). Briefly, lung and trachea were excised and embedded in Tissue-Tek OCT compound (Miles, Elkhart, Ind.). Thin sections were cut with a cryostat, transferred onto glass slides and stored at −80° C. Before staining, sections were fixed in ice-cold acetone for 10 min. After extensive washes in PBS and blocking buffer (PBS-2% bovine serum albumin-10% normal goat serum) for 1 h, sections were incubated with affinity-purified rabbit anti-mouse FcRn antibody followed by 488 Fluro-conjagated goat anti rabbit IgG. Tissues were washed at least three times with 0.1% Tween-20 in PBS. Nuclei were then labeled with DAPI for 10 min. Coverslips were mounted on slides with ProLong™ antifade kit (Molecular Probes) and examined using a Zeiss LSM 510 confocal fluorescence microscopy. Images were handled in Adobe Photoshop 7.0.

Statistical Analysis.

Antibody titers, serum Gag concentration, cytokine concentration and virus titers were assessed with unpaired two-tailed t test. GraphPad Prism 5 was the software for statistical analyses.

Example 5

Production and Transcytosis of HIV Gag-Fc Fusion Proteins.

To determine whether HIV antigens targeted to FcRn in vivo would elicit antibody and cellular immune responses, we first generated a fusion protein HIV Gag-Fc/wt by cloning HIV Gag in frame with the carboxyl terminus of the heavy chain of mouse IgG2a antibody (FIG. 1A). We used mouse IgG2a Fc fragment since mouse IgG2a, but not IgG1, is capable of binding mouse FcγRI. We also generated a Gag-Fc mutant version that does not bind FcRn by creating point mutations (HQ310 and HN431) known to prevent FcRn binding to the Fc-domain. These same Fc mutations in IgG1 Fc are known to exhibit a 100-fold reduction in binding to FcRn (15). In all constructs, constant regions of the mouse IgG2a were also modified to remove the complement C1q-binding motif (21) and produce nonlytic fusion proteins. The fusion proteins were synthesized in CHO cells transfected with the Gag-Fc constructs. Secreted Gag-Fc fusion proteins formed monomers under reducing conditions, but were disulfide-linked homodimers under non-reducing conditions in Western blotting, using both the affinity-purified anti-Gag (FIG. 6B, top panel) and anti-mouse IgG Fc antibodies (FIG. 6B, bottom panel). Functional testing of the Fc-domain was confirmed by precipitating Gag-Fc/wt, but not for Gag-Fc/mut proteins with Staphylococcal protein A on beads. It has been shown that protein A and FcRn recognize overlapping amino acids of IgG Fc and mutations in this region can affect both properties. As a result, protein A effectively and competitively inhibits IgG binding to FcRn. This implies that Fc portions of IgG in the Gag-Fc/wt maintain all structures necessary for binding FcRn.

To ascertain whether the Gag-Fc/wt, but not Gag-Fc/mut, fusion proteins are transported by FcRn, we used an MDCK-FcRn cell line to transport Gag-Fc fusion proteins. MDCK cells expressing rat FcRn and β2m have been shown to specifically transport murine IgG in vitro (23). Hence, FcRn-dependent transcytosis of purified Gag-Fc/wt protein applied to the apical reservoir was transported to the basolateral reservoir (FIG. 6C, lanes 4&5), as detected by Western blot quantification. In contrast, the Gag-Fc/mut (FIG. 6C, lanes 2&3) and chicken IgY (lanes 2-5) proteins failed to transport across the MDCK-FcRn monolayer, suggesting a specific transport of the Gag-Fc/wt by FcRn. The transport was not inhibited by an excessive amount of chicken IgY which does not bind FcRn (FIG. 6C, lane 3).

We then addressed whether the Gag-Fc would appear in sera after i.n. inoculation. The expression of murine FcRn in the lung (25) was verified in epithelial cells of trachea and lungs, but not intestines, of adult mice compared with FcRn-KO mice (19) by immunofluorescence staining using a mouse FcRn specific antibody (FIG. 6D). To determine whether the Gag-Fc appears in circulation after i.n. inoculation, 20 ug of the Gag-Fc/wt, Gag-Fc/mut, or Gag proteins were administered i.n. and measured in the blood 8 hr later using ELISA. As shown in FIG. 6E, Gag-Fc/wt was detected readily in sera of wt mice, but not FcRn KO animals. In addition, the Gag-Fc/mut or Gag alone proteins were transported poorly; indicating that i.n. administered Gag-Fc/wt efficiently crossed the airway mucosal barrier. The transported Gag-Fc/wt proteins entered the circulation and persisted about 5 days, much longer than other proteins tested (FIG. 6F), although it was difficult to determine the half-life of other proteins because they were transported so poorly. Taken together, we conclude that rodent FcRn can transport the Gag-Fc/wt fusion protein across the polarized epithelial cell monolayer lining the airway tract in an FcRn-dependent manner. In addition, inactivation of the complement C1q binding motif failed to impact FcRn-mediated transport of the Gag-Fc/wt fusion protein.

Example 6

Strong Anti-Gag Antibody and T Cell Responses after FcRn-Targeted Mucosal Immunization.

To test whether FcRn-dependent transport across mucosal surfaces generates immune responses against HIV vaccine antigens, wt mice were immunized i.n. with Gag-Fc or Gag proteins in combination with the CpG and boosted 2 weeks later. Use of Gag alone allowed us to assess the transport efficiency of Gag-Fc/wt by FcRn in vivo and to determine the magnitude of increased immune responses to Gag-Fc/wt. DCs capturing antigen in a mucosal-associated lymphoid tissues or in lymph nodes primes T cells that home to the mucosa (18, 26). To overcome the normal tolerogenic function of at least some immature DCs in vivo, we included immunostimulatory DNA rich in CG motifs (CpG), an agonist for Toll-like receptor-9 (16, 27). First, we determined whether antigen targeting to FcRn by the Gag-Fc proteins elicits antibodies specific to HIV Gag protein. Antibody responses among immunized animals, including PBS control mice, were assessed at various time points up to 56 days after the primary immunization, by measuring Gag-specific serum IgG. As shown in FIG. 7A, significantly higher titers of IgG, mainly restricted to the IgG2a subclass (FIG. 7B), were seen in the Gag-Fc/wt immunized mice when compared with the other groups. The antibody response was further associated with germinal center (GC) in the spleens of immunized mice. Spleens were removed 10 days after the boost. Splenocytes were gated on $B220^+$ cells and stained for the presence of peanut agglutinin (PNA) and Fas-positive B cells. Mice immunized by the Gag-Fc/wt, but not by the Gag-Fc/mut or Gag alone proteins, developed appreciable numbers (3.98% of total isotype-switched B cells) of $FAS^+PNA^+$ $B220^+$ B cells, suggesting GC were formed after immunization (28, 29) (FIG. 2C). In addition, FcRn KO mice immunized with Gag-Fc/wt failed to show comparable numbers of $FAS^+PNA^+$ $B220^+$ B cells. These results indicate that FcRn-targeted mucosal delivery of the Gag-Fc/wt results in an effective B cell response.

An effective antibody response requires help from T cells (30). Seven days after boosting, splenocytes were harvested from immunized mice and pulsed with purified Gag; IFN-γ producing T cells were measured by flow cytometry. We detected a significant number of IFN-γ producing $CD4^+$ (FIG. 7D, upper panel) and $CD8^+$ (FIG. 7D, bottom panel) T cells in response to Gag in mice immunized with Gag-Fc/wt, but not in any of other groups including mice immunized with the Gag-Fc/mut protein or FcRn KO mice immunized with the Gag-Fc/wt protein. In wild type mice immunized with the Gag-Fc/wt proteins, about 1% of the CD4+ and 2% of the CD8+ T cells responded to Gag stimulation. Thus, targeting the Gag-Fc/wt to FcRn via mucosal administration was at least 10-20 times as effective at initiating IFN-γ-producing CD4+ and CD8+ T cell immunity compared with Gag-Fc/mut or Gag-immunized mice. Cytokine responses were mainly IFN-γ and IL-2; little IL-4 was seen in cultures pulsed with antigen (FIG. 7). Mucosal immunization with Gag-Fc/wt proteins therefore induced strong $CD4^+$ and $CD8^+$ T cell responses, whereas the immunization with Gag-Fc/mut or the Gag-Fc/wt in FcRn KO mice did not. We concluded that immunizing by targeting HIV antigens to FcRn together with CpG, produces a strong response to HIV Gag including both B and T cell immunity.

Example 7

FcRn-Targeted Mucosal Immunization Significantly Reduced Viral Replication after Challenge.

To determine whether to FcRn-mediated mucosal vaccine delivery could protect against viral infection at a distant mucosal site, we challenged intravaginally (ivag) the immune mice with 5×10⁷ pfu of virulent recombinant vaccinia virus (VV) expressing HIV-1 Gag (rVV-Gag) at four weeks after the boost. Ovary tissues were harvested at the peak of infection, day 5. Control mice (PBS) had the highest titers of rVV-Gag in ovaries after virus challenge (FIG. 8A). Mice immunized with Gag-Fc/mut or the FcRn KO mice immunized with Gag-Fc/wt, had high titers of rVV-Gag in their ovaries. In marked contrast to these control mice, virus titers measured in ovary tissues of wild type mice immunized with the Gag-Fc/wt proteins showed significantly lower levels of virus by day 5 after challenge (FIG. 8A). Furthermore, in comparison with Gag-Fc/mut immunized wild type mice or Gag-Fc/wt-immunized FcRn KO mice, the uterine sizes were much smaller in mice immunized by Gag-Fc/wt proteins after infection with rVV-Gag, presumably because of reduced edema, hemorrhage and inflammation (FIG. 8B). Control (uninfected) mice sampled at day 0 showed normal uterus morphology. The amounts of virus detected were consistent with the gross changes in the uteri among groups of animals. Overall these results demonstrate that i.n. administration of Gag-Fc/wt proteins in wild type mice efficiently induced protective immunity. These results suggest a significant role for the immune responses from FcRn-dependent mucosal immunization in the control of viral infection.

Example 8

Induction of Local Mucosal Immune Responses.

Sexually transmitted HIV enters through mucosal sites and spreads rapidly to distant mucosal and systemic lymphoid tissues. Local immune responses and protection against virus dissemination from mucosal tissues are important factors for vaccine development. Local mucosal immunization confers maximum protection against mucosal challenge (16, 31). Mediastinal lymph nodes (MLN) are the sites where mucosal immune responses are initiated against vaccine antigens that reach the lung after intranasal immunization. We looked at changes in MLN GC after FcRn-targeted mucosal delivery of the Gag-Fc/wt. As shown in FIG. 9A, intranasal immunization with Gag-Fc/wt efficiently induced an increased frequency (3.93%) of FAS⁺PNA⁺ B220⁺ B cells in the MLN compared to 0.51 to 0.98% of Fas+PNA+ B220+ cells in other groups by 10 days after the boost. Therefore, FcRn-targeted HIV Gag mucosal immunization induced the formation of GC in draining MLN.

Antibodies, in particular secretory IgA and IgG, represent a first line of defense on mucosal surfaces. To assess the ability of the FcRn-targeted immunization to induce Gag-specific antibody in mucosal secretions, the bronchial alveolar lavage (BAL) specimens were collected two weeks following the boost and tested for Gag-specific IgG and IgA by ELISA. Furthermore, in order to determine if the antibody responses induced by i.n. immunization were disseminated to remote mucosal sites, vaginal washes were collected for antibody analyses. The Gag-specific IgG were increased significantly in lung lavages by 10 days after the boost (FIG. 9B) and in vaginal washes two weeks after the boost (FIG. 9C) among the Gag-Fc/wt immunized mice. Low levels of the Gag-specific IgG were detected in BAL and vaginal washings of mice immunized with the Gag-Fc/mut or Gag alone. Only wild type, but not FcRn KO mice that received the Gag-Fc/wt, had highest levels of Gag-specific IgG antibodies in the BAL and vaginal washings suggesting the appearance of mucosal IgG is FcRn dependent. In contrast, we only detected a small amount of IgA in all BAL and vaginal washings (data not shown).

To address whether FcRn targeted delivery of mucosal vaccine can induce T cell immune responses in the vaginal tissue, infiltrated vaginal lymphocytes were isolated from the challenged mice and pulsed with the purified Gag; IFN-γ specific producing T cells were measured by flow cytometry. We detected significant numbers of IFN-γ producing CD4+ (FIG. 9D, upper panel) and CD8+ (FIG. 9D, bottom panel) T cells in response to Gag in mice immunized with the Gag-Fc/wt in comparison with other groups, including the mice immunized with Gag-Fc/mut or the FcRn KO mice immunized with Gag-Fc/wt proteins. Immunization with the Gag-Fc/wt fusion protein induced strong IFN-γ-producing CD4⁺ and -CD8⁺ T cell responses, whereas immunization with the Gag-Fc/mut or the FcRn KO mice immunized with the Gag-Fc/wt protein did not.

Example 9

FcRn Targeted Mucosal Immunization Elicits Long-Term Humoral and T Cell Immune Responses.

Activated B cells, can differentiate to plasma cells that secrete antibodies at high rate and reside in niches in the bone marrow and others become memory B cells that respond rapidly to antigenic restimulation and contribute to the plasma cell pool serum antibody levels over a prolonged period of time (32). To determine whether antigen targeting to FcRn-mediated IgG transfer pathway leads to long-lasting memory B cell immune responses, splenocytes were isolated 4 months after the boost and restimulated with Gag protein. Memory B cells were barely present after immunization with control Gag or PBS but were increased with Gag-Fc/wt (FIG. 10A). Differences between the Gag-Fc/wt immunized mice versus the Gag-Fc/wt immunized FcRn KO or the Gag-Fc/mut immunized mice were statistically significant. To determine whether antigen targeting to FcRn also elicited plasma cells that secreted Gag-specific antibodies, the number of IgG-secreting plasma cells in the bone marrow were measured by ELISPOT. High numbers of Gag-specific IgG secreting cells were present in bone marrow of mice immunized with Gag-Fc/wt compared with other groups (FIG. 10B). To show whether increased memory B cells and antibody-secreting plasma cells correspond to a rise in IgG production and maintenance, IgG antibody in the sera were measured four months (the longest point we tested) after the boost. High titers of Gag-specific IgG antibodies were maintained in mice immunized with the Gag-Fc/wt, but not the Gag-Fc/mut or Gag alone (FIG. 10C). Immunization with the Gag-Fc/wt was about 20-fold more effective, respectively, than immunization with Gag-Fc/mut or HIV Gag alone, indicating that Gag-specific antibody persisted much longer after FcRn targeted mucosal immunization.

An important feature of memory T cells is their proliferative response upon antigen restimulation. To test if memory T cells could be detected 4 months following FcRn-targeted mucosal immunization, we measured CD4⁺ and CD8⁺ T cell proliferation in response to HIV Gag antigen restimulation. Splenocytes isolated four months after the boost were stimulated in vitro with HIV Gag (FIG. 10D). After 4 days incubation, the CFSE profiles were read on CD4- or CD8-gated T cells and subsequently analyzed by flow cytometry. We detected significant CD4⁺ (FIG. 10D, upper panel) and CD8⁺ (FIG. 10D, bottom panel) memory T cell proliferation in response to Gag restimulation, in mice immunized with Gag-Fc/wt but not in other groups. The Gag-specific T cell response to Gag-Fc/wt in wild type mice included a substantial memory component. Recall IL-2 and IFN-γ cytokine responses were also detected within 12-48 hr of Gag restimulation among mice immunized with the Gag-Fc/wt, but not with other groups (data not shown). Collectively, these results show that mucosal immunization by antigen targeting to FcRn was effective in eliciting long term memory T cell immune responses to HIV Gag antigen.

To test whether memory immune responses elicited from FcRn targeted mucosal immunization are functional for resisting virus, we challenged the immunized mice intravaginally with rVV-Gag ($5 \times 10^7$ pfu) at four months after the boost. Ovary tissues were harvested 5 days after challenge and virus titers were measured. Mice immunized by the Gag-Fc/mut, Gag alone, or FcRn KO mice immunized by Gag-Fc/wt failed to control viral replication (FIG. 10E). In contrast, virus titers in ovary tissues from wild type mice immunized by Gag-Fc/wt were significantly lower at 5 days after challenge (FIG. 10E). Virus titer was significantly higher in either Gag-Fc/mut immunized wt mice or Gag-Fc/wt-immunized FcRn KO mice, demonstrating that the protection was from HIV Gag specific memory immune responses.

DISCUSSION

A chimeric fusion protein comprised of HIV Gag protein and a modified murine Fc portion from IgG, was transported efficiently across mucosal epithelium. Transported Gag-Fc persisted much longer in the blood, which is consistent with fact that FcRn protects IgG from degradation (10). When Gag-Fc fusion protein was used for intranasal immunization, mice developed strong T cell (CD4+ and CD8+) and B cell responses including persistent memory. By introducing genetically modified Fc fragments into the HIV Gag protein or using FcRn KO mice, we show that the capacity for transepithelial transport and for eliciting strong immune responses both depended on the intact Fc sequence in the fusion protein and FcRn expression on murine cells. Finally, immune responses elicited by intranasal immunization were sufficiently potent to protect mice from infection at a remote mucosal site. The properties of antigen transport, antigen persistence in blood, B and T cell immune responses and protection from virus challenge all required intact Fc sequences in the fusion protein and FcRn expression in the mouse.

FcRn-targeted immunization induced strong antibody and cellular immune responses against HIV Gag. Strong responses were detected at mucosal and systemic sites. The Gag-Fc/wt fusion proteins induced strong IFN-g-producing $CD8^+$ and $CD4^+$ T cell responses relative to the Gag-Fc/mut or HIV Gag proteins. The mucosal immunization of FcRn KO mice demonstrated that FcRn was absolutely essential for mucosal immunization. Gag antigen targeted to FcRn increased the efficiency with which HIV Gag antigens engendered strong T cell immunity, when given together with CpG stimuli to promote DC maturation.

We also noticed that the FcRn-targeted mucosal subunit vaccine was exceptional in inducing high levels of serum IgG production with a preference for IgG2a as the major isotype. This is not surprising because the type 1 cytokine IFN-γ is associated with production of IgG2a, whereas the type 2 cytokine IL-4 helps switching to IgG1. T cells analyzed in this study secreted a lesser amount of IL-4. However, we did not distinguish between the effect of mucosal targeting or CpG in our study.

An effective vaccine to block sexual transmission of HIV must be capable of eliciting protective mucosal immune responses to stall initial virus replication, slow CD4+ depletion and inhibit rapid dissemination of virus from the mucosa into systemic lymphoid tissues (33). Our strategy of FcRn-targeted mucosal delivery for HIV Gag antigen, engendered strong mucosal immune responses. We observed IgG in lung and vaginal washings and cytokine-producing T cells in vaginal tissues of immunized mice. Of note is the observation that levels of Gag-binding IgG levels in BAL- or vaginal washes were much higher than the specific IgA detected. Indeed, IgG is a major isotype of immunoglobulins in the lower respiratory and reproductive tracts (34, 35). Thus, IgG antibodies detected in BAL and vaginal washings may be produced locally or come from the circulation, but it was clear that HIV antigen targeted to FcRn plus adjuvant produced strong humoral and T cell mucosal immune responses.

Perhaps our most compelling finding was that FcRn-targeted intranasal immunization protected against intravaginal virus challenge. Viral replication in ovary tissues was reduced in immune mice and there was less evidence of gross pathology in the uterus. Intranasal immunization targets cells in the nasal lymphoid tissue (NALT) and its draining lymph nodes. To separate vaginal immune responses, antibody secreting cells and IFN-γ producing T cells likely migrate from the airway to the genital tract (36, 37). We used this system to test whether humoral and T cell immune responses elicited by FcRn-targeted, HIV Gag intranasal delivery protected the distant vaginal mucosa. We know that protective responses depended on intact Fc and FcRn expression and both T and B cell responses were detected. Several immune mechanisms may account for protection. T lymphocytes were present in the vaginal epithelium of rVV-Gag infected mice at times coinciding with virus clearance. IFN-γ producing CD4+ and CD8+ T cells were also present in vaginal tissues of immune mice. IFN-γ is indispensable for resistance to genital mucosal infections (24, 38, 39) and these strong T cell responses may also promote direct lysis of MHC class I or II-bearing infected cells. The effector/memory $CD4^+$ and $CD8^+$ T cells in mucosal effector sites (lamina propria) are crucial for containing initial HIV replication and subsequent virus discrimination. Consistent with these data, previous studies reported that the breadth of Gag specific T cell responses correlated with control of viral load in HIV-1-infected humans (40) and SIV (simian immunodeficiency virus)-infected rhesus macaques (41). It may be argued that local T cell responses observed after challenge with rVV-Gag, were due to nonspecific inflammatory responses against the challenge virus. However, the responses were Gag specific and occurred only in wild type mice immunization with Gag-Fc/wt. It is important to note that antigens used in this study contained only a single HIV Gag antigen and did not include a homologous Env gp120 antigen. The observed protection was likely provided by Gag-specific cellular immune responses, since it is unlikely that Gag-specific antibodies offered substantial protection in blocking viral attachment and penetration into target cells. This may explain why Gag-Fc/wt immunized mice failed to clear virus completely after infection however, we cannot exclude a protective role for antibody-dependent cell-mediated cytotoxicity (42). Significant amounts of Gag-specific IgG antibody were present in BAL and vaginal secretions in our study and IgG is a major protective antibody in vaginal secretions after immunization (34). The potential roles for antibody produced from FcRn-targeted HIV gp120 antigen immunization may be more important for full protection in humans. Additional studies conducted to test this idea are ongoing.

FcRn-targeted mucosal immunization produced durable memory immune responses. Immunological memory is exemplified by increased levels of effector T and B cells and, functionally, by the ability to respond faster and more vigorously to a second encounter with the vaccine antigens (43). Hence, another criterion for successful HIV vaccines is the ability to generate durable memory responses that maintain strong immune surveillance over lengthy intervals. These effector memory responses might improve vaccine efficacy by impairing viral replication at its earliest stage or at viral entry sites (44). An obstacle for the successful implementation of HIV mucosal vaccine is the production and maintenance of a pool of memory lymphocytes. It has been difficult to implement an HIV subunit vaccine strategy via mucosal surfaces because these approaches have resulted in inefficient immune responses which waned rapidly. However, the most striking finding in this study is that the FcRn targeted mucosal delivery of HIV antigen sustained high levels of HIV Gag-specific IgG-secreting plasma cells and memory B and T cells. Presence of Gag-specific memory B cells in the spleen and long-lived plasma cells in the bone marrow may explain the high levels of IgG antibody in sera. T cell memory was also long-lived in our model. The reason for generating potent memory T cell activity is not completely clear, although IL-2-producing T cells were generated and may be important for supporting long-lived memory T cells (45).

The FcRn might contribute to increased immunity in two ways: by efficiently transporting Gag-Fc and protecting it from degradation. It is generally believed that slow release of vaccine antigen over a prolonged time can facilitate long-term memory immune responses. As a result, long-term retention of Gag-specific plasma cells and memory lymphocytes might be important for resistance to HIV replication and transmission. Indeed, this conclusion was strongly supported by the observation that protective immune responses were still present at 4 months after immunization (FIG. 10E). FcRn is expressed in both the upper and central airways in non-human primates as well as in humans. Additionally, FcRn can mediate a pulmonary delivery of erythropoietin Fc fusion protein in non-human primates (Bitoni et al., 2004, PNAS 101, 9763-8). Therfore, it will be of interest to determine whether FcRn-targeted mucosal immunization is capable of eliciting the long-term protective memory immune responses in modulation of replication and transmission of SIV in a rhesus macaque model.

In conclusion, our study demonstrates clearly that a subunit vaccine based on an HIV Gag-Fc fusion protein, targets the antigen to FcRn and induces long-term immune memory protection against mucosal virus challenge. Robust durable immune responses with protection against virus challenge document the potential for this approach in developing vaccines against mucosal HIV exposure. This conclusion is supported further by our earlier work that wild-type, but not FcRn knockout mice immunized intranasally with genital herpesviral glycoprotein gD-Fc, resulted in complete protection when animals were challenged intravaginally with virulent HSV-2 (20). From both studies, we deduce that a FcRn-targeted HIV subunit vaccine delivers soluble antigens to mucosal DCs and gives rise to long-lived T cell help for antibody responses (30, 46, 47).

The following references were cited in Examples 5-9.
1. McMichael, A. J. et al., *Nat Rev Immunol* 10:11-23.
2. Broliden, K. et al., 2009 *J Intern Med* 265:5-17.
3. Demberg, T., and M. Robert-Guroff, 2009, *Int Rev Immunol* 28:20-48.
4. Neutra, M. R. et al., 2001 *Nat Immunol* 2:1004-1009.
5. Neutra, M. R., and P. A. Kozlowski, 2006, *Nat Rev Immunol* 6:148-158.
6. Misumi, S. et al, 2009, *J Immunol* 182:6061-6070.
7. Nochi, T. et al., 2007, *J Exp Med* 204:2789-2796.
8. Burmeister, W. P. et al., 1994, *Nature* 372:336-343.
9. Roopenian, D. C., and S. Akilesh, 2007, *Nat Rev Immunol* 7:715-725.
10. Ghetie, V., and E. S. Ward. 2000, *Annu Rev Immunol* 18:739-766.
11. Dickinson, B. L. et al., 1999, *J Clin Invest* 104:903-911.
12. He, W. et al., 2008, *Nature* 455:542-546.
13. Israel, E. J. et al., 1996, *Immunology* 89:573-578.
14. Junghans, R. P., and C. L. Anderson, 1996, *Proc Natl Acad Sci USA* 93:5512-5516.
15. Kim, J. K. et al., 1994, *Eur J Immunol* 24:2429-2434.
16. Belyakov, I. M. and J. D. Ahlers, 2009, *J Immunol* 183:6883-6892.
17. Abrahamson, D. R. et al., 1979, *Science* 206:567-569.
18. Yoshida, M. et al., 2004, *Immunity* 20:769-783.
19. Roopenian, D. C. et al., 2003, *J Immunol* 170:3528-3533.
20. Ye, L. et al., 2008, *J Immunol* 181:2572-2585.
21. Duncan, A. R., and G. Winter, 1988, *Nature* 332:738-740.
22. Liu, X. et al., 2008, *J Immunol* 181:449-463.
23. Tesar, D. B. et al., 2006, *Traffic* 7:1127-1142.
24. Gupta, S. et al., 2005, *J Virol* 79:7135-7145.
25. Spiekermann, G. M. et al., 2002, *J Exp Med* 196:303-310.
26. Liu, L. M., and G. G. MacPherson, 1993, *J Exp Med* 177:1299-1307.
27. van Duin, D. et al., 2006, *Trends Immunol* 27:49-55.
28. Hao, Z. et al., 2008, *Immunity* 29:615-627.
29. Moyron-Quiroz, J. E. et al., 2004, *Nat Med* 10:927-934.
30. Boscardin, S. B. et al., 2006, *J Exp Med* 203:599-606.
31. Gallichan, W. S., and K. L. Rosenthal, 1998, J Infect Dis 177:1155-1161.
32. Bernasconi, N. L., E. Traggiai, and A. Lanzavecchia, 2002, *Science* 298:2199-2202.
33. Belyakov, I. M., and J. D. Ahlers, 2008, *Trends Immunol* 29:574-585.
34. Parr, E. L., and M. B. *Parr*, 1997, *J Virol* 71:8109-8115.
35. Russell, M. W. 2002, *Am J Reprod Immunol* 47:265-268.
36. Pal, S. et al., 1996, *Infect Immun* 64:5341-5348.
37. Wu, H. Y. et al., 1997, *Scand J Immunol* 46:506-513.
38. Milligan, G. N. et al., 2004, *Virology* 318:507-515.
39. Sha, B. E. et al., 1997, *J Acquir Immune Defic Syndr Hum Retrovirol* 16:161-168.
40. Kiepiela, P. et al., 2007, *Nat Med* 13:46-53.
41. Liu, J. et al., 2009, *Nature* 457:87-91.
42. Forthal, D. N. et al., 2001, *J Virol* 75:6953-6961.
43. Ahmed, R., and D. Gray, 1996, *Science* 272:54-60.
44. Hansen, S. G. et al., 2009, *Nat Med* 15:293-299.
45. Dooms, H. et al., 2007, *J Exp Med* 204:547-557.
46. Leonetti, M. et al., 1998, *J Immunol* 160:3820-3827.
47. Trumpfheller, C. et al., 2006, *J Exp Med* 203:607-617.

What is claimed is:

1. A composition comprising a fusion protein comprising an Fc fragment of an immunoglobulin recognized by neonatal receptors (FcRn), wherein the Fc fragment is fused at its amino terminal end to a desired antigen, wherein the Fc fragment comprises the hinge region, a CH2 domain and a CH3 domain of the immunoglobulin, wherein C1q motif has been mutated such that it renders the fragment non-lytic, and wherein there is a linker between the hinge region and the antigen, and wherein the antigen is selected from the group of antigens consisting of antigens from viruses, bacteria, parasites, and fungi, wherein said composition is administered to a mucosal epithelium and induces in said subject the formation of memory lymphocytes specific for said antigen.

2. The composition of claim 1, wherein said composition protects against viral infection at a mucosal site distant and different from the site of vaccine administration.

3. The composition of claim 1, wherein said composition is capable of promoting and sustaining antigen specific plasma cells in a subject for at least 6 months after an administration of said composition.

4. The composition of claim 2, wherein said virus antigen is chosen from the group consisting of Herpes simplex virus type 2 gD protein, HIV Gag(p24), HIV gp120, influenza HA, influenza NA, influenza M2, respiratory syncytia virus F protein, respiratory syncytia virus G protein, and human papilloma virus protein.

5. The composition of claim 2, wherein said bacterial antigen is chosen from the group consisting of *mycobacterium tuberculosis* Ag85B, *mycobacterium tuberculosis* ESAT6, *Streptococcus pneumonia* PspA, *Streptococcus pneumonia* PsaA, and *Streptococcus pneumonia* CPbA.

6. The composition of claim 1, wherein said mucosal epithelium is chosen from the group consisting of lungs, intestines, colon, nasal tissue, vaginal tissue.

7. The composition of claim 1, wherein said subject is animal or human.

8. The composition of claim 1, further comprising an adjuvant.

9. The composition of claim 8, wherein said adjuvant is CpG.

10. A pharmaceutical composition comprising an effective amount of a fusion protein of claim 1.

11. The composition of claim 1, wherein the viral antigen is the respiratory syncytia virus F or the influenza HA.

12. The composition of claim 1, wherein the viral antigen is the respiratory syncytia virus F protein.

13. The composition of claim 1 wherein the viral antigen is the influenza HA.

14. A method for stimulating a mucosal T cell immune response in a subject comprising administering an effective amount of the composition of claim 1, said administration being to a mucosal epithelium.

15. The method of claim 14 further comprising administering an adjuvant with said fusion protein.

16. The method of claim 15 wherein said adjuvant is CpG.

* * * * *